United States Patent [19]

Aszodi et al.

[11] Patent Number: 5,455,238
[45] Date of Patent: Oct. 3, 1995

[54] CEPHALOSPORINS

[75] Inventors: Jozsef Aszodi, Pontault Combault; Jean-François Chantot, Gressy en France; Patrick Fauveau, Livry Gargan; Solange Gouin D'Ambrieres, Paris; Daniel Humbert, Fontenay sous Bois, all of France

[73] Assignee: Roussel Uclaf, France

[21] Appl. No.: 989,235

[22] Filed: Dec. 11, 1992

[30] Foreign Application Priority Data

Dec. 12, 1991 [FR] France ................................. 91 15416
Sep. 28, 1992 [FR] France ................................. 92 11520

[51] Int. Cl.⁶ ...................... C07D 501/24; A61K 31/545
[52] U.S. Cl. .......................... 514/202; 514/206; 540/222; 540/223
[58] Field of Search ................... 540/222, 229, 540/221; 514/202, 206

[56] References Cited

U.S. PATENT DOCUMENTS

| 4,866,055 | 9/1989 | Katr et al. | 514/206 |
| 5,075,298 | 12/1991 | Aszodi et al. | 514/206 |
| 5,234,920 | 8/1993 | Okita et al. | 540/227 |
| 5,373,000 | 12/1994 | Machida | 514/202 |
| 5,373,001 | 12/1994 | Aszodi et al. | 514/202 |
| 5,397,779 | 3/1995 | Aszodi et al. | 514/206 |

Primary Examiner—Nicholas Rizzo
Attorney, Agent, or Firm—Bierman and Muserlian

[57] ABSTRACT

A syn isomer in (R) or (S) form or a mixture thereof of a compound of the formula

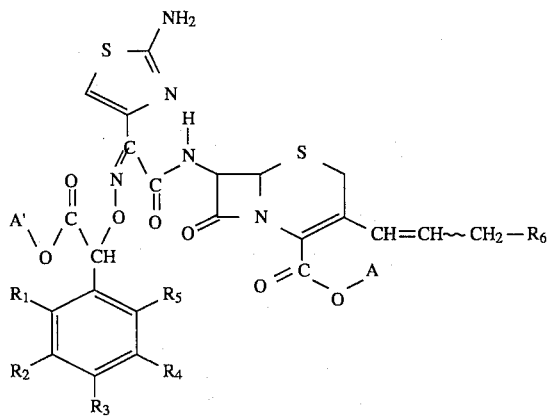

in the form of an internal salt or a non-toxic, pharmaceutically acceptable acid addition salt wherein $R_1$, $R_2$, $R_3$ and $R_5$ are individually defined in the specification, $R_4$ is —OH or alkoxy of 1 to 8 carbon atoms, A and A' are individually selected from the group consisting of hydrogen, an equivalent of an alkali metal or alkaline earth metal, magnesium, ammonium and an organic amine, or one or two of —COOA or —COOA' ARE —CO₂—, the wavy line means —CH₂R₆ can be in the E or Z position, $R_6$ in the quaternary ammonium form is selected from the group consisting of

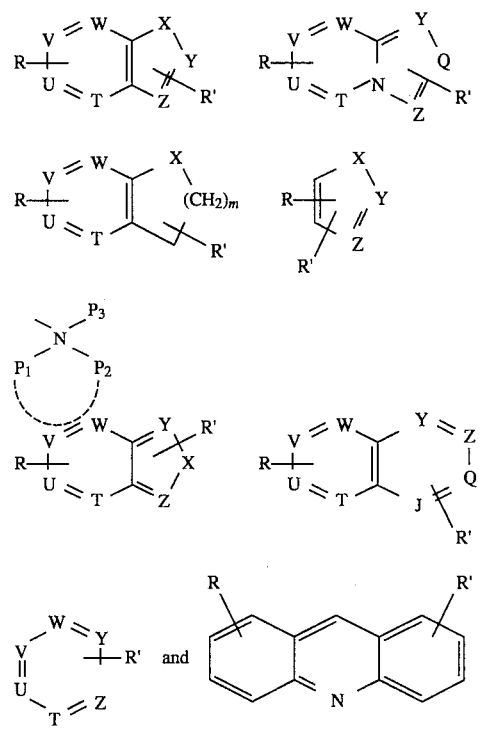

X is defined as in the specification with the proviso that when $R_3$ is —OH or alkoxy of 1 to 8 carbon atoms, at least one $R_1$, $R_2$ and $R_5$ is other than hydrogen having antibacterial properties.

13 Claims, No Drawings

CEPHALOSPORINS

STATE OF THE ART

Related prior art includes EP application No. 0,266,060 and U.S. Pat. No. 4,486,586 and No. 5,075,298.

OBJECTS OF THE INVENTION

It is an object of the invention to provide the novel compounds of formula I and their non-toxic, pharmaceutically acceptable acid addition salts and a process and intermediates for their preparation.

It is another object of the invention to provide novel antibacterial compositions and a novel method of combatting bacterial infections in warm-blooded animals.

These and other objects and advantages of the invention will become obvious from the following detailed description.

THE INVENTION

The novel compounds of the invention are the syn isomer in (R) or (S) form or a mixture thereof of a compound of the formula

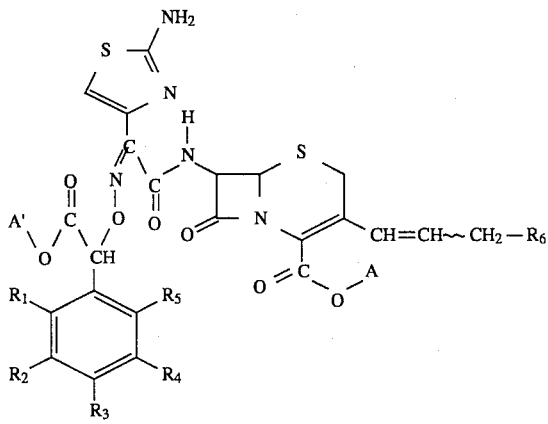

I in the form of an internal salt or a non-toxic, pharmaceutically acceptable acid addition salt wherein $R_1$, $R_2$, $R_3$ and $R_5$ are individually selected from the group consisting of hydrogen, halogen, hydroxy, alkyl of 1 to 4 carbon atoms optionally substituted with at least one halogen, alkoxy and alkylthio of 1 to 4 carbon atoms, $-NO_2$, $-CN$, $-NH_2$, mono- and dialkylamino of 1 to 4 alkyl carbon atoms, carbamoyl, (alkylamino) carbonyl of 2 to 5 carbon atoms, (dialkylamino) carbonyl of 3 to 9 carbon atoms, carboxy, alkoxycarbonyl of 2 to 5 carbon atoms, acyloxy of 1 to 8 carbon atoms and

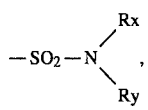

Rx and Ry are individually hydrogen or alkyl of 1 to 4 carbon atoms, $R_4$ is $-OH$ or alkoxy of 1 to 8 carbon atoms, A and A' are individually selected from the group consisting of hydrogen, an equivalent of an alkali metal or alkaline earth metal, magnesium, ammonium and an organic amine, or one or two of $-COOA$ or $-COOA'$ are $-CO_2^-$, the wavy line means $-CH_2R_6$ can be in the E or Z position, $R_6$ in the quaternary ammonium form is selected from the group consisting of

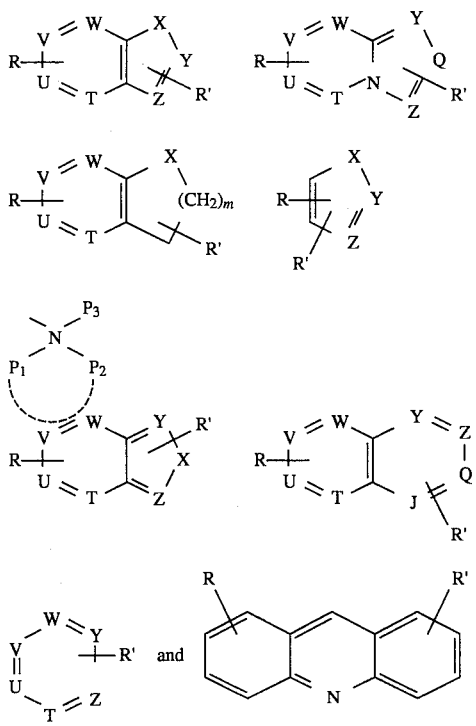

X is selected from the group consisting of $-CH_2-$, $-NH-$, $-O-$ and $-S-$, Q, J, Y, T, U, V, W and Z are individually $=N-$ or $-CH=$, each of cyclics containing 1 to 5 heteroatoms of which at least one is $=N-$ and optionally substituted by at least one R or R', R and R' are individually selected from the group consisting of halogen, alkyl and alkoxy of 1 to 4 carbon atoms, halogen, $-CN$, $-COOQ_1$, $-CONQ_1Q_2$, $-NQ_1Q_2$, $-SO_2NQ_1Q_2$, $-CSNH_2$, $-NHCOQ_1$, $-CH=NOH$, $-CH=N-O-Q_1$, $-CH_2CN$, $-SQ_1$ and $-CH_2-S-Q_1$, $Q_1$ and $Q_3$ are individually hydrogen or alkyl of 1 to 4 carbon atoms, $P_1$, $P_2$ and $P_3$ are individually alkyl of 1 to 4 carbon atoms optionally substituted with a substituent of R or R' or $P_1$ and $P_2$ taken together with the nitrogen to which they are attached form a 5 or 6 ring heterocycle with the proviso that when $R_3$ is $-OH$ or alkoxy of 1 to 8 carbon atoms, at least one of $R_1$, $R_2$ and $R_5$ is other than hydrogen.

Examples of alkyl and alkoxy of 1 to 4 carbon atoms are methyl, ethyl, propyl, isopropyl, butyl, isobutyl, sec.-butyl, tert.-butyl, methoxy, ethoxy, propoxy, isopropoxy, butoxy, isobutoxy, sec.-butoxy and tert.-butoxy. Examples of alkylthio of 1 to 4 carbon atoms are methylthio, ethylthio, propylthio, isopropylthio, butylthio, isobutylthio, sec.-butylthio and tert.-butylthio.

Examples of alkylamino of 1 to 4 carbon atoms are methylamino, ethylamino, propylamino, isopropylamino, butylamino, isobutylamino, sec.-butylamino and tert.-butylamino while examples of dialkylamino of 2 to 8 carbon atoms are dimethylamino, diethylamino, dipropylamino, diisopropylamino, dibutylamino, diisobutylamino, ethyl methylamino, propyl methylamino, butyl methylamino and propyl ethylamino.

Examples of (alkylamino) carbonyl of 2 to 5 carbon atoms are (methylamino) carbonyl, (ethylamino) carbonyl, (propylamino) carbonyl, (isopropylamino) carbonyl and (butylamino) carbonyl. Examples of alkoxycarbonyl of 2 to 5 carbon atoms are methoxycarbonyl and ethoxycarbonyl. Examples of (dialkylamino) carbonyl of 3 to 9 carbon atoms are (dimethylamino) carbonyl, (diethylamino) carbonyl, (dipropylamino) carbonyl.

Examples of acyloxy of 1 to 8 carbon atoms are acetoxy, propionyloxy and benzoyloxy while examples of halogen are fluorine, chlorine, bromine or iodine.

When $P_1$ and $P_2$ form a heterocycle with the nitrogen atom to which they are attached, it may be pyrrolidine, morpholine or piperidine. When $R_4$ is alkoxy, it is preferably acetoxy, propionyloxy or benzoyloxy.

Among the values of A' and A are an equivalent of sodium, potassium, lithium, calcium, magnesium or ammonium and organic bases such as methylamine, propylamine, trimethylamine, diethylamine, triethylamine, N,N-dimethylethanolamine, tris [(hydroxymethyl)-amino]-methane, ethanolamine, pyridine, picoline, dicyclohexylamine, morpholine, benzylamine, procaine, lysine, arginine, histidine and N-methylglucamine.

The products of formula I can also appear in the form of a pure internal salt, in salified form or in a combined form with the acids of the solution. Among the acids with which the products of formula I can be salified include acetic acid, trifluoroacetic acid, maleic acid, tartaric acid, methanesulfonic acid, benzenesulfonic acid, p-toluenesulfonic acid, phosphoric acid, sulfuric acid, hydrochloric acid, hydrobromic acid, hydroiodic acid.

In a preferred method of the invention, A' is hydrogen and $CO_2A$ is $CO_2^-$.

The expression in the form of quaternary ammonium indicates that $R_6$ is linked by one of the nitrogen atoms that it contains. Preferably $R_6$ is one of the following:

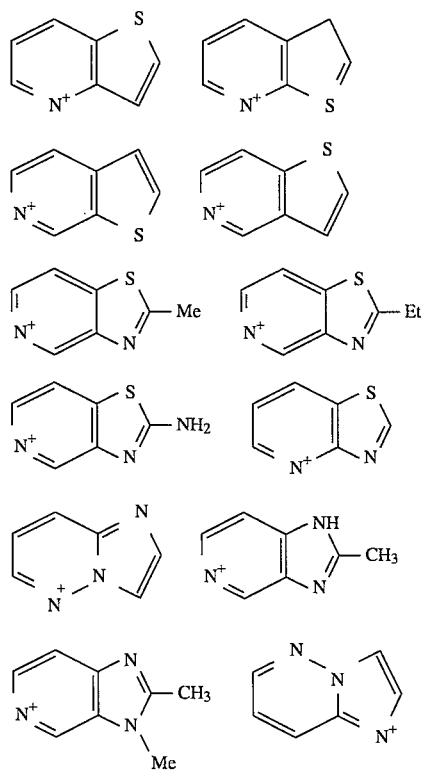

-continued

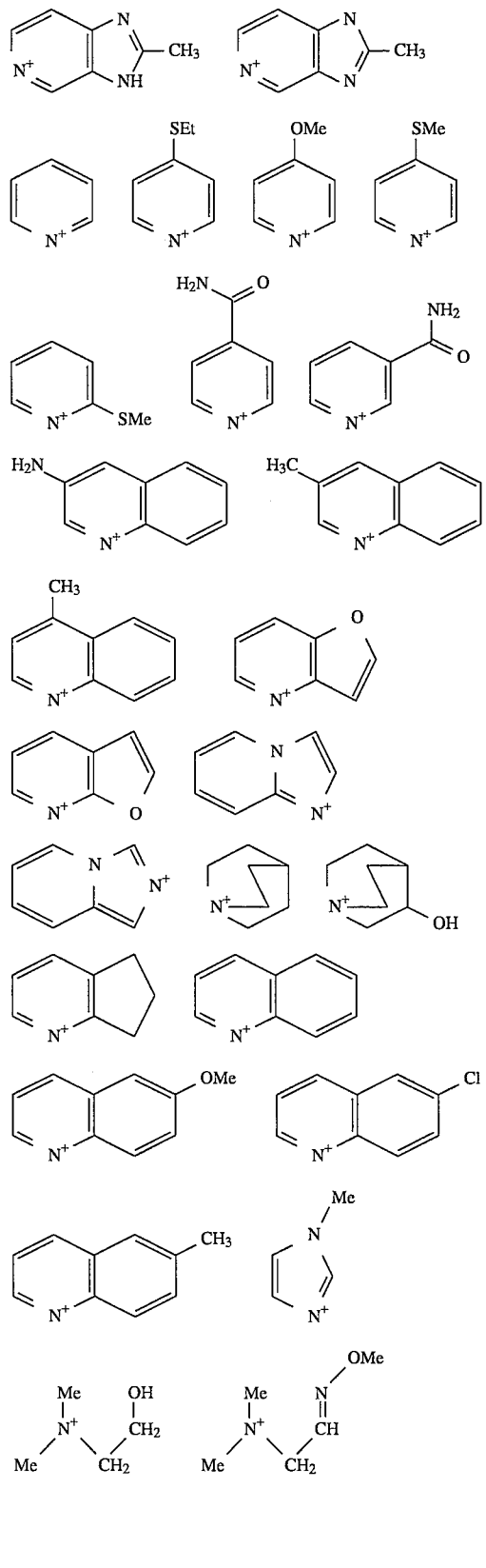

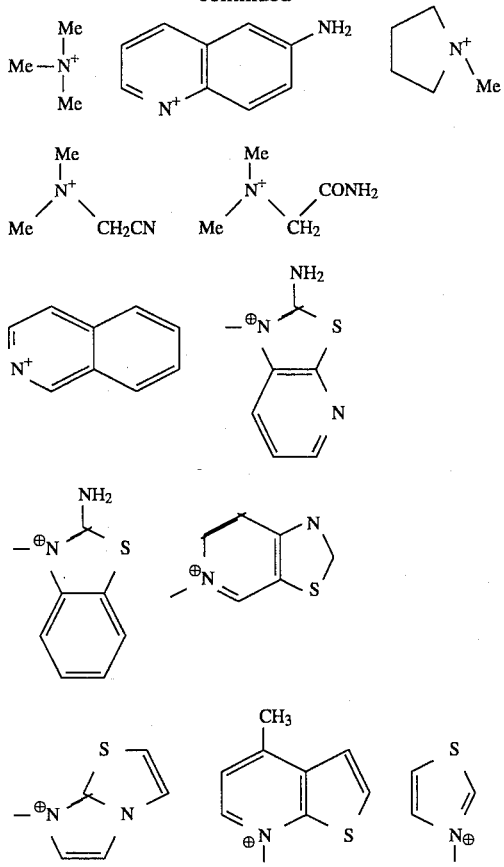

More preferably $R_6$ is quinolinium, isoquinolinium, 4-(methylthio)-pyridinium, thieno[2,3-b]pyridinium, imidazo(1,2-a)pyridinium or 6,7-dihydro-5H-pyrindinium, those in which $R_3$ and $R_4$ individually are hydroxy and those in which $R_2$ and $R_5$ are chlorine or fluorine, those in which $R_1$ and $R_2$ are fluorine and those in which $R_2$ is methoxy and one of $R_1$ or $R_5$ is chlorine.

Specific compounds of the invention are the internal salt of (6R-(3-(E) 6α,7β(Z)))-1-(3-(7-(((2-amino-4-thiazolyl) (carboxy-(2,3-difluoro-4,5-dihydroxy-phenyl)-methoxy)-imino)-acetamido)- 2-carboxy-8-oxo-5-thia-1-azabicyclo[4,2,0]oct-2-en-3-yl)-2-propenyl) imidazo(1,2-a)pyridinium, the internal salt of (6R-(3-(E)6α,7β(Z)))-1-(3-(7-((( 2-amino-4-thiazolyl) (carboxy-(2,5-difluoro-3,4-dihydroxy-phenyl)-methoxy)-imino)-acetamido)- 2-carboxy-8-oxo-5-thia-1-azabicyclo[ 4,2,0]oct-2-en-3-yl)-2-propenyl)-imidazoa)pyridinium, the internal salt of (6R-(3-(E) 6α,7β(Z)))-1-(3-(7-((( 2-amino-4-thiazolyl) (carboxy-(2-chloro-4,5-dihydroxy-3-methoxy-phenyl)-methoxy)-imino)-acetamido)- 2-carboxy-8-oxo-5-thia-1-azabicyclo [4,2,0]oct-2-en-3-yl)-2-propenyl)quinolinium, the internal salt of (6R-(3-(E) 6α,7β(Z)))-1-(3-(7-((( 2-amino-4-thiazolyl) (carboxy-(2,5-dichloro-3,4-dihydroxy-phenyl)-methoxy)-imino)-acetamido)- 2-carboxy-8-oxo-5-thia-1-azabicyclo [4,2,0]oct-2-en-3-yl)-2-propenyl)-6,7-dihydro-5H-pyridininium, the internal salt of (6R-(3-(E) 6α,7β(Z(S*))))-1-(3-(7-((( 2-amino-4-thiazoyl) (carboxy-(3,4-dihydroxy-5-fluorophenyl)-methoxy)-imino)-acetamido)- 2-carboxy-8-oxo-5-thia-1-azabicyclo[4,2,0]oct- 2-en-3-yl)-2-propenyl)-quinolinium, the internal salt of [6R-[3(E), 6α,7β(Z)]]-1-[3-[7-[[(2-amino- 4-thiazolyl) [carboxy-(2-chloro-3,4-dihydroxy-phenyl)-methoxy]-imino]-acetamido]- 2-carboxy-8-oxo-5-thia-1-azabicyclo[4,2,0]oct- 2-en-3-yl]-2-propenyl]-quinolinium (R) or (S) or an (R+S) mixture, the internal salt of [6R-[3(E), 6α,7β(Z)]]-1-[3-[7-[[( 2-amino-4-thiazolyl) [carboxy-(3-cyano-4,5-dihydroxy-phenyl)-methoxy]-imino]-acetamido]- 2-carboxy-8-oxo-5-thia-1-azabicyclo[4,2,0]oct- 2-en-3-yl]-2-propenyl]-quinolinium (R) or (S) or an (R+S) mixture, the internal salt of [6R-[3(E), 6α,7β(Z)]]-1-[3-[7-[ [(2-amino-4-thiazolyl) (carboxy-(3-fluoro-4,5-dihydroxy-phenyl)-methoxy]-imino]-acetamido)- 2-carboxy-8-oxo-5-thia-1-azabicyclo[4,2,0]oct- 2-en-3-yl]-2-propenyl]-quinolinium (R) or (S) or an (R+S) mixture, the internal salt of [6R-[3(E), 6α,7β(Z)]]-2-[3-[7-[[ (2-amino-4-thiazolyl) [carboxy-(2,5-dichloro-3,4-dihydroxy-phenyl)-methoxy]-imino]-acetamido]- 2-carboxy-8-oxo-5-thia-1-azabicyclo [4,2,0]oct-2-en-3-yl]-2-propenyl]-quinolinium (R) or (S) or an (R+S) mixture, the internal salt of [6R-[3(E), 6α,7β(Z)]]-1-[3-[7-[[( 2-amino-4-thiazolyl) (carboxy-(2,5-dichloro-3,4-dihydroxy-phenyl)-methoxy]-imino]-acetamido]- 2-carboxy-8-oxo-5-thia-1-azabicyclo[4,2,0]oct- 2-en-3-yl]-2-propenyl]-thieno[2,3-b]pyridinium (R) or (S) or an (R+S) mixture, the internal salt of [6R-[3(E), 6α,7β[Z(S*) ]]]-1-[3-[7-[[ (2-amino-4-thiazolyl) [carboxy-(3-cyano-4,5-dihydrophenyl)-methoxy]-imino]-acetamido]- 2-carboxy-8-oxo-5-thia-1-azabicyclo [4,2 0]-oct- 2-en-3-yl]-2-propenyl]-thieno [2,3-b]pyridinium, the internal salt of [6R-[3(E), 6α, 7β(Z)]]-3-1-[3[-7-[[(2-amino- 4-thiazolyl) [carboxy-2,5-dichloro-3,4-dihydroxyphenyl)-methoxy]-imino]-acetamido]- 2-carboxy-8-oxo-5-thia-1-azabicyclo[4,2,0]oct- 2-en-3-yl]-2-propenyl]-isoquinolinium (R) or (S) or an (R+S) mixture and the internal salt of [6R-[3(E), 6α,7β(Z)]]-1-[3-[7-[[ (2-amino-4-thiazolyl) [carboxy-(2,5-dichloro-3,4-dihydroxy-phenyl)-methoxy]-imino]-acetamido]- 2-carboxy-8-oxo-5-thia-1-azabicyclo[4,2,0]oct- 2-en-3-yl]-2-propenyl]-4-(methylthio)-pyridinium (R) or (S) or an (R+S) mixture.

The novel process of the invention for the preparation of a compound of formula I comprises reacting a compound of the formula

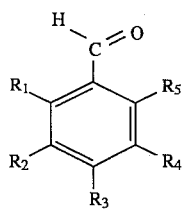

in which $R_1$, $R_2$, $R_3$, $R_4$ and $R_5$ are as defined above optionally with necessary protection of its reactive functions to form an aromatic aldehyde of formula $II_p$:

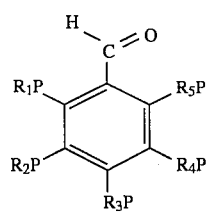

in which $R_{1p}$, $R_{2p}$, $R_{3p}$, $R_{4p}$ and $R_{5p}$ represent $R_1$, $R_2$, $R_3$, $R_4$ and $R_5$ as defined previously or a protected reactive function, the latter is homologated into an α-hydroxy acid of the formula

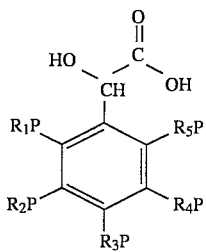
III esterifing the latter to form an α-hydroxy ester of the formula

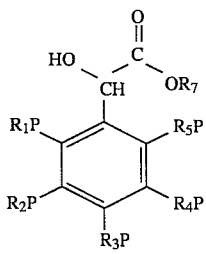
IV wherein $R_7$ is the remainder of an easily-cleavable ester, reacting the latter with N-hydroxy phthalimide to obtain a compound of the formula

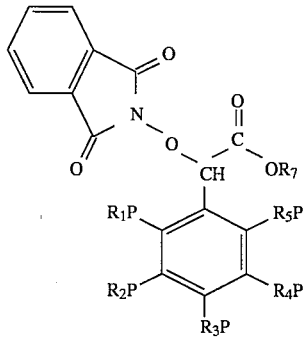
V reducing the latter to form an O-substituted hydroxylamine of the formula

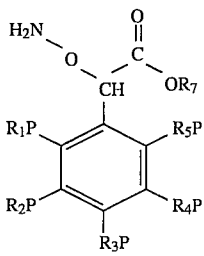
VI condensing the latter with a derivative of (2-amino-thiazolyl)-glyoxylic acid of the formula

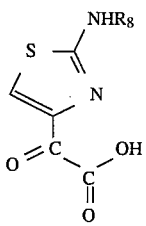
VII wherin $R_8$ is hydrogen or a protective group of the amine function to form a compound of the formula

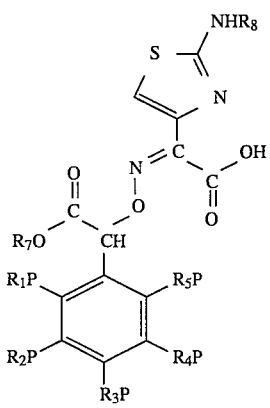
VIII amidifying the latter with an ester of 7-amino-3-(3-chloro-1-propenyl)-8-oxo-5-thia-1-azabicyclo[4,2,0]oct-2-en-2-carboxylic acid hydrochloride of the formula

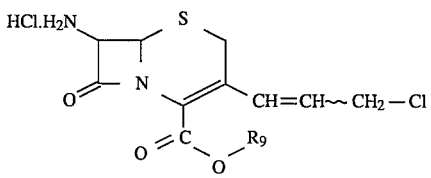
IX or its salts wherein $R_9$ is the remainder of an easily-cleavable ester to obtain a compound of the formula

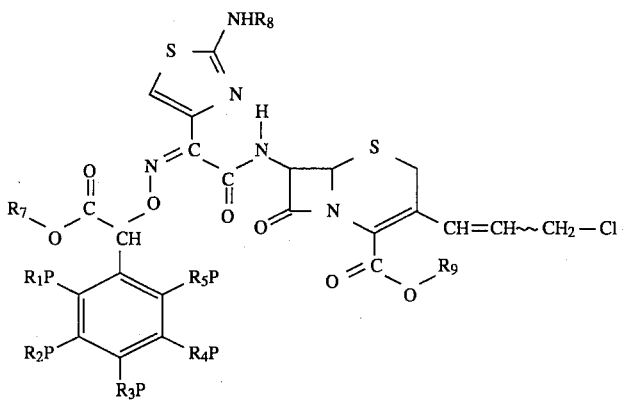

X converting the latter into an 3-(3-iodo-propenyl) of the formula

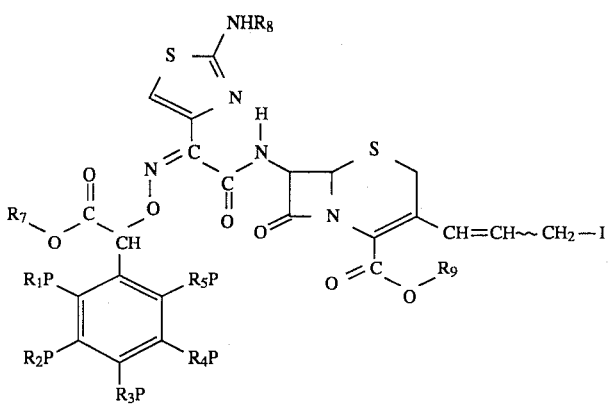

XI treating the latter with a base of $R_6$ to obtain a compound of the formula

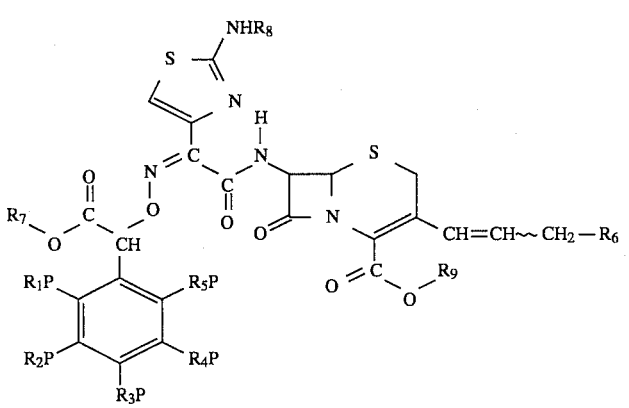

XII optionally separating the (E) or (Z) isomers or the (Z) isomers are converted into (E) isomers and subjecting the compound of formula XII to one or more of the following reactions in any order:

a) cutting by hydrolysis or by the action of thiourea of all or part of the ester groups or the protective groups of the amino or hydroxy, b) esterification or salification of the carboxylic by a base, c) salification of amino by an acid, d) separation of the products in the form of an R,S mixture into R or S.

In a variant of the process, the O— substituted hydroxylamine of formula VI is condensed with a compound of the formula

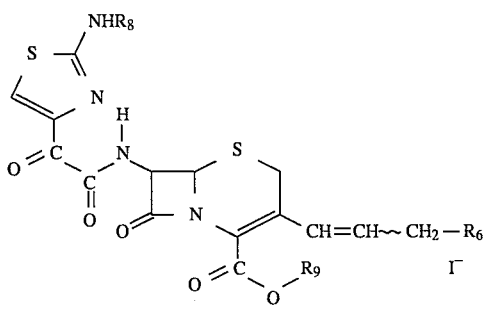

to obtain the product of formula XII as defined previously.

The protected hydroxy functions of $R_{1p}$, $R_{2p}$, $R_{2p}$, $R_{4p}$ and $R_{5p}$ are chosen from acyloxy groups such as formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy. Other groups include ethoxycarbonyloxy, methoxycarbonyloxy, propoxycarbonyloxy, 2,2,2-trichloro ethoxycarbonyloxy, benzyloxycarbonyloxy, tert.-butoxycarbonyloxy, 1-cyclopropyl ethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tertbutyl benzoyloxy, capryloyloxy, acryloyloxy, methylcarbamoyloxy, phenylcarbamoyloxy, naphthylcarbamoyloxy.

Other protective groups are phenoxy, 4-chloro phenoxy, tolyloxy or tert.-butyl phenoxy, tetrahydropyrannyloxy, tetrahydrothiopyrannyloxy, methoxytetrahydropyrannyloxy, trityloxy, benzyloxy, 4-methoxy benzyloxy, benzhydryloxy, trichloroethoxy, 1-methyl-1-methoxyethoxy, or alkoxy alkoxy-methyl such as methoxy ethoxy methyl.

Two adjacent hydroxyls can be protected by forming a methylenedioxy, isopropylenedioxy, 1,1-cyclohexyl bis(oxy), diphenylmethylenedioxy, carbonate or hydroxy borannylbis(oxy).

The protected hydroxy functions of $R_{1p}$, $R_{2p}$, $R_{3p}$, $R_{4p}$ and $R_{5p}$, are preferably chosen from methoxyethoxymethoxy, propionyloxymethoxy, acetoxymethoxy, butoxy, isobutoxy, tert.-butoxy, pentoxy, hexyloxy, butyryloxymethoxy, valeryloxymethoxy, pivaloyloxymethoxy, 2-acetoxy ethoxy, 2-propionyloxy ethoxy, 1-butyryloxy ethoxy, 2-iodoethoxy, 2,2,2-trichloro ethoxy, vinyloxy, allyloxy, ethynyloxy, propynyloxy, benzyloxy, 4-methoxy, benzyloxy, 4-nitro benzyloxy, phenylethoxy, trityloxy, diphenylmethyloxy or 3,4-dimethoxyphenoxy. The 2-methoxy ethoxymethoxy (MEM-O) group is particulary preferred.

The remainders of the easily-cleavable ester groups of $R_7$ and $R_9$ are chosen from butyl, isobutyl, tert.-butyl, pentyl, hexyl, methoxymethyl, ethoxymethyl, isopropoxymethyl, α-methoxy ethyl, α-ethoxy ethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert.-butylcarbonyloxymethyl, hexadecanoyloxymethyl, pivaloyloxymethyl, propionyloxyethyl, isovaleryloxyethyl, 1-acetoxy ethyl, 2-acetoxy ethyl, 1-propionyloxy ethyl, 2-propionyloxy ethyl, 1-butyryloxy ethyl, 2-butyryloxy ethyl, 1-(tert.-butyloxycarbonyloxy) ethyl, 1-acetoxy propyl, 1-hexadecanoyloxy ethyl, 1-propionyloxy propyl, 1-methoxycarbonyloxy ethyl, methoxycarbonyloxymethyl, 1-acetoxy butyl, 1-acetoxy hexyl, 1-acetoxy heptyl, phthalidyl, 5,6-dimethoxy phthalidyl, tert-butylcarbonylmethyl, vinyl, allyl, 2-chloro allyl, ethynyl, propynyl, methoxycarbonylmethyl, benzyl, 4-methoxy benzyl, 4-nitro benzyl, phenethyl, trityl, diphenyl methyl, phenyl, 4-chloro phenyl, tolyl, tert.-butyl phenyl, 3,4-dimethoxy phenyl, methoxyethoxymethyl, dimethylaminoethyl, cyanomethyl, tert-butoxycarbonylmethyl, 2,2-ethylenedioxy ethyl, cyanoethyl 2,2-dimethoxy ethyl; 2-chloro ethoxymethyl, (2-hydroxy ethoxy) ethyl, 2,3-epoxy propyl 3-dimethylamino 2-hydroxy propyl, 2-hydroxy ethyl, 2-methylaminoethoxymethyl, (2-amino ethoxy) methyl, 3-methoxy 2,4-thiadiazol-5-yl, tetrahydropyrann-2-yl, 1-methoxy 1-methyl ethyl, 2-hydroxy 1-methyl ethyl, isopropyl, carbamoylmethyl, chloromethyl, 2-chloro ethyl, 2,2,2-trichloro ethyl, 2-iodo ethyl, acetyl, methyl, 2-methylthio ethyl, thiocyanatomethyl, 2-chloro-1-acetoxy ethyl, 2-bromo 1-acetoxy ethyl, 2-fluoro 1-acetoxy ethyl, 2-methoxy 1-acetoxy ethyl, 2-methyl 1-acetoxy propyl, 1-methyl 1-acetoxy ethyl, 1-(methoxyacetoxy) ethyl, 1-acetyl carbonyloxyethyl, 1-hydroxy acetoxyethyl, 1-(2-thienyl)carbonyloxyethyl, 1-(2-furyl) carbonyloxyethyl, 1-(5-nitro-2-furyl) carbonyloxy-ethyl, 1-(2-pyrrolyl) carbonyloxyethyl, 1-(propionyloxycarbonyloxy) ethyl, 1-(propoxycarbonyloxy) ethyl, 1-(isopropoxcarbonyloxy) ethyl, 1-(methoxyethoxy-carbonyloxy) ethyl, 1-(allyloxy-carbonyloxy) ethyl, isopropoxycarbonyl methyl, 1-[(2,3-epoxy propyl) oxycarbonyloxy]ethyl, 1-[(2-furyl) methoxycarbonyloxy ethyl, 1-[(2-fluoro ethoxy)carbonyloxy]ethyl, 1-(methoxy-carbonyloxy) propyl, 1-(methoxycarbonyloxy) 1-methyl ethyl, (methoxycarbonyloxy) chloromethyl, 1-(methoxycarbonyl-oxy)-2-chloro ethyl, 1-(methoxy carbonyloxy) 2-methoxy ethyl, 1-(methoxycarbonyloxy) allyl or a 5-methyl 2-oxo 1,3-dioxol-4-yl remainder.

Diphenylmethyl is preferred for $R_7$ and 4-benzyl methoxy or diphenylmethyl are preferred for $R_9$.

The protective group of the amino of $R_8$ can be for example carbamoyl, methyl carbamoyl, phenylcarbamoyl, naphthylcarbamoyl, as well as the corresponding thiocarbamoyls, alkyl of 1 to 6 carbon atoms substituted or non-substituted, such as preferably, trichloroethyl, tert.-butyl or tert-amyl, aralkyl such as benzyl, 4-methoxy benzyl, phenethyl, trityl, 3,4-dimethoxy benzyl or benzhydryl, a substituted or non-substituted aliphatic, aromatic or heterocyclic acyl such as formyl, acetyl, propionyl, butyryl, isobutyryl, valeryl, isovaleryl, chloroacetyl, dichloroacetyl, trichloroacetyl, bromoacetyl, trifluoroacetyl benzoyl, toluolyl, naphthoyl, chlorobenzoyl, para-nitro benzoyl, para-tert-butyl benzoyl, phenoxyacetyl, caprylyl, decanoyl, acryloyl, phthaloyl, mesyl, phenyl-acetyl, phenylpropionyl, oxalyl, succinyl, pivaloyl, lower alkoxycarbonyl or cycloalkoxycarbonyl such as methoxycarbonyl, ethoxycarbonyl, propoxycarbonyl, 1-cyclopropylethoxycarbonyl, isopropoxycarbonyl, butoxycarbonyl, tert-butoxycarbonyl, pentoxycarbonyl, hexyloxycarbonyl, trichloroethoxy carbonyl, aralkoxycarbonyl such as benzyloxycarbonyl. The trityl is preferred.

The above list is not limitative and it is evident that other amine protective groups, groups known in particular in the chemistry of the peptides, can also be used.

The functional derivative of the acid of formula VIII may be for example a halide, a symmetrical or mixed anhydride, amide, azide or an activated ester. An example of a mixed anhydride is that formed with isobutyl chloroformate or that formed with pivaloyl chloride and the carboxylic-sulfonic mixed anhydrides formed for example with p-toluene sulfonyl chloride.

An example of an activated ester is the ester formed with 2,4-dinitrophenol or that formed with hydroxybenzothiazole. An example of a halide is the chloride or bromide.

The anhydride can be formed in situ by the action of N,N'-disubstituted carbodiimide, for example, N,N-dicyclohexylcarbodiimide. The acylation reaction is preferably carried out in an organic solvent such as methylene chloride but other solvents can be used such as tetrahydrofuran, chloroform or dimethylformamide.

When an acid halide is used and in a general manner when a hydrohalic acid molecule is released during the reaction, the reaction is preferably carried out in the presence of a base such as sodium hydroxide, potassium hydroxide, sodium or potassium carbonates and bicarbonates, sodium acetate, triethylamine, pyridine, morpholine or N-methylmorpholine. The reaction temperature is generally lower than or equal to ambient temperature.

A product of formula VIII can also be reacted directly with a product of formula IX in the presence of a carbodiimide such as diisopropylcarbodiimide or 1-(3-dimethylamino propyl)-3-ethyl carbodiimide (EDC).

The action of the reagent capable of introducing $R_6$ into the product of formula IV is carried out under the following conditions: When Hal is chlorine, a substitution of chlorine by iodine in the presence of sodium iodide can be carried out in situ or separately, then the desired reagent is added in the optional presence of an organic solvent such as dichloromethane, acetonitrile or tetrahydrofuran. The desired reagent of $R_6$ can also be reacted directly on the product of formula X in the presence of silver tetrafluoroborate.

The isomerism of the products of formula XII can be different from that of the products of formula X or XI used at the start. When the Z isomer is isolated, this isomer can be converted into the E isomer by the usual methods, notably by the action of iodine.

Depending upon $R_7$, $R_8$, $R_9$, $R_{1p}$, $R_{2p}$, $R_{3p}$, $R_{4p}$ and $R_{5p}$, the action of one or more of hydrolysis, hydrogenolysis agents or of thiourea on the product of formula XII is intended to eliminate $R_8$ when the latter is a protective group of the amino to convert $R_{1p}$, $R_{2p}$, $R_{3p}$, $R_{4p}$ and $R_{5p}$ into $R_1$, $R_2$, $R_3$, $R_4$ and $R_5$ respectively when these are a protective group of hydroxyls and/or to eliminate $R_7$ and $R_9$ when these are easily-cleavable ester groups, one of those that it is desired to eliminate.

It is possible to eliminate $R_8$ and to convert $R_{1p}$, $R_{2p}$, $R_{3p}$, $R_{4p}$ and $R_{5p}$ into $R_1$, $R_2$, $R_3$, $R_4$ and $R_5$ respectively when these are a protective group of hyroxyls without affecting $R_7$ and $R_9$ when these have to be preserved. The nature of the reagents to be used in such a case is well known to one skilled in the art. Examples of such reactions are given further on in the experimental part. A description of the methods for eliminating the different protective groups will be found in French Patent Application No. 2,499,995.

Given the nature of the preferred protective groups used: trityl for $R_8$, 2-methoxyethoxymethyl to protect hydroxy functions of $R_1$, $R_2$, $R_3$, $R_4$ and $R_5$, diphenylmethyl for $R_7$ and 4-methoxy benzyl or diphenylmethyl for $R_9$, trifluoroacetic acid is preferably used without a solvent or in a solvent such as anisole or a mixture of solvents such as anisole/methylene chloride. A salt is then obtained with trifluoroacetic acid and the free base can be obtained by the action of a base such as triethylamine carbonate.

The salification of the products can be carried out by the usual methods. For example, by the action, on a product in the acid form or on a solvate, for example the ethanolic solvate or a hydrate of this acid, of a mineral base such as sodium or potassium hydroxide, sodium or potassium carbonate or bicarbonate. Mineral acid salts such as trisodium phosphate can also be used. Organic acid salts can also be used such as, for example, sodium salts of saturated or unsaturated, linear or branched aliphatic carboxylic acids of 1 to 18 and preferably 2 to 10 carbon atoms. The aliphatic chains of these acids can be interrupted by one or more heteroatoms such as oxygen or sulfur or substituted by aryl such as phenyl, thienyl or furyl, by one or more hydroxyl or by one or more halogens such as fluorine, chlorine or bromine, preferably chlorine, by one or more lower carboxylic or alkoxycarbonyl, preferably methoxycarbonyl, ethoxycarbonyl or propyloxycarbonyl, by one or more aryloxy, preferably phenoxy.

Moreover, sufficiently soluble aromatic acids can be used as the organic acids such as benzoic acid substituted preferably by lower alkyl.

Examples of such organic acids are formic acid, acetic acid, acrylic acid, butyric acid, adipic acid, isobutyric acid, n-caproic acid, isocaproic acid, chloropropionic acid, crotonic acid, phenyl acetic, (2-thienyl) acetic acid, (3-thienyl) acetic acid, (4-ethyl phenyl) acid, acetic acid, glutaric acid, monoethylic ester of adipic acid, hexanoic acid, heptanoic, acid, decanoic acid, oleic acid, stearic acid, palmitic acid, 3-hydroxy propionic acid, 3-methoxy propionic acid, 3-methylthio butyric acid, 4-chloro butyric acid, 4-phenyl butyric acid, 3-phenoxy butyric acid, 4-ethyl benzoic acid, 1-propyl benzoic acid.

Sodium acetate, sodium 2-ethyl hexanoate or sodium diethyl acetate are preferably used as sodium salts.

The salification can also be obtained by the action of an organic base such as triethylamine, diethylamine, trimethylamine, propylamine, N,N-dimethylethanolamine, tris[(hydroxymethyl)-amino]methane, methylamine, ethanolamine, pyridine, picoline, dicyclohexyl amine, morpholine and benzylamine or by the action of arginine, lysine, procaine, histidine, N-methyl glucamine. This salification is preferably carried out in a solvent or a mixture of solvents such as water, ethyl ether, methanol, ethanol or acetone.

The salts are obtained in amorphous or crystallized form according to the reaction conditions used. The crystallized salts are preferably prepared by reacting the free acids with one of the salts of the aliphatic carboxylic acids mentioned above, preferably with sodium acetate. The salification of the products by mineral or organic acids is carried out under the usual conditions.

The optional esterification of the proucts is carried out under standard conditions. The operation is generally carried out by reacting the acid of formula I or a functional derivative of the acid with a derivative of the formula Z—Re wherein Z is hydroxyl or halogen such as chlorine, bromine, iodine and Re is the ester group to be introduced, a non-exhaustive list of which group is given above. In certain cases, it may be advantageous to carry out an esterification on a product of which the amine and/or reactive groups present on the oxyimino are blocked before removing the protective group of the amine and of the reactive group present on the oxyimino.

The products of formula I contain several asymmetrical carbons. In the cephem nucleus which contains two asymmetrical carbons, the two carbons are in R configuration. Furthermore, the substituent present on the oxyimino function also contains an asymmetrical carbon which can be in R or S form or in the form of an R+S mixture. The separation of the two diastereoisomers can be carried out by means known to one skilled in the art, for example by chromatography.

The antibacterial compositions of the invention are comprised of an antibactericidally effective amount of at least one compound of formula I or its non-toxic, pharmaceutically acceptable acid addition salts and an inert pharmaceutical carrier. The compositions may be in the form of tablets, dragees, capsules, granules, suppositories, ointments, creams, gels and injectable solutions.

Examples of inert pharmaceutical carriers are talc, arabic gum, lactose, starch, magnesium stearate, cocoa butter, aqueous or non-aqueous vehicles, fatty derivatives of animal or vegetable origin, paraffin derivatives, glycols, various wetting agents, dispersants and emulsifiers and preservatives.

The compositions have a very good antibiotic activity on gram (+) bacteria such as staphylococci, streptococci and notably on penicillin-resistant staphylococci. Their effectiveness on gram (–) bacteria, particularly on coliform bacteria, klebsiella, salmonella, proteus and pseudomonas, is particularly remarkable.

These properties make the compositions suitable for use as medicaments in the treatment of germ-sensitive diseases and particularly in that of staphylococci, such as staphylococci septicemias, malignant staphylococcia of the face or skin, pyodermititis, septic or suppurative sores, anthrax, phlegmon, erysipelas, acute primary or post-influenzal staphylococcia, bronocho-pneumonia, pulmonary suppurations. These compositions can also be used as medicaments in the treatment of colibacilloses and associated infections, of proteus, klebsiella and salmonella infections and of other diseases caused by gram (–) bacteria.

The compositions wherein A is a cleavable ester are preferred for oral administration and when in the form of a powder, the compositions are dissolved extemporaneously in a vehicle such as apyrogenic water.

The novel method of combatting bacterial infections in warm-blooded animals, including humans, comprises administering to warm-blooded animals an antibacterially effective amount of at least one compound of formula I or its non-toxic, pharmaceutically acceptable acid addition salts. The compounds may be administered orally, rectally, parenterally or topically on skin and mucous membranes. The usual daily dose is 3.33 to 53.3 mg/kg depending on the condition treated, specific compound used and the method of administration. The method can also be used for disinfecting surgical instruments.

The novel intermediates of the invention are those compounds of formulae III, IV, V, VI, VIII, X, XI, XII and XIII.

The compound of formula VI in which $R_{1p}$ and $R_{2p}$ are fluorine and $R_{3p}$ and $R_{4p}$ are a hydroxy protected by a methoxyethoxymethyl (M.E.M.) (hereafter) product of formula $VI_A$ may be prepared by reacting a compound of the formula

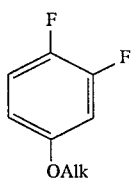

A wherein Alk is alkyl, preferably methyl, with butyllithium and trimethylborate and then oxygenated water to obtain a compound of the formula

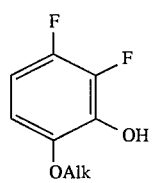

B reacting the latter with dimethylamine in the presence of formic anhydride to obtain a compound of the formula

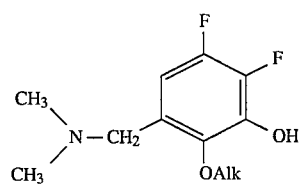

C reacting the latter with methyl iodide and hexamethylenetetramine in the presence of acetic acid to obtain a compound of the formula

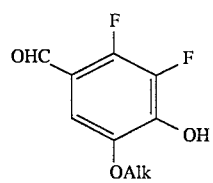

$II_D$ reacting the latter to eliminate the alkyl in the presence of borontribromine to obtain the compound of the formula

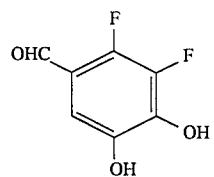

E reacting the latter with a protecting agent to protect the hydroxyl function by a MEM group for example to obtain a compound of the formula

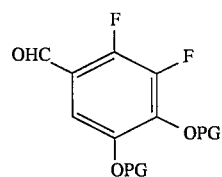

F wherein PG represents a protective group of the hydroxyls, reacting the latter with a organophosphorated derivative of the formula

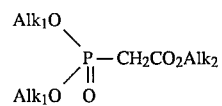

wherein $Alk_1$ and $Alk_2$ are individually alkyl of 1 to 4 carbon atom to obtain a compound of the formula

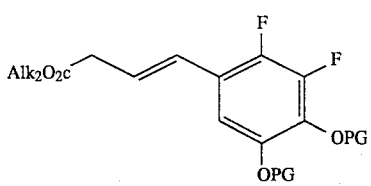

G reacting the latter with a reducing agent i.e. diisobutyl-aluminium hydride to obtain a compound of the formula

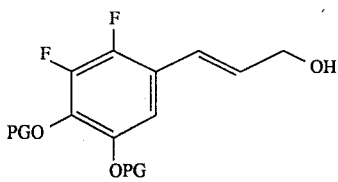

H reacting the latter with an epoxidation reagent, i.e. with m-chloroperbenzoic acid to obtain a compound of the formula

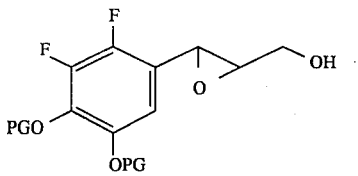

J reacting the latter with cuprous chloride in the presence of lithium chloride to obtain a compound of the formula

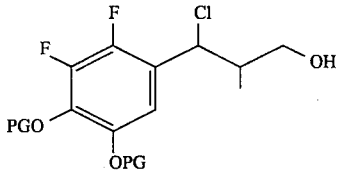

K reacting the latter with an oxidation reagent i.e. sodium metaperiodate then with an esterifying reagent to obtain a compound of the formula

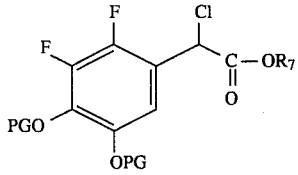

L wherein $R_7$ has the above definition and reacting the latter with N-hydroxyphthalimide to obtain a compound of the formula

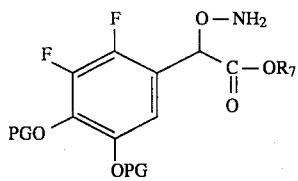

VI$_a$

The manner and most are commercially available. Others can be prepared from commercially-available products by the methods described in the preparations below for the preparation of the compound of formula II. The methods described in the literature can also be used, notably the so-called Rosemund reduction, the reduction of benzoic acid or the formylation of aromatic rings such as the Vilsmeier-Haack reaction, the Gatterman-Koch reaction, the Reimer-Tiemann reaction or the reaction with formyl fluoride (J. Am. Chem. Soc., Vol. 82, p. 2380 (1960)).

The products of formulae VII and IX are also knwon in the literature, notably in Belgian Patent Application No. 864,828 and European Patent Application EP 0,333,154.

In the following examples, there are described several preferred embodiments to illustrate the invention. However, it should be understood that the invention is not intended to be limited to the specific embodiments.

PREPARATION 1

2-chloro-3,4-bis[(2-methoy-ethoxy)-methoxy]-benzaldehyde

STEP A: 2-chloro-3,4-dihydroxy benzaldehyde 27.62 g of 3,4-dihydroxy benzaldehyde (commercial) were dissolved in 450 ml of acetic acid and chlorine was bubbled through the solution at an ordinary temperature until 4.48 ml of the gas had been consumed. The mixture was stirred for 16 hours and then the solution was concentrated and cooled to 0° C. The precipitate was filtered, washed and dried to obtain 7.5 g of the expected product which after it was crystallized from ethyl acetate melted at 196° C.

STEP B: 2-chloro-3,4-bis[(2-methoxy-ethoxy)-methoxy]-benzaldehyde 46 ml of diisopropyl ethylamine were added to a suspension of 11.42 g of the product of Step A in 120 ml of methylene chloride and the mixture was cooled to −10° C. Then, 30.14 ml of chloro-( 2-methoxy-ethoxy)-methane were added and the mixture was stirred for one hour. The mixture was diluted with 100 ml of water, separated and then the organic phase was washed, dried and concentrated to obtain 22.6 g of the expected product with a Rf=0.6 (eluant: ethyl acetate).

NMR analysis of the proton (CDCl$_3$ 250 MHz in ppm): 3.36 (s), and 3.38 (s): —OCH$_3$ 3.58 (m) (4H), 3.84 (m) (2H) and 4.06 (m) (2H): —O——CH$_2$—CH$_2$—O 5.29 (s) (2H) and 5.38 (s) (2H): —O—CH$_2$—O 7.21 (d) and 7.71 (d): aromatic protons (Ar—H) 10.36 (s): —CH=O.

PREPARATION 2

3-formyl-5,6-bis[(2-methoxy-ethoxy)-methoxy]-benzonitrile

STEP A: 3-formyl-6-hydroxy-5-methoxy benzonitrile

A mixture of 23.1 g of 3-bromo-4-hydroxy-5-methoxy benzaldehyde, 9.3 g of cuprous cyanide and 140 ml of dimethyl acetamide (DMA) was refluxed for 2 hours with stirring. After cooling, the mixture was poured over ice and extracted with an ethyl acetate-methanol mixture (90-10). The organic phase was washed and dried and the solvents were eliminated to obtain 18 g of crude product which was used as is for the following step. It melted at 180° C.

STEP B: 3-formyl-5,6-dihydroxy benzonitrile 18 g of the product of Step A and 400 ml of dichloromethane were mixed together under nitrogen and the mixture was cooled to 0° C. 150 ml of a molar solution of boron tribromide in dichloromethane were added and the mixture stood for one night at ambient temperature. It was concentrated, cooled again to 0° C. and 250 ml of a normal solution of hydrochloric acid were added. The crystallized product was separated out, washed with water, dried then crystallized from an isopropanol-water mixture (1-2) to obtain 12 g of the expected product.

Infrared analysis (Nujol):

Strong and complex absorption in the —NH/OH region 2245 cm$^{-1}$: C≡N 1700 cm$^{-1}$: C=O 1602, 1597 1520 cm$^{-1}$: aromatic nucleus NMR analysis of the proton (DMSO 250 MHz in ppm);
7.45 (d) (J=2): Ar—H 7.73 (d) (J=2): Ar—H 9.74: CH=O 11.15: mobile absorption STEP C: 3-formyl-5,6-bis[(2-methoxy-ethoxy)-methoxy]-benzonitrile 53.6 ml of diisopropyl ethylamine were added to a suspension of 12.6 g of the product of Step B in 500 ml of dichloromethane and the mixture was cooled to −10° C. Then 35.3 ml of chloro-( 2-methoxy-ethoxy)-methane were added and the mixture was stirred for one hour. The medium was diluted with 100 ml of water, separated and then the organic phase was washed, dried and concentrated to obtain 21.4 g of the expected product.

Infrared analysis (CHCl$_3$):

Absence of OH 2235 cm$^{-1}$: C≡N 1702 and 2730 cm$^{-1}$: CH=O 1592, 1582 and 1485 cm$^{-1}$: aromatic nucleus NMR analysis of the proton (CDCl$_3$ 250 MHz in ppm):
3.37 (s): —OCH$_3$ 3.58 (m) (4H), 3.85 (m) (2H) and 4.06 (m) (2H): 0—CH$_2$—CH$_2$—O 5.39 (s) (2H) and 5.49 (s) (2H): —O—CH$_2$—O 7.76 (d) (1H) and 7.92 (d) (1H): Ar—H 9.90 (s): —CH=O

PREPARATION 3

3-fluoro-4,5-bis[(2-methoxy-ethoxy)-methoxy]benzaldehyde

STEP A: 3-fluoro-4-hydroxy-5-methoxy benzaldehyde

A mixture of nitrogen containing 10% of fluorine was bubbled for two and a half hours through a mixture of 30.4 g of 4-hydroxy-5-methoxy benzaldehyde (vanillin), 100 ml of acetonitrile and 250 ml of Freon at 0° C. under nitrogen. After treatment with thiosulfate, acidification with a solution of 2N hydrochloric acid and extraction with ethyl acetate, the organic phase was washed, dried, concentrated and chromatographed on silica eluting with dichloromethane to obtain 2.1 g of the desired product with a Rf=0.3.

| Analysis: C$_7$H$_7$OF$_3$ | | | | | | |
|---|---|---|---|---|---|---|
| Calculated: | % C | 56.47 | % H | 4.14 | % F | 11.16 |
| Found: | | 56.4 | | 4.1 | | 11.0 |

STEP B: 3-fluoro-4,5-dihydroxy benzaldehyde 3.72 g of the product of Step A and 60 ml of dichloromethane were mixed together under nitrogen and the mixture was cooled to 0° C. 32 ml of a molar solution of boron tribromide in dichloromethane were added and the mixture stood for one hour at ambient temperature and then was concentrated, cooled again to 0° C. and acidified. The crystallized product was separated out, washed with water and dried to obtain 2.83 g of the expected crude product which is used as is for the following step. It had a Rf=0.2 [eluant: acetone-dichloromethane (1-9)].

STEP C: 3-fluoro-4,5-bis[(2-methoxy-ethoxy)-methoxy] benzaldehyde 17 ml of diisopropyl ethylamine were added to a suspension of 2.8 g of the product of Step B in 5.6 ml of dichloromethane. The mixture was cooled to 10° C. and then 6.5 ml of chloro-( 2-methoxy-ethoxy)-methane were added. The mixture was stirred for one hour and was then diluted with 100 ml of water and separated. Then, the organic phase was washed, dried and concentrated to obtain 5.5 g of the expected product with a Rf=0.55 [eluant: dichloromethane-acetone (9-1)].

Infrared analysis (CHCl$_3$):

Absence of OH 1696 and 2730 cm$^{-1}$: conjugated CH=O

NMR analysis of the proton (CDCl$_3$ 200 MHz in ppm):
3.36 (s) and 3.37 (s): —OCH$_3$ 3.60 (m) (4H), 3.85 (m) (2H) and 3.96 (m) (2H): O—CH$_2$—CH$_2$—O 5.33 (s) and 5.36 (s): O—CH$_2$—O 7.32 (dd) 7.51 (m): Ar—H 9.90(m): —CH=O

PREPARATION 4

3-chloro-4,5-bis[(2-methoxy-ethoxy)-methoxy]-benzaldehyde

STEP A: 3-chloro-4,5-dihydroxy benzaldehyde 37.2 g of commercial 5-chloro vanillin and 800 ml of dichloromethane were mixed together under nitrogen and cooled to 0° C. 300 ml of a molar solution of boron tribromide in dichloromethane were added and the mixture stood for one night at ambient temperature. It was concentrated, cooled again to 0° C. and acidified. The crystallized product was separated, washed with water, dried and crystallized from an isopropanol-water mixture (1-2 by volume) to obtain 26.6 g of the expected product melting at >260° C.

Infrared analysis (Nujol):

3425 cm$^{-1}$: —OH+general absorption 1672–1660 cm$^{-1}$: C=O 1595, 1588, 1534, 1500 cm$^{-1}$: aromatic ring NMR analysis of the proton (DMSO 250 MHz in ppm):
7.24 (d J=2Hz) and 7.44 (d J=2Hz): Ar—H 9.90 (m): —CH=O 10.40: mobile absorption STEP B: 3-chloro-4,5-bis[(2-methoxy-ethoxy)-methoxy] benzaldehyde 60.5 ml of diisopropyl ethylamine were added to a suspension of 15 g of the product of Step A in 150 ml of dichloromethane and the mixture was cooled to −10° C. Then, 39.7 ml of chloro-( 2-methoxy-ethoxy)-methane were added over 45 minutes and the mixture was stirred for half an hour and diluted with 100 ml of water and separated. Then, the organic phase was washed, dried, concentrated and chromatographed on silica, eluting with a dichloromethane-methanol mixture (99-1) to obtain 15.9 g of the expected product.

Infrared analysis (CHCl$_3$):

1698 and 2735 cm$^{-1}$: conjugated CH=O 1591, 1579, 1498 cm$^{-1}$: aromatic ring NMR analysis of the proton (CDCl$_3$ 250 MHz in ppm):
3.38 (s): —OCH$_3$ 3.57 (m) (4H), 3.87 (m) (2H) and 4.03 (m) (2H): O—CH$_2$—CH$_2$—O 5.36 (s) and 5.38 (s): O—CH$_2$—O 7.59 (d) 7.62 (d): Ar—H 9.85: —CH=O

PREPARATION 5

3-nitro-4,5-bis[(2-methoxy-ethoxy)-methoxy]benzaldehyde

STEP A: 3-nitro-4,5-dihydroxy benzaldehyde 35 g of 5-nitro vanillin (commercial) and 1200 ml of dichloromethane were mixed together under nitrogen and the mixture was cooled to 0° C. 533 ml of a molar solution of boron tribromide in dichloromethane were added and the mixture stood for 2 days at abmient temperature and then was concentrated. The residue was taken up cold (ice bath+methanol) in 300 ml of 2N hydrochloric acid and the mixture was stirred for two to three hours at this temperature, then left for 16 hours at ambient temperature. Extraction was carried out with ethyl acetate and the organic phase was washed, dried and concentrated to obtain 18 g of the expected product melting at >260° C.

Infrared analysis (Nujol):
general absorption NH/OH 1682 cm$^{-1}$: C=O 1620, 1590, 1580, 1548 and 1525 cm$^{-1}$: aromatic ring+—NH$_2$ STEP B: 3-nitro-4,5-bis[(2-methoxy-ethoxy)-methoxy]benzaldehyde 13.6 ml of diisopropyl ethylamine were added to a suspension of 18 g of the product of Step A in 50 ml of dichloromethane and the mixture was cooled. Then, 39.6 ml of chloro-( 2-methoxy-ethoxy)-methane were added over 45 minutes and was then stirred for two hours at 0° C. and diluted with 100 ml of water and separated. The organic phase was washed, dried, concentrated and chromatographed on silica, eluting with a dichloromethane-acetone mixture (9-1) to obtain 22.1 g of the expected product with a Rf=0.3.

Infrared analysis (CHCl$_3$):
1704 cm$^{-1}$: CH=O 1608, 1578, 1546, 1496 cm$^{-1}$: aromatic ring+—NO$_2$ NMR analysis of the proton (CDCl$_3$ 300 MHz in ppm):
3.36 and 3.38: —OCH$_3$ 3.55 (m), 3.87 (m): O—CH$_2$—CH$_2$—O 5.41: O—CH$_3$—O 7.92: Ar—H 9.93:—CM=O

PREPARATION 6

3-iodo-4,5-bis[(2-methoxy-ethoxy)-methoxy]benzaldehyde
STEP A: 3-iodo-4,5-dihydroxy benzaldehyde 37.2 g of 5-iodo vanillin (commercial) and 360 ml of dichloromethane were mixed together under nitrogen and the mixture was cooled to 0° C. 135 ml of a molar solution of boron tribromide in dichloromethane were added and the mixture stood for 16 hours at ambient temperature and was then concentrated, cooled to 0° C. and acidified. The crystallized product was separated out, washed with water, dried and crystallized from an isopropanol-water mixture (1-2 by volume) to obtain 23.4 g of the expected product.

Infrared analysis (Nujol):
general absorption NH/OH 1662 (m) 1640 (F) cm$^{-1}$: C=O 1588, 1578, 1516 cm$^{-1}$: aromatic ring NMR analysis of the proton (DMSO 250 MHz in ppm):
7.25 (sl) and 7.44 (sl): Ar—H 9.68 (m): —CH=O 10.46, 1043 cm$^{-1}$: mobile absorption STEP B: 3-iodo-4,5-bis[(2-methoxy-ethoxy)-methoxy]benzaldehyde 67 ml of diisopropyl ethylamine were added to a suspension of 25.4 g of the product of Step A in 640 ml of dichloromethane and the mixture was cooled to 10° C. Then, 44 ml of chloro-( 2-methoxy-ethoxy)-methane were added over 45 minutes and the mixture was stirred for half an hour, diluted with 100 ml of water and was separated. Then, the organic phase was washed, dried, concentrated and chromatographed on silica, eluting with an ethyl acetate-hexane mixture (1/1) to obtain 25.5 g of the expected product.

Infrared analysis (CHCl$_3$):
Absence of OH 1698 and 2730 cm$^{-1}$: CH=O 1588, 1562, cm$^{-1}$: aromatic ring NMR analysis of the proton (CDCl$_3$ 250 MHz in ppm):
3.38 (sl) (6H): —OCH$_3$ 3.58 (m) (4H), 3.84 (m) (2H) and 4.05 (m) (2H): O—CH$_2$—CH$_2$—O 5.33 (sl) and 5.39 (sl): O—CH$_2$—O 7.68 (sl) and 7.96 (sl): Ar—H 9.82:—CH=O

PREPARATION 7

3,4,5-tris[(2-methoxy-ethoxy)-methoxy]benzaldehyde 52 ml of diisopropyl ethylamine were added to a suspension of 8 g of 3,4,5-trihydroxy benzaldehyde (commercial) in 160 ml of dichloromethane and the mixture was cooled to 0° to 5° C. Then, 35 ml of chloro-(2-metoxy-ethoxy)-methane were added over one and a half hours and the mixture was stirred, diluted with 100 ml of water and separated. The organic phase was washed, dried and concentrated to obtain 21.75 g of crude product which was used as is for what follows.

Infrared analysis (CHCl$_3$):
Absence of OH 1696 cm$^{-1}$: CH=O 1590, 1498 cm$^{-1}$: aromatic ring NMR analysis of the proton (CDCl$_3$ 250 MHz in ppm):
3.36 and 3.38 (9H): —OCH$_3$ 3.57 (m) (6H), 3.85 (m) (4H) and 3.99 (m) (2H): —O—CH$_2$—CH$_2$—O 5.31 (w) (2H) and 5.34 (s) (4H): O—CH$_2$—O 7.43 (s): Ar—H 9.82: —CH=O 5.31 (W) (2H) and 5.34 (s) (4H): O—CH$_2$—O 7.43 (s): Ar—H 9.82:—CH=O

PREPARATION 8

2,5-dichloro-3,4-bis[(2-methoxy-ethoxy)-methoxy]benzaldehyde
STEP A: 2,5-dichloro-3,4-dihydroxy benzaldehyde 27.6 g of 3,4-dihydroxy benzaldehyde (commercial) were dissolved in 300 ml of acetic acid and chlorine was bubbled through the solution at an ordinary temperature until 31.24 g of the gas had been consumed. The mixture was stirred for 42 hours and then was concentrated, cooled to 0° C. The precipitate was filtered, washed and dried to obtain 13.7 g of the expected product melting at 176° to 178° C. with a Rf=0.1 [eluant: ethyl acetate-cyclohexane (5-5)]

NMR analysis of the proton (DMSO 250 MHz in ppm):
7.24 (d J=2H$_2$) and 7.44 (d J=2H): Ar—H 9.90 (m): —CH=O 10.40: mobile absorption STEP B: 2,5-dichloro-3,4-bis[(2-methoxy-ethoxy)-methoxy] benzaldehyde 60.5 ml of diisopropyl ethylamine and then 11.27 ml of chloro-(2-methoxy-ethoxy)-methane were added to a solution of 6.83 g of the product of Step A in 265 ml of acetonitrile. The mixture was stirred for two hours at 35° C. and was evaporated to dryness. The residue was taken up in dichloromethane, washed, dried and the solvent was evaporated. Chromatography was carried out on silica, eluting with an ethyl acetate-cyclohexane mixture (6-4) to obtain 10.9 g of the expected product melting at 50° C. with a Rf=0.3.

Infrared analysis (PE 580):
1690 cm$^{-1}$: CH=O 1572, 1551 cm$^{-1}$: aromatic ring NMR analysis of the proton (CDCl$_3$ 250 MHz in ppm):
3.37 and 3.38: —OCH$_3$ 3.58 and 4.01 (m) (2H): O—CH$_2$—CH$_2$—O 5.29 and 5.36 (s): O—CH$_2$—O 7.78 (s): Ar—H 10.36 (s): —CH=O

PREPARATION 9

3-methoxy-4,5-bis[(2-methoxy-ethoxy)-methoxy]benzaldehyde 34 ml of diisopropyl ethylamine were added to a suspension of 8 g of 3,4-dihydroxy-5-methoxy benzaldehyde (commercial) in 80 ml of dichloromethane and the mixture was cooled to −5° C. to −10° C. Then, 23 ml of chloro-(2-methoxy-ethoxy)-methane were added over half an hour and the mixture was stirred for 16 hours. The organic phase was washed, dried, filtered, concentrated and chromatographed on silica, eluting with a hexane-ethyl acetate mixture (50-50) to obtain the expected product with a Rf=0.4 [eluant: hexane-ethyl acetate (30-70)].

Infrared analysis (CHCl$_3$ on PE 580):
Absence of OH 1696 cm$^{-1}$: CH=O 1588, 1498 cm$^{-1}$: aromatic ring NMR analysis of the proton (CDCl$_3$ 250 MHz in ppm):
3.36 (s) (3H) and 3.38 (s) (3H): O—CH$_2$—CH$_2$—OCH$_3$ 3.57 (m) (4H), 3.87 (m) (2H) and 4.00 (m) (2H): O—CH$_2$—CH$_2$—O 3.90 (s) (3H): Ar—OCH$_3$ 5.31 (s) (2H) and 5.35 (s) (2H): O—CH$_2$—O 7.19 (d J=2H$_2$) (1H) and 7.38 (d J=2Hz) (1H): Ar—H in the meta position 9.80 (s) (1H): —CH=O 3.93 g of the iodine derivative of Step B mixed with 6 g of thieno-[2,3-b]-pyridine were stirred for one and a half hours at 20° C. and the mixture was precipitated from 400 ml of ether, filtered and dried under vacuum to obtain 4.12 g of the desired product with a Rf=0.1 [eluant: dichloromethane-methanol (92-8)].

Analysis: C$_{49}$H$_{40}$IN$_5$O$_6$S$_3$

|  | % C | % H | % I | % N | % |
|---|---|---|---|---|---|
| Calculated: | 57.81 | 3.96 | 12.46 | 6.87 | 9.44 |
| Found: | 57.3 | 3.9 | 11.7 | 6.7 | 9.6 |

PREPARATION 10

1-[3-[7-[oxo-[2-[(triphenylmethyl)-amino]-thiazol-4-yl]-acetamido]- 2-[(4-methoxy-benzyloxy)-carbonyl-8-oxo-5-thia-1-azabicyclo [4,2,0][oct-2-en-3-yl]-2-propenyl]-thieno-[2,3-b]pyridinium iodide STEP A: 4-methoxy-benzyl 7β-[oxo-[2-[(triphenylmethyl)-amino]-thiazol- 4-yl]-acetamido]-3-[(Z+E)-3-chloro-1-propenyl ]-8-oxo- 5-thia-1-azabicyclo-[4,2,0]-oct-2-en-2-carboxylate 5 g of 4-methoxy benzyl 7β-amino-3-[(Z)-3-chloro-1-propenyl]- 8-oxo-5-thia-1-azabicyclo-[4,2,0]-oct-2-en-2-carboxylate hydrochloride (European Patent Application No. 0,333,154) and 0.72 g of oxo-[2-[(triphenylmethyl)-amino]-thiazol-4-yl]acetic acid (Belgian Patent Application No. 864,828) in 200 ml of dichloromethane were stirred under nitrogen and the mixture was cooled to 0° C. Then, 2.315 g of 1-(3-dimethylamino-propyl)-3-ethyl carbodiimide (EDC) were added, followed by stirring for 40 minutes, washing and drying. The solvents were evaporated and the residue was chromatographed, eluting with a dichloromethane-isopropyl ether mixture (9-1) to obtain 5.51 g of the expected product with a Rf=0.3.

STEP B: 4-methoxy benzyl 7β-[oxo-[2-[(triphenylmethyl)-amino]-thiazol- 4-yl]-acetamido]-3-[(Z+E)-3-iodo-1-propenyl]-8-oxo-5-thia- 1-azabicyclo-[4,2,0]-oct-2-en-2-carboxylate 5.5 g of the product of Step A were dissolved in 110 ml of acetone and 3.094 g of sodium iodide were added. The mixture was stirred for one and a half hours at 20° C. and the solvent was evaporated. The residue was taken up in 350 ml of dichloromethane, washed, dried, filtered and brought to dryness. The foam was filtered and the residue was chromatographed, eluting with a dichloromethane-isopropyl ether mixture (90-10) to obtain 3.93 g of the expected iodine with a Rf=0.3.

Infrared analysis (CHCl$_3$)

1786, 1721, 171 and 1633 cm$^{-1}$: C=O and β-lactam 1613, 1586, 1535, 1516 cm$^{-1}$: aromatic+conjugated system NMR analysis of the proton (CDCl$_3$ 300 MHz in ppm):
3.57: —S—CH$_2$—C(C=CH—)=C— 3.82 (s): Ar—OCH$_3$ 3.98 (d, J=8): —CH=CH—CH$_2$—I 5.03 (d J=5) ppm: CO—NH—CH(C=O)—CH—(N—)—S— 5.25 (AB, J=12): CO—O—CH$_2$—Ar 5.75: CO—NH—CH(C=O)—CH(N—)—S— 6.14 (dt, J=16 and 8) ppm: —C=CH—CH$_2$—I E isomerism 6.8 to 7.4 (m): —S—CH=C(C=N—)—N=C(NH-trityl)— and Ar—H of trityl 8.19 (d): CO—CO—NH—CH (C=O)—CH(N—)—S—

STEP C: 1-[3-[7β-oxo-[2-[(triphenylmethyl)-amino]-thiazol-4-yl]-acetamido]- 2-[(4-methoxy-benzyloxy)-carbonyl]- 8-oxo-5-thia- 1-azabicyclo-[4,2,0]-[oct-2-en-3-yl]-2-propenyl]-thieno-[2,3-b]pyridinium iodide NMR analysis of the proton (CDCl$_3$, 300 MHz in ppm):
5.02 (d): CO—NH—CH(C=O)—CH—(N—)—S— 5.27 (s): —CO—O—CH$_2$—Ar 5.6 (dd): —CH=CH—CH$_2$—N$^+$ 5.74 (dt): CO—NH—CH(C=O)—CH(N—)—S— 6.56 (d): —CH=CH—CH$_2$—N$^+$ E isomerism 7.3: Ar—H of the trityl 8.3: —S—CH=C(C=N—)—N=C(NH$_2$)— 7.89 (d): H in position 2 of thieno-[2,3-b]-pyridinium 7.71 (d): H in position 3 of thieno-[2,3-b]-pyridinium 8.8 (d): H in position 4 of thieno-[2,3-b]-pyridinium 8.10 (m): H in position 5 of thieno-[2,3-b]-pyridinium.

PREPARATION 11

[4-fluoro-(2,3-bis-hydroxy)-phenyl]-hydroxy acetic acid 51.2 g of 3-fluorocatechol and 36.8 g of glyoxylic acid were dissolved at 20° C. in 160 ml of water and 34.8 g of sodium hydroxide in solution in 400 ml of water were added to this solution cooled to 0° C. The mixture was heated for 4 hours at 46° C., then cooled to 0° C. and the pH was brought to 4.6 by the addition of concentrated hydrochloric acid. Extraction was carried out with ethyl ether (after evaporation 14.7 g of the starting 9-fluorocatechol were collected) and the aqueous phase was acidified with concentrated hydrochloric acid until a pH of 1.8 was obtained. Extraction was carried out with ethyl acetate and after evaporation of the solvent, 47.7 g of the desired product were obtained (mixture of isomers, 2,3-bis-hydroxy-4-fluoro; 3,4-bis-hydroxy-5-fluoro; 2-fluoro-3,4-bis-hydroxy) which was used as is in Step A of Example 16.

PREPARATION 12

3-bromo-4,5-bis-[(2-methoxyethoxy)-methoxy]benzaldehyde

Using the procedure of preparation 4, 5-bromo-vanillin was reacted to obtain the expected compound which was used in Example 15.

EXAMPLE 1

Internal salt of [6R-[3(E), 6α,7β(Z)]]-1-[3-[7-[ [2-amino-4-[carboxy-(2-chloro-3,4-dihydroxy-phenyl]-methoxy]-imino]-acetamido]- 2-carboxy-8-oxo-5-thia-1-azabicyclo-[4,2,0]-oct- 2-en-3-yl]-2-propenyl]-quinolinium STEP A: [2-chloro-3,4-bis-[(2-methoxy-ethoxy)-methoxy]-phenyl]-hydroxy acetic acid 2.42 g of lithium chloride and 7.02 g of potassium hydroxide were dissolved in 30 ml of water at 0° C. and a solution of 10 g of 2-chloro-3,4-bis-[(2-methoxy-ethoxy)-methoxy]benzaldehyde (synthesized in Preparation 1), 2.8 ml of bromoform and 38 ml of dioxane were added to this mixture. The mixture was stirred for 24 hours at 0° C. and then another 2.8 ml of bromoform were added. The mixture stood for 16 hours and after dilution with 100 ml of water, the solution was washed with ether, decanted, cooled to 0° C. and acidified until the pH was 2.5–3. Extraction was carried out with ether and the organic phase was washed with water and dried. The solvent was driven off to collect 11.4 g of the desired product in the form of an oil with a Rf=0.1 [eluant: methylene chloride-methanol-acetic acid (89-10-1)].

Infrared analysis (CHCl$_3$):

General absorption in the —OH region (acid+associated OH) 1726 cm$^{-1}$ complex: C=O of the acid function 1598–1489 cm$^{-1}$: aromatic nucleus NMR analysis of the proton (CDl$_3$ 250 MHz in ppm):

3.37 (l) (6H ): —OCH$_3$ 3.57 (m) (4H), 3.81 (m) (2H) and 4.01 (m) (2H): O—CH$_2$—O 5.25 (m) (4H) and 5.52 (sl) (1H): —O—CH$_2$—O and Ar—CH—CO 7.11 (sl) (2H): Ar—H.

STEP B: Diphenylmethyl [2-chloro-3,4-bis-[(2-methoxy-ethoxy)-methyl]-phenyl]-hydroxy acetate 11.4 g of the acid of Step A were dissolved at ambient temperature under nitrogen in 120 ml of dichloromethane and then 120 ml of a 0.3 molar solution of diphenyl diazomethane in dichloromethane were added at 15° C. The mixture was stirred for 16 hours at ambient temperature and then 30 ml of water were added, followed by decanting and acidifying with 309 ml of acetic acid, washing with a saturated solution of sodium bicarbonate, drying and evaporating the solvents. After chromatography on silica, eluting with an ethyl acetate-hexane mixture (60-40), 8.1 g of the desired product were obtained.

Infrared analysis (CHCl$_3$):

3528 cm$^{-1}$: non-phenolic —OH 1734 cm$^{-1}$: C=O of the ester function 1597, 1496, 487 cm$^{-1}$: aromatic nucleus NMR analysis of the proton (CDCl$_3$ 300MHz in ppm):

3.36 (s): —OCH$_3$ 3.55 (s) (4H), 3.82 (s) (2H) and 4.03 (s) (2H): —O—CH$_2$—CH$_2$—O 5.27 (s) and 5.29 (s): —O—CH$_2$—O 5.67 (d after exchange): Ar—CH(C=O)— OH 6.88 (s): CO—O—CHAr$_2$ 7.0 (masked) and 7.08 (d): coupled Ar—H (ortho of the tetra-substituted ring 7.00 (2H), 7.18 (3H) and 7.30 (s) (5H): Ar—H STEP C: Diphenylmethyl [2-chloro-3,4-bis-[(2-methoxy-ethoxy)methoxy]-phenyl]-phthalimidoxy acetate 2.47 g of N-hydroxy phthalimide and 7.55 g of triphenyl phosphine were added to a solution of 8.1 g of the ester of Step B in 90 ml of tetrahydrofuran and the mixture was cooled to 10° C. Then 3.88 ml of diethyl azodicarboxylate (DEAD) were poured into it and the mixture was stirred for 16 hours. After concentration of the solvents and chromatography on silica, eluting with an ethyl acetate-hexane mixture (60-40), 6.27 g of the desired product were obtained in the form of an oil with a Rf=0.25.

Infrared analysis (CHCl$_3$):

1739, 1755 (sh) and 1795 cm$^{-1}$: C=O 1597, 1489 cm$^{-1}$: aromatic nucleus

NMR analysis of the proton (CDCl$_3$ 300 MHz in ppm):

3.33 and 3.37: —OCH$_3$ 3.54 (m) (4H), 3.82 (m) (2H) and 3.92 (m) (2H): O—CH$_2$—CH$_2$—O— 5.22 (AB sys.) and 5.30 (AB sys.): —O—CH$_2$—O 6.50: Ar—CH(C=O)— O— 6.93 (s) ppm: CO—O—CH—Ar$_2$ 7.09 (d), 7.41 (d): coupled Ar—H (ortho of the tetrasubstituted ring) 7.44 (d) (4H): Ar—H of the phthalimido 7.05 to 7.33 ppm: Ar—H aromatics STEP D: Diphenylmethyl aminoxy (2-chloro-3,4-bis-[( 2-methoxy-ethoxy) -methoxy]-phenyl] acetate 6.27 g of the product of Step C were dissolved in 65 ml of ethanol and the solution was cooled to 5° C. Then 0.47 ml of hydrazine hydrate were added and the mixture stood at 5° C. for half an hour and then was returned to ambient temperature for 2 hours. After filtration, evaporation of the solvent and chromatography on silica, eluting with ethyl acetate, 3.64 g of the desired product were obtained in the form of an oil with a Rf=0.3.

| Analysis: C$_{29}$H$_{34}$ClNO$_9$ | | | | | | | |
|---|---|---|---|---|---|---|---|
| Calculated: | % C | 60.46 | % H | 5.95 | % N | 2.43 |
| Found: | | 60.1 | | 6.1 | | 2.6 |

Infrared analysis (CHCl$_3$):

3235 cm$^{-1}$: —NH$_2$ 1738 cm$^{-1}$: C=O of the ester function 1598, 1572, 1490 cm$^{-1}$: aromatic nucleus+NH$_2$ STEP E: [[[1-[2-chloro-3,4-bis-[(2-methoxy-ethoxy)-methoxy]-phenyl]- 2-oxo-2-(diphenylmethoxy)-ethyl]-oxy]-imino] [2-[ (triphenylmethyl)-amino]-thiazol-4-yl] acetic acid 0.69 g of the product of Step D and 0.496 g of oxo-[2-[ (triphenylmethyl)-amino]-thiazol-4-yl] acetic acid (Belgian Patent Applicaton No. 864,828) were stirred for 3 hours under nitrogen and at ambient temperature in the presence of 7 ml of methanol and then the solvent was eliminated. The residue was chromatographed on silica, eluting with a methylene chloride-methanol mixture (95-5) to obtain 0.726 g of the expected product with a Rf=0.3 [eluant: CHCl$_2$—MEOH (90-10)].

| Analysis: C$_{53}$H$_{50}$ClN$_3$O$_{11}$S | | | | | | | | | |
|---|---|---|---|---|---|---|---|---|---|
| Calculated: | % C | 65.45 | % H | 5.18 | % N | 4.32 | % S | 3.29 | % Cl | 3.64 |
| Found: | | 63.7 | | 5.1 | | 4.2 | | 3.2 | | 3.1 |

STEP F: 4-methoxy-benzyl 7β-[[[[1-[2-chloro-3,4-bis-[ (2-methoxy-ethoxy)-methoxy]-phenyl]-2-oxo-2- (diphenylmethoxy)-ethyl]-oxy]-imino]-[ 2-[(triphenylmethyl)-amino]-thiazol-4-yl]-acetamido]-3-[ (Z)-3-chloro-1-propenyl]-8-oxo-5-thia-1-azabicyclo-[4,2,0]-oct- 2-en-2-carboxylate 0.322 g of 4-methoxy-benzyl 7β-amino-3-[(Z)-3-chloro-1-propenyl]- 8-oxo-5-thia-1-azabicyclo-[4,2,0]-oct-2-en-2-carboxylate hydrochloride (European Patent Application No. 0,333,154) and 0.72 g of the product of Step E were stirred in 10 ml of dichloromethane and the mixture was cooled to 5° C. Then, 0.1803 g of 1-(3-dimethylaminopropyl)-3-ethyl carbodiimide (EDC) were added, and the mixture was stirred for half an hour. Then, the mixture was treated with 10 ml of potassium hydrogenophosphate in 10 ml of methylene chloride, followed by decanting, washing and drying and evaporating the solvents to obtain 0.670 g of the expected product with a Rf=0.43 [eluant: methylene chloride-ethyl acetate (80-20)].

STEP G: 4-methoxy-benzyl 7β-[[[[1-[2-chloro-3,4-bis-[( 2-methoxy-ethoxy)-methoxy]-phenyl]-2-oxo-2- (diphenylmethoxy)-ethyl]-oxy]-imino] 2-[(triphenylmethyl)-amino]-thiazol-4-yl]-acetamido]-3-[ (Z)-3-iodo-1-propenyl] -8-oxo-5-thia-1-azabicyclo[]-4,2,0]-oct- 2-en-2-carboxylate 0.67 g of the product of Step F in 10 ml of acetone and 0.223 g of sodium iodide were stirred for one hour at ambient temperature in the presence of an iodine crystal. After elimination of the solvent, the residue was taken up in methylene chloride and the organic phase was washed and dried. The solvent was eliminated and crystallization was carried out from isopropyl ether to obtain 0.579 g of the iodated product with a Rf=0.27 [eluant: methylene chloride-methanol (90-10)].

STEP H: 1-[3-[7-[[[[1[2-chloro-3,4-bis-[ (2-methoxy-ethoxy)-methoxy]-phenyl]-2-oxo-2-(diphenylmethoxy)-ethyl]-oxy]-imino] [2[(triphenylmethyl)-amino]-thiazol-4-yl]-acetamido]- 2-[(4-methoxy-benzyloxy)-carbonyl]-8-oxo-5-thia-1-azabicyclo[ 4,2,0][oct-2-en-3-yl]-2-propenyl]-quinolinium iodide 0.572 g of the product of Step G were dissolved in 6 ml of methylene chloride and 0.234 g of quinoline were added. The mixture was stirred for one hour and the solvent was evaporated. The residue was taken up in ether, followed by crystallization and separation, and chromatography was carried out on silica, eluting with a methylene chloride-methanol mixture (9-1) to obtain 0.235 g of the expected product with a Rf=0.27 [eluant: methylene chloride-methanol (90-10)].

NMR analysis of the proton ($CDCl_3$ 250 MHz; ppm):
3.31 to 3.34: —$OCH_3$ 3.73 (s): Ar—O—$CH_2$ 3.42 to 4.01: $CH_2$—S and O—$CH_2$—$CH_2$—O 4.92 (m): —CH (N—)—S— 5.84 (m): —NH—CH—C— 5.20 to 5.30: —O—$CH_2$—O and COO—$CH_2$—Ar 5.93 to 6.15: =C—CH—$N^+$ 6.40 to 6.55: =CH—$CH_2$— E isomerism and O—CH—Ar resolved 6.76: H in position 5 of the thiazole ring 6.86 to 7.42: —CH—Ar, COO—$CHAr_2$, =C—CH=CH— E isomerism 8.05 to 8.25 (3H), 8.37 (m) (1H), 8.92 (d (resolved)) (1H), and 10.4 (d): hydrogens of the quinoline ring 7.83 and 8.27: —CO—NH—

STEP I: Internal salt of [6R -[3(E), 6α, 7β-(Z)] ]-1-[3-[7-[[(2-amino- 4-thiazolyl) -[carboxy-(2-chloro-3,4-dihydroxy-phenyl)-methoxy]-imino]-acetamido]- 2-carboxy-8-oxo-5-thia-1-azabicyclo [4,2,0]oct-2-en-3-yl]-2-propenyl]-quinolinium isomer (R) and isomer (S)

A mixture of 0.235 g of the product of Step H and 5 ml of trifluoroacetic acid containing 10% anisole was stirred for 90 minutes at ambient temperature. After the addition of ether, the mixture was subjected to ultrasonics, followed by filtration, washing and drying for 16 hours under vacuum at ambient temperature to obtain 0.118 g of the desired internal salt.

NMR analysis of the proton (DMSO 300 MHz in ppm):
—S—$CH_2$—C(C=CH—)=C— masked by the water of DMSO 5.15 (resolved d) ppm: CO—NH—CH(C=O)—CH—(N—)—S— 5.72 to 5.89 (4H): CO—NH—CH(C=O)—CH(N—)—S—, Ar—CH(CO—O—)—O— and —CH=CH—$CH_2$—$N^+$ 6.38 (m) ppm: —CH=CH—CH—$N^+$ E isomerism 6.7 to 6.82: —S—CH=C (C=N—)—N=C ($NH_2$)— and Ar—H of the catechol 6.98 ppm (d J=15.5): —CH=CH—CH—$N^+$ E isomerism 7.30:$NH_2$ 8.06 (t) (1H), 8.25 (m) (2H), 8.54 (m) (2H) and 9.34 (d) (1H): Ar—H of the quinoline 9.29 (sl) and 9.94 (sl): mobile H's 9.47 (d) and 9.58 (d): Ar—H and —CO—NH—CH(C=O)—CH(N—)—S—

EXAMPLE 2

The internal salt of [6R-[3(E), 6α, 7β-((Z)]]-1-[3-[ 7-[[(2-amino-4-thiazolyl) [carboxy-(3-cyano-4,5-dihydroxy-phenyl)-methoxy]imino]-acetamido]- 2-carboxy-8-oxo-5-thia-1-azabicyclo-[4,2,0 ]-oct-2-en-3-yl ]-2-propenyl]-quinolinium (R) or (S) or an (R+S) mixture STEP A: [3-cyano-4,5-bis[-(2-methoxy-ethoxy)-methoxy]-phenyl]-hydroxy acetic acid Using the procedure of Step A of Example 1, 6.2 g of the product of Step C of preparation 2, 4.4 g of potassium hydroxide, 3.15 g of lithium bromide, 1.7 ml of bromoform and 15 ml were reacted and after stirring for 48 hours at −5° C., 7.2 g of crude acid were obtained which, after chromatography on silica eluting with a dichloromethane-methanol-acetic acid mixture (90-7-3), yielded 3.42 g of the desired product with a Rf=0.3 [eluant: methylene chloride-methanol-acetic acid (91-07-3)].

Infrared analysis ($CHCl_3$):
General absorption in the —OH region (acid+associated OH) 1721 $cm^{-1}$ max+1750 $cm^{-1}$ sh.: C=O of the acid function 2235 $cm^{-1}$ 1602–1586–1489 $cm^{-1}$: aromatic nucleus STEP B: Diphenylmethyl [3-cyano-4,5-bis-[(2-methoxy-ethoxy)-methoxy]-phenyl]-hydroxy acetate 8.5 g of the acid of Step A were dissolved at ambient temperature under nitrogen in 100 ml of dichloromethane and then 75 ml of a 0.3 molar solution of diphenyl diazomethane in ether were added at 15° C. The mixture was stirred for 16 hours at ambient temperature and then 30 ml of water were added, followed by decanting and acidifying with 30 ml of acetic acid, washing with a saturated solution of sodium bicarbonate, drying and evaporating the solvents. After chromatography on silica and eluting with an ethyl acetate-hexane mixture (50-50), 4.2 g of the desired product with a Rf=0.3 were obtained.

Infrared analysis ($CHCl_3$):
3525 $cm^{-1}$: non-phenolic —OH 2235 $cm^{-1}$: C=N 1732 and 1750 $cm^{-1}$: C=O of the ester function 1600, 1585, 1495, 1490 $cm^{-1}$: aromatic nucleus NMR analysis of the proton ($CDCl_3$ 300 MHz in ppm):
3.32 to 3.47:—$OCH_3$ 3.58 and 3.72: O—$CH_2$—$CH_2$—O 5.15 to 5.40: —$OCH_2$—O and Ar—CH(C=O)—OH 6.89 (s): CO—O—$CHAr_2$ 7.24 to 7.50: Ar—H Analysis: $C_{32}H_{25}ClN_6O_9S_2 + 1.5 C_2HF_3O_2 + 0.5$ HI;

molecular weight = 1014

| | % C | % H | % N | % Cl | % S | % F | % I |
|---|---|---|---|---|---|---|---|
| Calculated: | 43.81 | 2.88 | 8.28 | 3.49 | 6.32 | 8.42 | 6.25 |
| Found: | 44.1 | 2.7 | 8.5 | 4.1 | 6.7 | 8.5 | 6.0 |

STEP C: Diphenylmethyl [3-cyano-4,5-bis-[ (2-methoxy-ethoxy)-methoxy-phenyl]-phthalimidoxy acetate 0.134 g of N-hydroxy phthalimide and 0.409 g of triphenyl phosphine were added to a solution of 0.430 g of the ester of Step B in 10 ml of tetrahydrofuran and the mixture was cooled to −10° C. Then, 0.21 ml of diethyl azodicarboxylate (DEAD) was poured in and the mixture was stirred for 16 hours. After concentrating the solvents and chromatography on silica eluting with a dichloromethane-acetone mixture (95-5), 0.2 g of the desired product in the form of an oil and with a Rf=0.25 [eluant: dichloromethane-acetone (97-3)] were obtained.

Infrared analysis (CHCl$_3$):

1792 (m), 1775 (sh) 1760 (sh) and 1738 (max) cm$^{-1}$: C=O 2230 cm$^{-1}$: C=N 1604, 1586, 1490 cm$^{-1}$: aromatic nucleus STEP D: Diphenylmethyl-aminoxy [3-cyano-4,5-bis- [(2-methoxy-ethoxy)-methoxy]-phenyl]acetate 2.7 g of the product of Step C were dissolved under nitrogen in 80 ml of ethanol and the solution was cooled to −2° C. Then, 0.20 ml of hydrazine hydrate were added and the mixture was held at −2° C. for half an hour, then returned to ambient temperature for one hour. After filtration, evaporation of the solvent and chromatography on silica eluting with an ethyl acetate-hexane mixture (7-3) yielded 1.8 g of the desired product in the form of an oil with a Rf=0.25.

Analysis: $C_{30}H_{34}N_2O_9$

| | | % C | | % H | | % N | |
|---|---|---|---|---|---|---|---|
| Calculated: | | 63.53 | | 6.04 | | 4.94 | |
| Found: | | 63.3 | | 6.4 | | 4.6 | |

Infrared analysis (CHCl$_3$):

3335 cm$^{-1}$: O—NH$_2$ 2230 cm$^{-1}$: C=N 1748 cm$^{-1}$: C=O of the ester function 1600, 1588, 1488 cm$^{-1}$: aromatic nucleus+NH$_2$ STEP E: [[[1-[3-cyano-4,5-bis-[(2-methoxy-ethoxy)-methoxy]-phenyl]- 2-oxo-2-(diphenylmethoxy)-ethyl]-oxy]-imino] [2-[(triphenylmethyl)-amino]-thiazolyl] acetic acid 0.650 g of the product of Step D and 0.428 g of oxo-[2-[(tri-phenylmethyl)-amino]-thiazol-4-yl]-acetic acid (Belgium Patent Application No. 864,828) were stirred for 2 hours under nitrogen at ambient temperature in the presence of 6 ml of methanol. The solvent was eliminated and the residue was taken up in ether. Filtration was carried out and the filtrate was chromatographed on silica, eluting with a methylene chloride-methanol mixture (95-5) to obtain 0.841 g in total of the expected product melting at 158° C.

Infrared analysis (CHCl$_3$):

3402 cm$^{-1}$: =C—NH General absorption OH/NH 2235 cm$^{-1}$: C=N 1755 (sh), 1740 (max) and 1717 (sh) cm$^{-1}$: C=O 1587, 1531 1509 and 1490 cm$^{-1}$: aromatic, heterocycle, conjugated system NMR analysis of the proton (in ppm):

3.36 (s) and 3.43 (s): —OCH$_3$ 3.55 to 3.90 (m) (6H) and 4.05 (m) (2H): O—CH$_2$—CH$_2$—O 5.03 (d), 5.12 (d) and 5.33 (d): —O—CH$_2$—O 5.85 (s): Ar—CH(C=O)—O— 6.68 (s): CO—O—CHAr$_2$, 6.87 (s): —S—CH=C(C=N)—N 7.10 to 7.36 (massive) (27H), 7.67 (d) (1H): Ar—H STEP F: 4-methoxy benzyl 7β-[[[[1-[3-cyano-4,5-bis- [ (2-methoxyethoxy)-methoxy]-phenyl]-2-oxo-2-(diphenyl methoxy)-ethyl]-oxy]-imino] [2-(triphenyl methyl)-amino]-thiazol-4-yl]-acetamido]-3-[ (Z)-3-chloro-1-propenyl]-8-oxo-5-thia-1-azabicyclo-[4,2,0 ]-oct-2-en-2-carboxylate 0.160 g of 4-methoxy-benzyl 7β-amino-3-[(Z)-3-chloro-1-propenyl]- 8-oxo-5-thia-1-azabicyclo-[4,2,0]-oct-2-en-2-carboxylate hydrochloride (European Patent Application No. 0.333,154) and 0.36 g of the product of Step E in 5 ml of dichloromethane were stirred and cooled to 5° C. Then, 0.0893 g of EDC were added and the mixture was stirred for 15 minutes, then treated with 15 ml of potassium hydrogenophosphate in 8 ml of dichloromethane, decanted, washed and dried. The solvents were evaporated and after chromatography on silica, eluting with a dichloromethane-ethyl acetate mixture (8-2) yielded. 0.349 g of the expected product with a Rf=0.4 [eluant: dichloromethane-ethyl acetate (8-2)].

STEP G: 4-methoxy-benzyl 7β-[[[[1-[3-cyano-4,5-bis-[(2-methoxy-ethoxy)-methoxy]-phenyl]-2-oxo-2-(diphenyl methoxy)-ethyl]-oxy]-imino] 2-[(triphenylmethyl)-amino]-thiazol-4-yl]-acetamido]-3-[ (Z)-3-iodo-1-propenyl]-8-oxo-5-thia-1-azabicyclo-[4,2,0]-oct- 2-en-2 -carboxylate 0.573 g of the product of Step F in 7 ml of actone and 0.192 g of sodium iodide wre stirred for one hour at ambient temperature in the presence of an iodine crystal. After elimination of the solvent, the residue was taken up in dichloromethane and the organic phase was washed and dried. The solvent was eliminated and the residue was crystallized from isopropyl ether to collect 0.463 g of the iodated product with a Rf=0.30 [eluant: dichloromethane methanol (9-2)].

STEP H: 1-[3-[7-β-[[[[1-[3-cyano-4,5-bis-[ (2-methoxy-ethoxy)-methoxy]-phenyl]-2-oxo-2-(diphenylmethoxy)-ethyl]-oxy]-imino][ 2-(triphenylmethyl)-amino]-thiazol-4-yl]-acetamido]-2-[ (4-methoxy-benzyloxy)-carbonyl]-8-oxo-5-thia-1-azabicyclo-[4,2,0 ]-[oct-2-en-3-yl]-2-propenyl]-quinolinium iodide 0.463 g of the product of Step G were dissolved in 4 ml of dichloromethane and 0.191 g of quinoline was added. The mixture was stirred for one hour, and the solvent was evaporated. The residue was taken up in ether and crystallized and separation was carried out followed by chromatography on silica. Elution with a dichloromethane-methanol mixture (97-3) yielded. 0.241 g of the expected product with a Rf=0.27.

NMR analysis of the proton (CDCl$_3$ 400 MHz in ppm):

3.25 (s), 3.27 (s) and 3.34: —OCH$_3$ 3.26 to 4.04: CH$_2$—S and O—CH$_2$—CH$_2$—O 3.98 (s) Ar—O—CH$_3$ 4.90 to 5.08 and 5.15 to 5.40: —CH(N—)—S—, =C—CH$_2$—N$^+$, —O—CH$_2$—O and COO—CH$_2$—Ar 5.75 to 6.05: N—CH(C=O)—CH—(N—)—S— and—O—CH(C=O)—Ar 6.38 (m) and 6.56 (m): =CH—CH— E isomerism 6.73 (m):L —S—CH—C(C=N)—N 6.80 to 7.50: trityl's, COO—CHAr$_2$, 7.9 to 8.56 (5H), 8.56 (d) and 8.87 (d) resolved in (1H), 10.27 (d) and 10.83 (d): hydrogens of the quinoline ring and —NH—

STEP I: Internal salt of [6R-[3-(E), 6α, 7β(Z)]]-1- [ 3-[7-[[[(2-amino-4-thiazolyl) carboxy-(3-cyano- 4,5-dihyroxy-phenyl)-methoxy]-imino]-]-acetamido]-2-carboxy-8-oxo-5-thia- 1-azabicyclo-[4,2,0]-oct-2-en-3-yl]-2-propenyl] -quinolinium isomer (R) and isomer (S)

A mixture of 0.241 g of the product of Step H and 5 ml of trifluoroacetic acid containing 10% anisole was stirred for one and a half hours at ambient temperature. After the addition of ether, crystallizing, filtering, washing and drying for 16 hours under vacuum at ambient temperature, 0.128 g of the sought internal salt were obtained.

Analysis: $C_{33}H_{25}N_7O_9S_2 + 1.4\ C_2HF_3O_2 + 0.4\ HI$

| | % C | % H | % N | % S | % F | % I |
|---|---|---|---|---|---|---|
| Calculated: | 45.8 | 2.87 | 10.43 | 6.83 | 8.5 | 5.4 |
| Found: | 44.1 | 2.7 | 8.5 | 7.0 | 8.0 | 4.1 |

NMR analysis of the proton (DMSO 300 MHz in ppm):
3.53 (d) and 3.74 (d): —S—CH$_2$—C(C=CH—)=C— 5.14 (resolved d) ppm: CO—NH—CH—(C=O)—CH—(N—)—S— 5.40 (s): Ar—CH(CO—O—)—O— 5.76 (m) CO—NH—CH—(C=O)—CH(N—)—S— to 5.89 (m): —CH=CH—CH—N$^+$, 6.34 (m) ppm: —CH=CH—CH—N$^+$ E isomerism 6.76 (s) and 6.79 (s): —S—CH=C(C=N—)—N=C(NH$_2$)— 6.98 ppm (d J=16): —CH=CH—CH—N$^+$ E isomerism 7.11 to 7.15 (m) (2H): Ar—H 7.30 (m) and 10.38 (m): mobile H's 8.06 (t) (1H), 8.26 (m) (2H), 8.53 (m) (2H), 9.33 (d) and 9.58 (d): Ar—H 9.60 (d) and 9.65 (d): —CO—NH—CH(C=O)—CH(N—)—S—

EXAMPLE 3

The internal salt of [6R-[3(E), 7β-(Z)]]-1-[3-[7-[[ (2-amino-4-thiazolyl) [carboxy-(3-fluoro-4,5-dihydroxy-phenyl)-methoxy]-imino]-acetamido]- 2-carboxy-8-oxo-5-thia-1-azabicyclo-[4,2,0]-oct-2-en-3-yl]-2-propenyl]-quinolinium (R) or (S) or an (R+S) mixture STEP A: [3-fluoro-4,5-bis-[C2-methoxy-ethoxy)-methoxy]-phenyl]-hydroxy-acetic acid 0.662 g of lithium bromide and 3.6 g of potassium hydroxide were dissolved in 13 ml of water at 0° C. and a solution of 5.5 g of 3-fluoro-4,5-bis-[(2-methoxy-ethoxy)-methoxy benzaldehyde (synthesized in Preparation 3), 2.85 ml of bromoform and 13 ml of dioxane were added to this mixture. The mixture stood with stirring for 24 hours at 0° C. and then another 2.85 ml of bromoform were added. The mixture stood for one night and after dilution in water and washing with ether, decanting took place, followed by cooling to 0° C. acidifying until the pH was 2.5–3 and extracting with ether. The organic phase was washed with water, dried and the solvent was evaporated to obtain 5.3 g of the desired product in the form of an oil.

Infrared analysis (CHCl$_3$):
3600 cm$^{-1}$: —OH region (acid+associated OH) 1715 cm$^{-1}$ complex: C=O of the acid function 1616, 1595 and 1510 cm$^{-1}$: aromatic nucleus STEP B: Diphenylmethyl [3-fluoro-4,5-bis-[ (2-methoxy-ethoxy)-methoxy]-phenyl]-hydroxy-acetate 5.3 g of the acid of Step A were dissolved in 66 ml of dichloromethane and then 46 ml of a solution of diphenyl diazomethane at 6.5 g in ether were added at 15° C. The mixture was stirred for 16 hours at ambient temperature and then water was added, followed by decanting and acidifying with acetic acid. Washing with a saturated solution of sodium bicarbonate, drying and evaporating the solvents yielded after chromatography on silica and eluting with an ethyl acetate-hexane mixture (50-50) 4.0 g of the desired product with a Rf=0.17.

Infrared analysis (CHCl$_3$):
3520 cm$^{-1}$: non-phenolic —OH 1735 cm$^{-1}$: C=O of the ester function 1615, 1595 and 1509 cm$^{-1}$: aromatic nucleus NMR analysis of the proton (CDCl$_3$ 2500 MHz in ppm):
3.33 (s) and 3.37 (s): —OCH$_3$ 3.46 (m), 3.57 (m), 3.78 (m) and 3.98 (m): O—CH$_2$—CH$_2$—O 5.19 to 5.30: —O—CH$_3$—O and Ar—CH(C=O—O)—O— 6.87 (s): CO—O—CHAr$_2$ 6.87 (m) (1H), 6.97 (m) (2H), 7.07 (m) (1H), 7.21 (m) (3H) and 7.32 (m) (5H): Ar—H STEP C: Diphenylmethyl [3-fluoro-4,5-bis-[ (2-methoxy-ethoxy)-methoxy]-phenyl]-phthalimidoxy-acetate 0.77 g of N-hydroxy phthalimide and 2.42 g of triphenyl phosphine were added to a solution of 2.6 g of the ester of Step B in 28 ml of tetrahydrofuran, and after cooling to –10° C., 14 ml of diethyl azodicarboxylate (DEAD) were added dropwise into the resultant mixture. The mixture was stirred at 0° C. for one and a half hours. After concentration of the solvents and chromatography on silica, elution with a dichloromethane-acetone (95-5) mixture yielded 2.56 g of the desired product in the form of an oil with Rf=0.6 [eluant: dichloromethane-acetone (85-15)].

Infrared analysis (CHCl$_3$):
1794, 1752 and 1738 (max) cm$^{-1}$: C=O

NMR analysis of the proton (CDCl$_3$ 250 MHz in ppm):
3.34 (s) and 3.33 (s): —OCH$_3$ 3.48 (m) (2H), 3.56 (m) (2H), 3.77 (m) (2H) and 3.96 (m) (2H): O—CH$_2$—CH$_2$—O 5.22 (m) (4H): —O—CH$_2$—O 5.92 (s): Ar—CH(C=O—O)—O— 6.92 (s): CO—O—CHAr$_2$ 7.00 to 7.35 (m): Ar—H 7.75 (m) (4H): Ar—H of the phthalimide STEP D: Diphenylmethyl aminoxy-[3-fluoro-4,5-bis-[ (2-methoxy-ethoxy)-methoxy]-phenyl]-acetate 2.4 g of the product of Step C were dissolved under nitrogen in 25 ml of ethanol and the mixture was cooled to –5° C. Then, 0.38 ml of hydrazine hydrate were added and the mixture was held at –5° C. for two hours. After filtration, the solvent was evaporated and the residue was chromatographed on silica, eluting with a mixture of ethyl acetate-hexane (7-3) to obtain 1.67 g of the desired product in the form of an oil with a Rf=0.3.

Infrared analysis (CHCl$_3$):
3340 cm$^{-1}$: O—NH$_2$ 1747 cm$^{-1}$: C=O of the ester function 1616, 1596, 1581, 1508 and 1497 cm$^{-1}$: aromatic nucleus+NH$_2$ NMR analysis of the proton (CDCl$_3$ 300 MHz in ppm):
3.34 and 3.36: —OCH$_3$ 3.48, 3.56, 3.77 and 3.97: O—CH$_2$—CH$_2$—O 5.17 (s): Ar—CH(C=O—O)—O— 5.20 and 5.21: —O—CH$_2$—O 5.79 (s): O—NH$_2$ 6.82 (dd): Ar—H in ortho position of F 6.91 (s): CO—O—CHAr$_2$ 7.02: Ar—H in para position of F 7.05 to 7.40: Ar—H STEP E: [[[1-[3-fluoro-4,5-bis-[ (2-methoxy-ethoxy)-methoxy]-phenyl]-2-oxo- 2-(diphenylmethoxy)-ethyl]-oxy]-imino]-[2-[ (triphenylmethyl)-amino]-thiazol-4-yl]-acetic acid 0.640 g of the product of Step D and and 0.474 g of oxo-[2-[(triphenylmethyl)-amino]-thiazol-4-yl]-acetic acid (Belgian Patent Application No. 864,828) were stirred for 4 and a half hours under nitrogen and at ambient temperature in the presence of 20 ml of methanol. Then, the solvent was eliminated, and the residue was chromatographed on silica, eluting with a dichloromethane-methanol (95—5) mixture to obtain 0.612 g of the expected product with a Rf=0.35 [eluant: dichloromethane-methanol (9-1)].

Infrared analysis (CHCl$_3$):
3400 cm$^{-1}$: =C—NH 1755 (shoulder), 1736 (max) cm$^{-1}$: C=O 1695, 1527, 1509 and 1496 cm$^{-1}$: aromatic, heterocycle, 1635 cm$^{-1}$: C=O NMR analysis of the proton (CDCl$_3$ in ppm):

3.09 (s) and 3.22 (s): —OCH$_3$ 3.30 (m), 3.55 (m), 3.60 (m), 3.92 (m),: O—CH$_2$—CH$_2$—O 5.15 (s), 5.10 (d) and 5.20 (d): —O—CH$_2$—O 5.81 (s): Ar—CH(C=O)—O— 6.56 (s): CO—O—CHAr$_2$, 6.74 (s): —S—CH=C(C=N)—N 7.10 to 7.33 (m): Ar—H STEP F: 4-methoxy-benzyl 7β- [[[[[1-[ 3-fluoro-4,5-bis-[( 2-methoxy-ethoxy)-methoxy]-phenyl]-2-oxo-2- (diphenylmethoxy)-ethyl]-oxy]-imino]-[ 2-(triphenylmethyl)-amino]-thiazol-4-yl]-acetamido]-3 [(Z)-3-chloro-1-propenyl]-8-oxo-5-thia-1-azabicyclo-[4,2,0]-oct- 2 -en-2 -carboxylate 0.289 g of 4-methoxy-benzyl 7β-amino-3-[(Z)-3-chloro-1-propenyl]-8-oxo-5-thia-1-azabicyclo-[4,2,0]-oct-2-en-2-carboxylate hydrochloride (European Patent Application No. 0.333,154), and 0.641 g of the product of Step E in 6 ml of dichloromethane were stirred and cooled to 5° C. Then 0.160 g of EDC was added and the mixture was stirred for half an hour. Then, the mixture was treated with potassium hydrogen phosphate in dichloromethane, followed by decanting, washing, drying and evaporating the solvents. After chromatographing on silica eluting with a dichloromethane-ethyl acetate (8-2) mixture, 0.678 g of the expected product with a Rf=0.4 [eluant: dichloromethane-ethyl acetate (8-2)] were obtained.

STEP G: 4-methoxy-benzyl 7β-[[[[[1-[ 3-fluoro-4,5-bis-[(2-methoxy-ethoxy)-methoxy]-phenyl]-2-oxo- 2-(diphenyl-methoxy)-ethyl]-oxy]-imino]-[2-(triphenylmethyl)-amino]-thiazol- 4-yl]-acetamido]-3-[(Z)-3-iodo-propenyl]-8-oxo-5-thia-1-azabicyclo-4,2,0 ]-oct-2-en-2-carboxylate 0.678 g of the product of Step F in 7 ml of acetone and 0.228 g of sodium iodide were stirred for one hour at ambient temperation in the presence of an iodine crystal. After eliminating of the solvent, the residue was taken up in dichloromethane and the organic phase was washed and dried. The solvent was eliminated and the residue was separated to obtain 0.501 g of the iodated product with a Rf=0.2 [eluant: dichloromethane-methanol (97-3)].

STEP H: 1-[3-[7β-[[[[[1-[3-fluoro-4,5-bis-[ (2-methoxy-ethoxy)-methoxy]-phenyl]-2-oxo-2-(diphenyl methoxy)-ethyl]-oxy]-imino-[2-(triphenylmethyl)-amino]-thiazol-4-yl]-acetamido]-2-[ (4-methoxy-benzyloxy)-carbonyl]-8-oxo-5-thia-1-azabicyclo-[ 4,2,0]-oct-2-en-3-yl]-2-propenyl] -quinolinium iodide.

0.500 g of the product of Step G dissolved in 2 ml of dichloromethane and 0.226 ml of quinoline were added and the solvent was concentrated. The mixture was stirred for one hour at ambient temperature and 2 ml of dichloromethane were added. Then precipitation was carried out with ether and chromatography took place on silica eluting with a dichloromethane-methanol (97-3) mixture to obtain 0.220 g of the expected product with a Rf=0.20.

STEP I: Internal salt of [6R-[3(E), 6α, 7β-(Z)]]1-[3-[ 7-[[(2-amino-4-thiazolyl)-[[carboxy-(3-fluoro- 4,5-dihydroxy-phenyl)-methoxy]-imino]-acetamido]-2-carboxy-8-oxo-5-thia-1-azabicyclo-[4,2,0]-oct-2-en-3-yl]-2-propenyl]-quinolinium (R) isomer and (S) isomer A mixture of 0.220 g of the product of Step H and 5 ml of trifluoroacetic acid containing 10% anisole was stirred at ambient temperature for one and a half hours. After 15 ml of ether were added, the precipitate was washed and dried to obtain 0.0994 g of the desired internal salt.

Analysis: $C_{32}H_{25}FN_6O_9S_2$ + 1.2 $C_2HF_3O_2$ + 0.5 HI

|  | % C | % H | % n | % S | % F | % I |
|---|---|---|---|---|---|---|
| Calculated: | 44.8 | 2.89 | 9.12 | 6.95 | 9.48 | 6.88 |
| Found: | 44.7 | 2.8 | 8.8 | 6.6 | 9.1 | 6.6 |

NMR analysis of the proton (DMSO 300 MHz in ppm):

3.5 and 3.8: (masked by the water of the solvent) 5.14 (d resolved) ppm: CO—NH—CH(C=O)—CH—(N—)—S 5.34 (s resolved): Ar—CH(CO—O—)—O— 5.77 (dd resolved d resolved): CO—NH—CH(C=O)—CH(N—)—S— 5.80 to 6.0: —CH=CH—CH$_2$—N$^+$, 6.37 (m): —CH=CH—CH$_2$—N$^+$ E isomerism 6.7 to 6.8: —S—CH=C(C=N—)—N=C(NH$_2$)— and Ar—H in ortho and para position of F. 6.98 ppm (d resolved): —CH=CH—CH$_2$—N$^+$ E isomerism 8.07 (t), 8.29 (t): H in positions 6 and 7 of the quinolinium 8.24(dd): H in position 3 of the quinolinium 8.53: H in positions 5 and 8 of the quinolinium 9.34 (d): H in position 4 of the quinolinium 9.58 (d): H in position 2 of the quinolinium 7.31–9.19 and 9.5 to 9.7: mobile H's

EXAMPLE 4

The internal salt of [(±) (cis) (Z)]7-[3-[7-[[ (2-amino-4-thiazolyl)-[[carboxy-(3-chloro- 4,5-dihydroxy-phenyl]-methoxy]imino]-acetamido]-2-carboxy-8-oxo-5-thia-1-azabicyclo-[ 4,2,0]-oct.2-en-3-yl] 2(E)-propenyl]-thieno-[2,3-b]-pyridinium (R) or (S) or an (R+S) mixture STEP A: [3-chloro-4,5-bis-[(2-methoxy-ethoxy)-methoxy]-phenyl]-hydroxy acetic acid 3.34 g of lithium chloride and 9.64 g of potassium hydroxide were dissolved in 36 ml of water at 0° C. and a solution of 13.77 g of 3-chloro-4,5-bis-[(2-methoxy-ethoxy)-methoxy benzaldehyde (synthesized in Preparation 3). 3.74 ml of bromoform and 34 ml of dioxane were added to this mixture. The mixture was stirred for 24 hours at 0° C. and then another 3.74 ml of bromoform were added. The resultant mixture was stirred for 16 hours and after dilution in 100 ml of water and washing with ether. Decanting took place, followed by cooling to 0° C., acidifying to a pH of 2.5–3 and extracting with ether. The organic phase was washed with water, dried and the solvent was evaporated to obtain 13.95 g of the desired product in the form of a yellow oil.

Infrared analysis (CHCl$_3$):

1700 (max) and 1730 (shoulder) cm$^{-1}$: C=O 1599, 1578, 1489 cm$^{-1}$: aromatic nucleus NMR analysis of the proton (CDCl$_3$ 250 MHz in ppm):

3.38 (m) (6H): —OCH$_3$ 5.09 to 5.35 (m): —O—CH$_2$—O and Ar—CH(C=O)—O 7.05 to 7.78 ppm (m) (2H): Ar—H STEP B: Diphenylmethyl [3-chloro-4,5-bis-[(2-methoxy-ethoxy)methoxy]-phenyl]-hydroxy acetate 13.95 g of the acid of Step A were dissolved in 150 ml of ether at ambient temperature and under nitrogen and then 150 ml of a 0.3 molar solution of diphenyl-diazomethane in dichloromethane were added at 15° C. The mixture was stirred for 16 hours at ambient temperature and then, 30 ml of water were added, followed by decanting and acidifying with 30 ml of acetic acid. Washing took place again with a saturated solution of sodium bicarbonate, followed drying and evaporating the solvents. After chromatographing on silica eluting with a dichloromethane-methanol (99-1) mixture, 10 g of the desired product were obtained.

Infrared analysis (CHCl$_3$):

3535 cm$^{-1}$: non-phenolic —OH 1738 cm$^{-1}$: C=O of the ester function 1600, 1580, 1489 cm$^{-1}$: aromatic nucleus NMR analysis of the proton (CDCl$_3$ 250 MHz in ppm):

3.59 (m) and 3.47 (m) (4H), 3.75 (m) (2H) and 4.04 (m) (2H): O—CH$_2$—CH$_2$—O 3.38, 3.33 and 3.25 (m) (6H): —OCH$_3$ 5.02 to 5.30 (m): O—CH$_2$—O and Ar—CH(C=O)—O 6.8 to 7.35 (m): Ar—H STEP C: Diphenylmethyl [3-chloro-4,5-bis-[( 2-methoxy-ethoxy)-methoxy]-phenyl]-phthalimidoxy acetate 1 g of N-hydroxy phthalimide and 1.54 g of triphenyl phosphine were added to a solution of 1 g of the ester of Step B in 35 ml of tetrahydrofuran, followed by cooling to 10° C. Then, 1.58 g of diethyl azodicarboxylate (DEAD) were added dropwise and the mixture was stirred for 16 hours. After concentration of the solvents, chromatography on silica and eluting with a dichloromethane-methanol (99-1) mixture yielded. 3.09 g of the desired product in the form of a colorless oil (Rf=0.3).

Infrared analysis (CHCl$_3$):

1738, 1755 (shoulder) and 1795 cm$^{-1}$: C=O 1600, 1578, 1488 cm$^{-1}$: aromatic nucleus NMR analysis of the proton (CDCl$_3$ 250 MHz in ppm):

3.34 (s), and 3.36 (s): —OCH$_3$ 3.49 (m) (2H),3.57 (m) (2H), 3.77 (m) (2H) and 4.02 (m) (2H) ppm: O—CH$_2$—CH$_2$—O 5.22 (s) and 5.27 (s) ppm: —O—CH$_2$—O 5.91 (s) and 5.92 (s) ppm: Ar—CH(C=O)—O 6.92 (s) ppm: CO—O—CH—Ar$_2$ 7.75 ppm (m) (4H): Ar—H of the phthalimido 7.11 (m) and 7.21 to 7.33 ppm: the other aromatic H's STEP D: Diphenylmethyl aminoxy [3-chloro-4,5-bis-[( 2-methoxy-ethoxy)-methoxy]-phenyl]acetate 3 g of the product of Step C were dissolved under a nitrogen atomosphere in 40 ml of ethanol and the mixture was cooled to 5° C. Then, 0.224 ml of hydrazine hydrate were added and the mixture was stirred at 5° C. for half an hour, then returned to ambient temperature for 2 hours. After filtration and evaporation of the solvent, the desired product was obtained in the form of an oil with a Rf=0.3 [eluant: acetone-cyclohexane (3-7)].

Infrared analysis (CHCl$_3$):

3330 cm$^{-1}$: —NH$_2$ 1745 cm$^{-1}$: C=O 1600, 1578, 1488 cm$^{-1}$: aromatic nucleus +NH$_2$ NMR analysis of the proton (CDCl$_3$ 250 MHz in ppm):

3.34 (s) and 3.38 (s): —OCH$_3$ 3.48 (m), 3.58 (m), 3.76 (m) and 4.02 (m): O—CH$_2$—CH$_2$—O 5.17:Ar—CH(C=O)—O 5.80: mobile NH$_2$ 6.91 (s): CO—O—CH—Ar$_2$ 7.10 (m) (4H) and 7.21 to 7.33 (8H): Ar—H STEP E: 7-[3-[7β-[[[[[1-[3-chloro-4,5-bis-[ (2-methoxy-ethoxy)-methoxy]-phenyl]-2-oxo-2-(diphenyl methoxy)-ethyl]-oxy]-imino]-[ 2-(triphenylmethyl)-amino-thiazol-4-yl]-acetamido]-2-[( 4-methoxy-benzyloxy)-carbonyl]-8-oxo-5-thia-1-azabicyclo-[ 4,2,0]-[oct-2-en-3-yl]-2-propenyl]-thieno-[2,3-b]-pyridinium iodide 0.441 g of the product of Step D, 24 ml of methanol and 145 ml of p-toluene sulfonic acid were mixed under a nitrogen atmosphere for 5 minutes and a solution of 0.65 ml of 1-[3-[7β-[oxo-[ 2-[(triphenylmethyl)-amino]-thiazol-4-yl]-acetamido]-2-[ (4-methoxy-benzyloxy)-carbonyl]-8-oxo-5-thia-1-azabicyclo-[ 4,2,0]-[oct-2-en-3-yl]-2-propenyl]-thieno-[2,3-b]-pyridinium iodide (preparation 10) were added. Then, the mixture was stirred for 16 hours and after evaporation of the solvent, the residue was taken up in ether.

The precipitate was filtered, washed and dried to obtain 0.730 g of the desired product with a melting point of 135° C. (gum) and a Rf=0.3 [eluant: dichloromethane-methanol (9-1)].

STEP F: The internal salt of [(+) (cis (Z)]7-[3-[7-[[ (2-amino-4-thiazolyl)-[carboxy-(3-chloro-4,5-dihydroxy-phenyl)-methoxy]-imino]-acetamido]2-carboxy-8-oxo-5-thia-1-azabicyclo-[ 4,2,0]-oct-2-en-3-yl]-2(E) -propenyl]-thieno-[2,3-b]-pyridinium (R) or (S) or an (R+S) mixture A solution of 31 ml of trifluoroacetic acid in 8.5 ml of dichloromethane was poured at 0° C. into a mixture at 0° C. of 0.69 ml of the product of Step E, 17 ml of dichloromethylene and 3 ml of anisole and the mixture was stirred at this temperature for one hour. The solvents were eliminated, followed by crystallizing, filtering, washing and drying, chromatography and elution with an acetonitrile-water (1-1) mixture yielded 0.22 g of the desired product.

NMR analysis of the proton (DMSO 300 MHz in ppm):

3.19: C=C—CH$_2$—S— 5.01 (d) and 5.07 (d): CO—NH—CH (C=O)—CH—(N—)—S— 5.12 (s) and 5.17 (s): Ar—CH(CO—O—)—O— 5.52 (l): —CH=CH—CH$_2$—N$^+$, 5.60: CO—NH—CH(C=O)—CH—(N—)—S— (cis/H in position 6) 5.87 (m): —CH=CH—CH$_2$—N$^+$ E isomerism 6.78 to 6.86: —S—CHC(C=N—)—N=C(NH$_2$)— and Ar—H in ortho and para position of the Cl 7.21 and 7.41:—NH$_2$ 7.87 (d): H in position 3 of the thieno-[2,3-b]-pyridinium 8.10 (l): H in position 5 of the thieno-[2,3-b]-pyridinium 8.26 (d): H in position 2 of the thieno-[2,3-b]-pyridinium 9.03 (l): H in position 4 of the thieno-[2,3-b]-pyridinium 9.23: (l) H in position 6 of the thieno-[2,3-b]-pyridinium 9.74 (d): CO—NH—CH (C=O)—CH(N—)—S—

Using the procedure of Example 4, the products of preparations 1 to 12 were reacted to obtain the following compounds:

EXAMPLE 5

The internal salt of [[6R-[3(E), 6α, 7β(Z)]]7-[3-[7-[[ (2-amino-4-thiazolyl)-[carboxy-(3,4-dihydroxy- 5-nitro-phenyl)-methoxy]-imino]-acetamido]-2-carboxy-8-oxo-5-thia-1-azabicyclo-[ 4,2,0]-oct-2-en-3-yl]-2-propenyl]-thieno-[2,3-b]-pyridinium (R) or (S) or an (R+S) mixture NMR analysis of the proton 9DMSO 300 mHz in ppm):

3.49 to 3.9 (m) (C=C—CH$_2$—S— 3.14 (d) and 5.18 (d): CO—NH—CH(C=O) —CH—(N—)—S— 5.47 (s), 5.50 (s), 5.60 (s), 5.63 (s): Ar—CH—(CO—O—)—O— 6.67 (d): —CH=CH—CH —N$^+$ 5.77 (m): CO—NH—CH(C=O)—CH—(N—)—S— 6.29 (m): —CH=CH—CH—N$^+$ 6.80 (s), 6.83 (s), 7.64 (s) and 7.66 (s): —S—CH=C(C=N—) —N=C(NH$_2$)— 7.42 (d) and 7.47 (d): Ar—H in ortho position fo the nitro 7.1 to 7.2 (m): —CH=CH—CH—N$^+$ and Ar—H in para position of the nitro 7.89 (d): H in position 3 of the thieno-[2,3-b]-pyridinium 8.15 (dd): H in position 5 of the thieno-[2,3-b]-pyridinium 8.29 (d): H in position 2 of the thieno-[2,3-b]-pyridinium 9.09 (d): H in position 4 of the thieno-[2,3-b]-pyridinium 9.23 (d): H in position 6 of the thieno-[2,3-b]-pyridinium 9.54 (d res.), 9.65 (d) and 9.69 (d): CO—NH—CH—(C=O)—CH—(N—)—S— 10.42 (m): mobile H's

EXAMPLE 6

The internal salt of [(±) (cis) (Z)]7-[3-[7-[[(2-amino-4-thiazolyl)-[ carboxy-(3,4-dihydroxy-5-iodo-phenyl)-methoxy]-imino]-acetamido]- 2-carboxy-8-oxo-5-thia-1-azabicyclo-[4,2,0]-oct-2-en- 3-yl]-2-(E)-propenyl]-thieno-[2,3-b]

-pyridinium (R) or (S) or an (R+S) mixture

Analysis: $C_{30}H_{23}IN_6O_9S_3 + 1\ C_2HF_3O_2 + 1$ APTS

| | | | | | | | | | |
|---|---|---|---|---|---|---|---|---|---|
| Calculated: | % C | 41.78 | % H | 2.85 | % N | 7.5 | % S | 11.43 | % I | 11.3 |
| Found: | | 46.6 | | 2.8 | | 7.8 | | 12.0 | | 10.9 |

NMR analysis of the proton (DMSO 300 MHz in ppm):
3.70: C=C—CH$_2$—S— 5.11 (s) and 5.17 (s) (1H): CO—NH—CH(C=O)—CH—(N—)—S— 5.29 (s) and 5.32 (s): Ar—CH (CO—O—)—O— 5.67 (d): —CH=CH—CH$_2$—N$^+$, 5.75 (m): CO—NH—CH(C=O)—CH(N—)—S— 6.29: —CH=CH—CH$_2$—N$^+$ E isomerism 6.77 (resolved) (1H): —S—CH=C(C=N—)—N=C(NH$_2$)— 6.90 (2H): Ar—H in ortho and para position of I 7.89 (d): H in position 3 of the thieno-[2,3,-b]-pyridinium 8.15 (dd): H in position 5 of the thieno-[2,3-b]-pyridinium 8.29 (d): H in position 2 of the thieno-[2,3-b]-pyridinium 9.09 (d): H in position 4 of the thieno-[2,3-b]-pyridinium 9.13 (d): H in position 6 of the thieno-[2,3-b]-pyridinium 9.37 (sl): CO—NH—CH(C=O)—CH(N—)—S—

EXAMPLE 7

The internal salt of [(±) (cis) (Z)]7-[3-[7-[[(2-amino- 4-thiazolyl)-[crboxy-(3,4,5-trihydroxy-phenyl)-methoxy]-imino]-acetamido]- 2-carboxy-8-oxo-5-thia-1-azabicyclo-[4,2,0]-oct-2-en- 3-yl]-2(E)-propenyl]-thieno-[2,3-b]-pyridinium (R) or (S) or an (R+S) mixture NMR analysis of the proton (DMSO 300 MHz in ppm):
5.15 (d) and 5.17 (d) (1H): CO—NH—CH(C=O)—CH—(N—)—S—[2/5 (R/S) 3/5] 5.22 and 5.34 (2H): Ar—CH(CO—O)—O— 5.67 (d): —CH=CH—CH$_2$—N$^+$, 5.76 (m), 6.20 to 6.49 (m): CO—NH—CH(C=O)—CH(N—)—S—, CH=CH—CH$_2$—N$^+$ and Ar—H of the triphenol 6.75, 6.77, 6.87 and 6.90 (1H): —S—CH=C(C=N—)—N=C(NH$_2$)— 7.74 (d): H in position 5 of the thieno-[2,3-b]-pyridinium 7.89 (d) and 8.28 (d): H in positoins 4 and 3 of the thieno-[2,3-b]-pyridinium 8.10 to 8.27, 9.09 and 9.23: H in positions 2 and 6 of the thieno-[2,3-b]-pyridinium 9.6 to 9.85: CO—NH—CH(C=O)—CH(N—)—S—

EXAMPLE 8

The internal salt of [(±) (cis) (Z)]7-[3-[7-[[(2-amino- 4-thiazolyl)-[carboxy-(2-chloro-3,4-dihydroxy-phenyl)-methoxy]-imino]-acetamido]- 2-carboxy-8-oxo-5-thia-1-azabicyclo-[4,2,0]-oct- 2-en-3-yl]-2(E)-propenyl]-thieno-[2,3-b]-pyridinium (R)or (S) or an (R+S) mixture Analysis: $C_{30}H_{23}IN_6O_9S_3$+2 APTS Found: %C 46.8 %H 2.55 %N 8.53 %S 9.76 %Cl 3.59

NMR analysis of the proton (DMSO 300 MHz in ppm):
3.5 to 3.9 (m): C=C—CH$_2$—S— 5.17 (m) (1H): CO—NH—CH(C=O)—CH—(N—)—S— 5.67 (dl): —CH=CH$_2$—CH—N$^+$, 5.70 to 5.90 (2H): CO—NH—CH(C=O)—CH(N—)—S—+other H 6.33 (m): —CH=CH—CH$_2$—N$^+$ E isomerism 6.79 (m) and 6.96 (m) (4H): 4H 7.89 (d) and 8.29 (d): H in positions 2 and 3 of the thieno-[2,3-b]-pyridinium 8.14 (m): H in position 5 of the thieno-[2,3-b]-pyridinium 9.08 (d): H in position 4 of the thieno-[2,3-b]-pyridinium 9.26 (d): H in position 6 of the thieno-[2,3-b]-pyridinium

EXAMPLE 9

The internal salt of [[6R-[3(E), 6α, 7β(Z)]]7-[3-[7-[[ (2-amino-4-thiazolyl)-[carboxy-(2,5-dichloro- 3,4-dihydroxy-phenyl)-methoxy]-imino]-acetamido]-2-carboxy-8-oxo-5-thia-1-azabicyclo-[ 4,2,0]-oct-2-en-3-yl]-2-propenyl]-thieno-[2,3-b]-pyridinium (R) or (S) or an (R+S) mixture NMR analysis of the proton (DMSO 300 MHz in ppm):
5.20: Ar—H in ortho position of the Cl 5.79: Ar—CH (CO—O—)—O— 5.78 (m): —CH=CH—CH$_2$—N$^+$, 6.31: —CH=CH—CH$_2$—N$^+$ 7.88: H in position 3 of the thieno-[2,3-b]-pyridinium 8.15 (m): H in position 5 of the thieno-[2,3-b]-pyridinium 8.98 (m): H in position 2 of the thieno-[2,3-b]-pyridinium 9.09 (d): H in position 4 of the thieno-[2,3-b]-pyridinium 9.12 (d): H in position 6 of the thieno-[2,3-b]-pyridinium

EXAMPLE 10

The internal salt of [[6R-[3(E), 6α, 7β(Z)]]7-[ 3-[7-[[(2-amino-4-thiazolyl)-[carboxy-(3-cyano- 4,5-dihydroxy-phenyl)-methoxy]-imino]-acetamido]-2-carboxy-8-oxo-5-thia-1-azabicyclo-[4,2,0]-oct-2-en-3-yl]-2-propenyl]-thieno-[2, 3-b]-pyridinium (R) or (S) or an (R+S) mixture NMR analysis of the proton (DMSO 300M MHz in ppm):
3.19: C=C—CH$_2$—S— 5.15 (D) and 5.20 (d): CO—NH—CH(C=O)—CH—(N—)—S— 5.40 (s): Ar—CH (CO—O—)—O— 5.67 (d): —CH=CH—CH$_2$—N$^+$, 5.81 (m): CO—NH—CH(C=O)—CH(N—)—S— 6.67 (S): —S—CH=C(C=N—)—N=C(NH$_2$)— 7.10 to 7.20 (m) (3H): Ar—H and CH= 7.34 (m), 10.27 to 10.42 (m): mobile H's 7.89 (d): H in position 3 of the thieno-[2, 3-b]-pyridinium 8.15 (dd): H in position 5 of the thieno-[2, 3-]-pyridinium 8.28 (d): H in position 2 of the thieno-[2,3-b]-pyridinium 9.09 (d): H in position 4 of the thieno-[2,3-b]-pyridinium 9.23 (d): H in position 6 of the thieno-[2,3-b]-pyridinium 9.52 (d) and 9.62 (d): CO—NH—CH(C=O)—CH—(N—)—S—

EXAMPLE 11

The internal salt of [[6R-[3(E), 6α,7β(Z)]]7-[3-[ 7-[[(2-amino-4-thiazolyl)-[carboxy-(3,4-dihydroxy- 5-methoxy-phenyl)-methoxy]-imino]-acetamido]-2-carboxy-8-oxo-5-thia-1-azabicyclo-[4,2,0]oct- 2-en-3-yl]-2-propenyl]-thieno-[2,3-b]-pyridinium (R) or (S) or an (R+S) mixture The (R) and (S) isomers were separated by HPLC (Microbondapack column C18 ), solvent: Water/acetonitril (85/15)

(S) Isomer

NMR analysis of the proton (DMSO 300 MHz in ppm):
3.71 (s): Ar—OCH$_3$ 5.16 (d J=5): CO—NH—CH(C=O)—CH—(N—)—S— 5.32 (s): Ar—CH(CO—O—)—O— 5.68 (d): —CH=CH—CH$_2$—N$^+$, 5.79 (dd J=5 and 7.5): CO—NH—CH(C=O)—CH(N—)—S— 6.28 (m): —CH=CH—CH$_2$—N$^+$, 6.55 (s) (2H): Ar—H in ortho and para position of the —OMe 6.78 (s): —S—CH=C(C=N—)—N=C(NH$_2$)— 7.11 (d): —CH=CH—CH$_2$—N$^+$, 7.29 (m), 8.38 (m), 8.99 (m): mobile H's 7.88 (d): H in position 3 of the thieno-[2,3-b]- pyridinium 8.15 (dd): H in position 5 of the thieno-[2,3-b]-pyridinium 8.29 (d): H in position 2 of the thieno-[2,3-b]-pyridinium 9.08 (d): H in position 4 of the thieno-[2,3-b]-pyridinium 9.22 (d): H in position 6 of the thieno-[2,3-b]-pyridinium 9.55 (d): CO—NH—CH(C=O)—CH(N—)—S—

(R) Isomer

NMR analysis of the proton (DMSO 300 MHz in ppm): 3.50 (s) (partly masked): C=C—CH$_2$—S— 3.72 (s): Ar—OCH$_3$ 5.19 (d J=5): CO—NH—CH(C=O)—CH—(N—)—S— 5.32 (s): Ar—CH(CO—O—)—O— 5.68 (d J=6): —CH=CH—CH$_2$—N$^+$ 5.76 (dd J=5 and 7.5): CO—NH—CH(C=O)—CH(N—)—S— 6.29 (m): —CH—CH—CH$_2$—N$^+$, 6.55 (s) and 6.57 (s) (2H): ar—H in ortho and para position of the —OMe 6.74 (s): —S—CH=C(C=N—)—N=C(NH$_2$)— 7.15 (d): —CH=CH—CH—N$^+$, 7.30 (m) (2H), 8.39 (S) (1H), 8.96 (s) (1H): mobile H's 7.89 (d): H in positio 3 of the thieno-[2,3-b]-pyridinium 8.15 (dd): H in position 5 of the thieno-[2,3-b]-pyridinium 8.29 (d): H in position 2 of the thieno-[2,3-b]-pyridinium 9.08 (d): H in position 4 of the thieno-[2,3-b]-pyridinium 9.23 (d): H in position 6 of the thieno-[2,3-b]-pyridinium 9.62 (d): CO—NH—CH (C=O)—CH (N—)—S—

EXAMPLE 12

The internal salt of [[6R-[3(E), (6α, 7β(Z)]]1-[3-[ 7-[[(2-amino-4-thiazolyl)-[carboxy-(2,5-dichloro- 3,4-dihydroxy-phenyl]-methoxy]-imino]-acetamido]-2-carboxy-8-oxo-5-thia- 1-azabicyclo-[4,2,0]-oct-2-en-3-yl]-2propenyl]-quinolinium (R) or (S) or (R+S) mixture

EXAMPLE 13

The internal salt of [[6R-[3(E), 6α,7β(Z)]]2-[3-[7-[ [(2-amino-4-thiazolyl)-[carboxy-(2,5-dichloro- 3,4-dihydroxy-phenyl)-methoxy]-imino]-acetamido]-2-carboxy-8-oxo-5-thia-1-azabicyclo-[ 4,2,0]-oct-2-en-3-yl]-2-propenyl] isoquinolinium (R) or (S) or an (R+S) mixture Rf=0.6 (eluant: acetone-water

EXAMPLE 14

The internal salt of [[6R-[3(E), 6α,7β-(Z)]]1-[3-[ 7-[[(2-amino-4-thiazolyl)-[carboxy-(2,5-dichloro- 3,4-dihydroxy-phenyl)-methoxy]-imino]-acetamido]-2-carboxy-8-oxo-5-thia-1-azabicyclo-[ 4,2,0]-oct-2-en-3-yl]-2-propenyl]-4-(methylthio) pyridinium (R) or (S) or an (R+S) mixture
Rf=0.6 (eluant: acetone-water (8-2))

EXAMPLE 15

The internal salt of [(+) (cis (Z)7-[3-[7-[[(2-amino- 4-thiazolyl)[carboxy-(3-bromo-4,5-dihydroxy-phenyl)-methoxy]-imino]-acetamido]- 2-carboxy-8-oxo-5-thia-1-azabicyclo-[4,2,0]-oct-2 -en- 3-yl]-2-(E)-propenyl]-thieno-[2,3-b]-pyridinium (R) or (S) or an mixture

EXAMPLE 16

Internal salt of (6R (3(E), 6α, 7β(Z))) 1-(3-(7-(((2-amino-4-thiazolyl)-(carboxy-(2,3-dihydroxy- 4-fluorophenyl)-methoxy)-imino)-acetamido)-2 -carboxy-8-oxo-5-thia-1-azabicyclo-(4,2,0)-oct- 2-en-3 -yl)-2-propenyl) quinolinium
STEP A: Diphenylmethyl [4-fluoro-(2,3-bis-hydroxy-phenyl]-hydroxy-acetate 480 ml of a 0.3M solution of diphenyl diazomethane were added over 2 hours to a solution of 47.7 g of the product of Preparation 11 in 500 ml of ethyl ether cooled to –10° C. The temperature was taken to –5° C. and 10 ml of acetic acid were added and the solution was used as is in the following steps.

STEP B: Diphenylmethyl [4-fluoro-[2,3-bis-[( 2-methoxy-ethoxy)-methoxy]-phenyl]-hydroxy-acetate 238 ml of diisopropylethylamine were added to the solution of Step A and the ether was replaced by 500 ml of methylene chloride. Then, the mixture was cooled to 6° to 10° C. and 53 ml of methoxyethoxymethyl chloride were added over 75 minutes. The mixture was stirred for 75 minutes and 500 ml of water were added, followed by decanting. The organic phase was washed with N hydrochloric acid, then with N sodium hydroxide and with water, followed by drying and evaporating to dryness. The residue was chromatographed on silica and eluted with an ethyl acetate-hexane (1-1) mixture to obtain 26.1 g of crude product which was chromatographed again on silica, eluant: methylene chloride-acetone (97-3) to obtain 14.58 g of the desired product.

NMR Spectrum: CDCl$_3$ 300 MHz in ppm:
3.34–3.36: the C—O—Me's; 3.52–3.80–3.91: the O—CH$_2$—CH$_2$—O's; 4.06 (dJ=6.5); mobile H; 5.17 to 5.27; the O—CH$_2$—O's; 5.49 (dJ=7.5): the C$_6$H$_5$—CH—O's; 6.84 (dd: J=9 and 10): H$_6$; 6.96 (dd J=9 and 6): H$_5$; 7.20 to 7.40 and 6.94 (sl): the aromatics.

STEP C: Diphenylmethyl [4-fluoro-2,3-bis-[( 2-methoxy-ethoxy)-methoxy]-phenyl]-phthalimidoxy acetate Using the procedure of Step C of Example 4, 14.42 g of the product of Step B were reacted to obtain after chromatography on silica, eluant methylene chloride-methanol (99-1), 11.89 g of the desired product.

IR Spectrum CHCl$_3$
1792–1756–1734 cm$^{-1}$: C=O; 1600–1492 cm$^{-1}$: aromatic.

NMR Spectrum: CDCl$_3$ 250 MHz: for 2 OMEM groups:
3.30 (s), 3.34 (s): OCH$_3$; 3.47 (m) 3.84 (m): O—CH$_2$—CH$_2$—O; 5.10–5.27; O—CH$_2$O; then 6.39 (s): AR—CH(ON=)—CO$_2$; 6.95 (s) CO$_2$CH(C$_6$H$_5$)$_2$; 6.84 (t): H$_5$; 7.15 (2H) 7.19–7.32 (9H) 7.74 (4H): aromatic H's.

STEP D: Diphenylmethyl aminoxy [4-fluoro-2,3-bis-[ 2-methoxy-ethoxy)-methoxy]-phenyl]-acetate 0.88 ml of hydrazine hydrate were added over one hour at –10° C. to a solution of 11.27 g of the product of Step C, 112.7 ml of tetrahydrofuran and the mixture was stirred for 90 minutes at The insoluble part was filtered off and the filtrate was concentrated to dryness. The residue was chromatographed on silica (eluant: methylene chloride-ethyl acette (80-20)) to obtain 4.72 g of the desired product.

NMR Spectrum: CDCl$_3$ 200 MHz:
3.35 (s) 3.36 (s): OCH$_3$; 3.54 (m) (4H) 3.93 (m) (4H): O—CH$_2$—CH$_2$O; 5.20 (s) 5.27 (s): OCH$_2$O; 6.78 (dd J=9.5 and 9): H$_5$; 6.89 (m): H$_6$; 5.73 (s): Ar—CH (ONH$_2$)—CO$_2$; 6.94 (s): CO$_2$—CH—(C$_6$H$_5$)$_2$; 7.10 (m) (5H): 10 aromatic H's (C$_6$H$_5$)$_2$.

STEP E: [[[1-[4-fluoro-2,3-bis-[( 2-methoxy-ethoxy)-methoxy]-phenyl]-2-oxo-2-(diphenylmethoxy)-ethyl]-oxy]-imino]-[ 2-[(triphenylmethyl)-amino]-amino]-thiazol-4-yl]-acetic acid Using the procedure of Step E of Example 1, 4.65 g of the product of Step D and 3.45 g of oxo-[2-[ (triphenylmethyl)-amino]-thiazol-4-yl]-acetic acid (Belgium Patent Application No. 864,828) were reacted to obtain after chromatography on silica (eluant: methylene chloride-methanol (96-4)) 6.5 g of the desired product.

IR Spectrum (CHCl$_3$):

3410 cm$^{-1}$; =CH—NH—; 1781 cm$^{-1}$: C=O; 1618, 1607, 1528, 1496 cm$^{-1}$: $CO_2$, aromatic and heteroaromatic.

NMR Spectrum: DMSO 300 MHz:

3.18 (s)-3.20 (s): $OCH_3$; 3.43 (m) (4H) 3.81 (m) 4H): O—$CH_2$—$CH_2$—O; 5.17 (s) (2H) 5.21 (s) (2H): O—$CH_2$—O; 5.87 (s) (3/4H): ArCH(O—$NH_2$) —$CH_2$—; 6.68 (s) (3/4 H): $H_5$ thiazole; 6.84 (s) (3/4H): $CO_2CH(C_6H_5)_2$; approx. 6.95–7.0: $H_5$ $H_6$; approx. 7.18–7.50: other aromatics; 8.65 (sl): =C—NH.

STEP F: 4-methoxy-benzyl 7β-[[[[[1-[4-fluoro-2,3-bis-[( 2-methoxy-ethoxy)-methoxy]-phenyl]-2-oxo- 2-(diphenyl-methoxy)-ethyl]-oxy]-imino-[2-(triphenyl-methyl)-amino]-thiazol- 4-yl]-acetamido]-3-[(Z)-3-chloro-1-propenyl]-8-oxo-5-thia-1-azabicyclo-[4,2,0 ]-oct-2-en-2-carboxylate Using the procedure of Step F of Example 1 but at a temperature of –10° C., 6.44 g of the product of Step E were reacted to obtain after chromatography on silica [eluant: methylene chloride-ethyl acetate (90-10)], 5.35 g of the desired product were obtained.

NMR Spectrum: (CDCl$_3$ 400 MHz):

3.05 (d, 1H)-3.20 (d,1H): $CH_2$S; [3.24 (s), 3.26 (s)](3H) 3.35 (s, 3H): $OCH_3$; 3.43 (m, 2H)-3.55 (m, 2H)-3.70–4.15: ($CH_2CH_2$O and =CH—$CH_2$Cl; 3.81 (s): $CH_3$OAr; 4.96 (d) -4.97 (d): $H_6$ cephalo; 5.12 5.31 (6–7H): $OCH_2$O, $CO_2CH_2$Ar, ArCH(ONH$_2$)—$CO_2$—; 5.81 (m): $H_7$ cephalo; 5.75 (m): CH=CH—$CH_2$Cl (Z); 6.26 (d, J=11)-6.29 (d, J=11): —CH=CH—$CH_2$Cl (Z); approx. 6.77: $H_5$ thiazole; approx. 6.85–7.45: aromtic H's +$CO_2CH(c_6h_5)_2$; 7.85–8.20: NH.

STEP G: 4-methoxhy-benzyl 7β-[[[[[1-[4-fluoro-2,3-bis [( 2-methoxyethoxy)-methoxy]-[phenyl]-2-oxo-2- (diphenyl-methoxy)-ethyl]-oxy]-imino]- 2-(triphenyl-methyl)-amino]-thiazol-4-yl]-acetamido]-3-[ (Z)-3-iodo-1-propenyl] -8-oxo-5-thia-1-azabicyclo-[4,2,0]-oct-2-en- 2-carboxylate Using the procedure of Step G of Example 1, 1.2 g of the product of Step F wree reacted to obtain 1.05 g of the desired product.

NMR Spectrum:

3.23 (s) 3.26 (s) 3.35 (s): $CH_3$O; aporox. 3.50 to 3.95:O—$CH_2$—$CH_2$—O of which 3.81: $CH_3$OAr; approx. 4.0: =CH—$CH_2$—I; 4.92 (m): $H_6$ cephalo; 5.16–5.30: $OCH_2$O, $CO_2CH_2$Ar; 5.50 (m): $H_7$ cephalo; 6.12 (m): =CH—$CH_2$I (E); 6.42 (s) 6.44 (s): Ar—CH(ONH$_2$)$CO_2^-$; 6.66 (t,J=9, approx.=0.5H): aromatic H in ortho position of F; 6.76 (s resolved): $H_5$ thiazole; 6.77–7.45: aromatic H's; 7.95 (d) 8.25 (d): NH.

STEP H: 1-[3-[7β-[[[[[1-[4-fluoro-2,3-bis-[( 2-methoxy-ethoxy)-methoxy]-phenyl]-2-oxo-2-(diphenylmethoxy)-ethyl]-oxy]-imino]- 2-triphenylmethyl)-amino]-thiazol-4-yl]acetamido]-2-[( 4-methoxybenzyloxy)carbonyl]-8-oxo-5-thia-1-azabicyclo-[ 4,2,0]-[oct-2-en-3-yl]-2-propenyl quinolinium iodide Using the procedure of tep H of Example 1, 1.02 g of the product of Step G and 0.46 g of quinoline were reacted to obtain after chromatography on silica, eluant: methylene chloride-methanol (97-3), 347 mg of the desired product (50/50 mixture of the two R and S isomers of expected product).

NMR Spectrum: (CDCl$_3$ 400 MHz):

3.20 (s) 3.26 (s) 3.34 (s) 3.35 (s): $CH_3$O; 3.79 (s) 3.80 (s): $CH_3$OAr; 3.42 (m) 3.54 (m) 3.79 (m) 3.90 (m): $OCH_2CH_2$O; 4.89 (d): $H_6$ cephalo; 5.12 to 5.28: $OCH_2$O, $CO_2CH_2$Ar; 5.77 (dd) resolved) $H_7$ cephalo; 6.00 (dd) 6.13 (dd): =CH—$CH_2$—N$^+$=; 6.38 (s) 6.44 (s): Ar—CH—(O—)$CO_2^-$; 6.51 (m ): =CHCH$_2$ (E); 6.72 (resolved) $H_5$ thiazole; 6.70 to 7.15 $H_5$–$H_6$ fluorophenyl, CH=CH—$CH_2$, $CO_2CH(C_6H_5)_2$; approx. 7.30: aromatic H's $(C_6H_5)_3$—C.

STEP I: Internal salt of (6R(3(E), 6α, 7β(Z))) 1-(3-(7-((( 2-amino-4-thiazolyl)-(carboxy-(2,3-dihydroxy-4-fluorophenyl)-methoxy)-imino)-acetamido)- 2-carboxy-8-oxo-5-thia-1-azabicyclo [4,2,0]-oct-2-en-3-yl)-2-propenyl)-quinolinium Using the procedure of Step I of Example 1, 339 mg of the product of Step H and 5 ml of a solution of trifluoroacetic acid with 10% anisole to obtain 180 mg of the desired product.

NMR Spectrum: DMSO 300 MHz:

5.15 (d resolved) $H_6$ cephalo; 5.75 (dd) approx. 5.811–5.95: $H_7$ cephalo, =CH—$CH_2$N$^+$=, Ar—CH(—O—)$CO_2$; 6.38 (m): CH=CH—$CH_2$ (E); 6.99 (d resolved J=16): CH=CH—$CH_2$ (E); 6.59 (d resolved J=10): $H_5$ fluorophenyl; 6.75–6.81: $H_6$ and $H_5$ thiazole; 7.35 (wide): $NH_2$ and/or $C_6H_5$; 8.07 (t, 1H) 8.26 (m, 2H), 8.52 (d, 1H) 8.56 (dd, 1H) 9.30 (d, 1H) 9.58 (sl, 1H): quinoline; approx.= 10.50: OH; 9.46 (d): CONH.

EXAMPLE 17

Internal salt of (6R(3 (E), 6α,7β-(Z))) 7-(3-(7-((( 2-amino-4-thiazolyl)-(carboxy-(2,3-dihydroxy-4-fluorophenyl)-methoxy)-imino)-acetamido)- 2-carboxy-8-oxo-5-thia-1-azabicyclo (4,2,0) oct-2-en-3-yl)- 2-propenyl)-thieno-(2,3,-b) pyridinium STEP A: 1-[3-[7β-[[[[[1-[4-fluoro-2,3-bis-[ (2-methoxyethoxy)-methoxy]-phenyl]-2-oxo-2-(diphenyl-methoxy)-ethyl]-oxy]-imino]-[ 2-(triphenylmethyl)-amino]-thiazol-4-yl]-acetamido]-2-[( 4-methoxy-benzyloxy-carbonyl]-8-oxo-5-thia-1-azabicyclo-[4,2,0]-[oct- 2-en-3-yl]-2-propenyl-thieno-(2,3-b) pyridinium iodide Using the procedure of Step H of Example 16, 944 mg of the product of Step G of Example 16 and 0.45 g of thieno-[2,3-b]pyridine were reacted to obtain 339 mg of the desired product after chromatographing on silica (eluant: methylene chloride-methanol (95-5)).

NMR Spectrum: CDCl$_3$ 300 MHz:

3.20 () 3.27 (s) 3.34 (s) 3.35 (s): $OCH_3$; 3.40–3.60 and 3.77–4.00: $OCH_2CH_2$O, $CH_2$S; 3.79 (s) 3.80 (s): ArOCH]; 4.92 (d, J=5) 4.99 (d, J=5): $H_6$ cephalo; approx. 5.18–5.30: $OCH_2$O, $CO_2CH_2$Ar; approx. 5.77 (m): $H_7$ cephalo; 5.68 (m) 5.96 (m): =CH—$CH_2$N$^+$=; 6.39 (s) 6.45 (s): ArCH(—O—$CO_2^-$; 6.73 (s) 6.74 (s): $H_5$ thiazole; approx. 6.77 (t, resolved): $H_5$ fluorophenyl; 6.90 to 7.40: benzene H's, $CO_2CH(C_6H_5)_2$, CH=CH—$CH_2$(E); 6.92 (m): CH=CH—$CH_2$(E); 7.54 (d) 7.66 (d): $H_3$' and 7.83–7.87: $H_2$', and 8.06 (m): $H_5$' and 8.80 (d): $H_4$' and 10.05 (m): $H_6$' and 8.23 (d): CONH of the thieno [2,3-b]pyridine.

STEP B: Internal salt of (6R(3(E), 6α, 7β(Z))) -7-(3-(7-((( 2-amino-4-thiazolyl)-(carboxy-(2,3-dihydroxy-4-fluorophenyl)-methoxy)-imino)-acetamido)-2-carboxy-8-oxo-5-thia-1-azabicyclo-[ 4,2,0]-oct-2-en-3-yl) -2-propenyl)-thieno (2,3-b) pyridinium Using the procedure of Step I of Example 16, 332 mg of the product of Step A were reacted to obtain 164 mg of the desired product.

NMR Spectrum DMSO 300 MHz:

5.18 (d) resolved: $H_6$ cephalo; 5.67 (d) =CH—$CH_2$—N=; 5.77–5.90: $H_7$ cephalo, Ar—CH(—O—) $CO_2^-$; 6.31 (m): CH=CH—$CH_2$ (E); 7.14 (d, J=15): CH=CH—$CH_2$(E); approx. 6.80 (m): $H_5$ thiazole, $H_5$ fluorophenyl; 7.36 (wide): $NH_2$: 6.59 (t, J=9): $H_6$; 7.89 9d, J=6) 8.15 (dd) 8.28 (d, J=6) 9.09 (d) 9.23 (d): $H_3$' $H_5$' $H_2$' $H_4$' $H_6$ of the thieno [2,3-b ]pyridine.

EXAMPLE 18

Internal salt of (6R(3(E), 6α, 7β(Z)))-1-(3-(7-((( 2-amino-4-thiazolyl)-(carboxy-(2,3-dihydroxy- 4-fluorophenyl)-methoxy)-imino)-acetamido)-2-carboxy-8-oxo-5-thia-1-azabicyclo (4,2,0) oct-2-en-3-yl)-2-propenyl) -4-(methylthio) pyridinium STEP A: 1-[3-[7β-[[[[[1-[4-fluoro-2,3-bis-[ (2-methoxy-ethoxy)-methoxy]-phenyl]-2-oxo-2-(diphenyl-methoxy)-ethyl]-oxy]-imino] [2 -(triphenylmethyl)-amino]-thiazol-4-yl]-acetamido]-2-[ (4-methoxy-benzyloxy-carbonyl]-8-oxo-5-thia-1-azabicyclo-[4,2,0]-oct-2-en- 3-yl]-2-propenyl-4-(methylthio) pyridinium iodide Using the procedure of Step H of Example 16, 1.052 g of the product of Step G of Example 16 and 462 mg of 4-thiomethyl pyridine wre reacted to obtain 536 mg of the desired product after chromatography on silica (eluant: methylene chloride-methanol (95-5)).

NMR Spectrum: $CDCl_3$ 400 MHz:

2.61 (s): $CH_3S$; 3.21 (s) 3.26 (s) 3.34 (s) 3.35 (s): $OCH_3$; 3.79 (s) 3.88 (s): $CH_3OAr$; 3.43 (m) 3.54 (m) 3.80–4.00: $CH_2S$, $OCH_2CH_2O$; 4.92 (d): $H_6$ cephalo; 5.70 (dd) +5.77 (dd) $H_7$ cephalo; 533 (m) 5.54 (m): $CH_2N^+=$; 5.17 5.30: $OCH_2O$, $CO_2CH_2Ar$; 6.33 (m): $CH=CH—CH_2$ (E); 6.35 (s): $ArCH(—O—)CO_2—$; 6.74 (s) 6.75 (w): $H_5$ thiazole; 6.72 to 7.18: $H_5$, $H_6$ fluorophenyl, $CO_2CHC_6H_5$, rH aromatic, $CH=CH—CH_2$ (E) ; 7.20 to 7.38: aromatic H $C—(C_6H_5)_3$, $(C_6H_5)_2$——$CH_2—CO_2$; 7.61 (d, 2H) 8.8 (m, 2H): $H_3'$, $H_5'$ and $H_2'$, $H_6'$ of the pyridinium; 7.83 (d), 8.15 (d): —CONH.

STEP B: Internal salt of (6R(3(E), 6α, 7β-(Z))-1-(3-(7-((( 2-amino-4-thiazolyl)-(crboxy-(2,3-dihydroxy- 4-fluorophenyl)-methoxy)-imino)-acetamido)-2-carboxy-8-oxo-5-thia-1-azabicyclo (4,2,0) oct-2-en-3-yl)-2-propenyl)-4-(methylthio) pyridinium Using the procedure of Step I of Example 16, 500 mg of the product of Step A were reacted to obtain 251 mg of desired product.

NMR Spectrum DMO 300 MHz:

3.50–3.70: $CH_2S$; 2.72 (s): $CH_3S$; 5.18 (m): $H_6$ cephalo; approx.=5.77 (m): $H_7$ cephalo; 5.24 (m): $=CH—CH_2—N=$; 5.83 (s), 5.87 (s): $OCH_2O$, $ArCO_2CH_2$; 6.28 (m): $CH=CH—CH_2(E)$; 6.98 (d, J=16): $CH=CH—CH_2$; 6.61 (t, resolved): $H_6$ fluorophenyl; 6.77 6.82: $H_5$ and $H_6$ thiazole; 7.32: $NH_2$; 7.96 (d) 8.71 (d): $H_3'$ $H_5'$ and $H_2'$ $H_6'$ of the pyridinium.

EXAMPLE 19

Internal salt of (6r(3(E), 6α, 7β(Z)))-2-(3-(7-((( 2-amino-4-thiazolyl)-(carboxy-(2,3-dihydroxy-4-fluorophenyl)-methoxy)-imino)-acetamido)- 2-carboxy-8-oxo-5-thia-1-azabicyclo (4,2,0) oct-2 -en-3-yl)-2-propenyl) isoquinolinium STEP A: 1-[3-[7β-[[[[[1-[4-fluoro-2,3-bis-[( 2-methoxy-ethoxy)methoxy]-phenyl]-2-oxo-2-(diphenyl-methoxy)-ethyl]-oxy]-imino]- 2-(triphenyl methyl)-amino]-thiazol-4-yl]-acetamido]-2-[ (4-methoxy-benzyloxy-carbonyl]-8-oxo-5-thia-1-azabicyclo-[4,2,0]-[oct-2-en- 3-yl]-2-propenyl isoquinolinium iodide Using the procedure of Step H of Example 16, 917 mg of the product of Step G of example 16 and 416 mg of isoquinoline were reacted to obtain 473 mg of desired product after chromatography on silica (eluant: methylene chloride-methanol (96.4)).

NMR Spectrum: $CDCl_3$ 300 MHz:

3.20 (s) 3.26 (s) 3.34 (s) 3.35 (s): $CH_3O$; 3.76 (s) 3.78 (s): $ArOCH_3$; 3.40–4.00:$OCH_2—CH_2O$, $CH_2S$; $H_6$ cephalo; 5.80 (m): $H_7$ cephalo; approx. 5185.30: $OCH_2O$, $ArCO_2CH_2$; approx. 6.48 (m): $CH_2—CH(E)$; 6.38 (s) 6.44 (): Ar—CH(—O—)$CO_2—$; 6.73 (s) 6.75 (s): $H_5$ thiazole; approx.=6.76 to 7.49: aromatic H's (phenyl groups), $CO_2CH(C_6H_5)_2$; 7.96 (m, 1H) 8.10 (m, 2H) 8.26 (m, 2H) 8.49 (m, 1H) 8.69 (m, 1H) 10.90 (s resolved, 1h): of the isoquinoline.

STEP B: Internal salt of (6R(3(E), 6α, 7β(Z))) 2-(3-(7-((( 2-amino-4-thiazolyl)-(carboxy-(2,3-dihydroxy- 4-fluorophenyl)-methoxy)-imino)-acetamido)- 2-carboxy-8-oxo-5-thia-1-azabicyclo (4,2,0) oct-2-en-3-yl)-2-propenyl) isoquinolinium Using the procedure of Step I of Example 16, 460 mg of the product of Step A were reacted to obtain 176 mg of the expected product.

NMR Spectrum: DMSO 400 MHz:

3.72 (m): $CH_2S$; 5.18 (d, resolved): $H_6$ cephalo; 5.77 (dd,d after exchange) -$H_7$ cephalo; 5.52 (m): $CH_2—N^+=$; 5.83 (s), 5.87 (s): Ar—$CH_2$ (—O—) $CO_2^-$; 6.39 (m): $CH=CH—CH_2(ΔE)$; 7.10 (d, J=10): $CHCH—CH_2$ (E); 6.59 (m), 6.80 (m): $H_6$, $H_5$ fluorophenyl; 6.77 (s) 6.80 (s): $H_5$ thiazole; 8.09 (t) 8.28 (t) and 8.37 (d) 8.53 (d) 8.61 (d) 8.74 (m) 10.06 (s): $H_6'$-$H_7'$ and $H_3'$ $H_4'$ and $H_5'$ and $H_8'$ and $H_1'$ of the isoquinoline.

EXAMPLE 20

Internal salt of (6R(E(E) 6α, 7β(Z))) 1-(3-(7-((( 2-amino-4-thiazolyl)-(carboxy-(2,3-dihydroxy- 4-fluorophenyl)-methoxy)-imino)acetamido)-2-carboxy-8-oxo-5-thia-1-azabicyclo (4,2,0)oct-2-en-3-yl)-2-propenyl)-imidazo (1,2-a ) pyridinium STEP A: 1-[3-[7β-[[[[[1-[4-fluoro-2,3-bis-[ (2-methoxy-ethoxy)-methoxy]-phenyl]-2-oxo-2-diphenyl-methoxy)-ethyl]-oxy]-imino][ 2-(triphenylmethyl)-amino]-thiazol-4-yl]-acetamido]-2-[( 4-methoxy-benzyloxy-carbonyl]-8-oxo-5-thia-1-azabicyclo-[4,2,0]-[ oct-2-en-3-yl]-2-propenyl-imidazo-(1,2-a) pyridinium iodide Using the procedure of Step H of Example 16, 955 mg of the product of Step G of Example 16 and 401 mg of imidazo [1,2-a] pyridine were reacted to obtain 486 mg of expected product after chromatography on silica, eluant: methylene chloride-methanol (95.5).

NMR Spectrum: $CDCl_3$ 399 MHz 3.20 (w) 326 (s) 3.34 (s) 3.35 (s): $CH_3O$; 3.40–3.95: $OCH_2—CH_2O$, $CH_2S$; 4.89 (d): $H_6$ cephalo; 5.74 (m): $H_7$ cephalo; 5.20–5.42 (9H, excess): $ArCO_2CH_2—OCH_2O$, $CH—CH_2N^+=$; 6.28 (m): $=CH—CH_2(E)$; 6.38 (s) 6.44 (s): Ar—CH(—O—)$CO_2^-$; 6.88 (s) 6.90 (s): $CO_2CH(C_6H_5)_2$; approx. 6.75 to 7.35: aromatic H's (phenyl groups)+ nitrogenous bicyclic H's; 7.85 (m, 1H) 8.03 (d, 1H) 8.36 (d, 1H) 9.09 (m, 1H); other nitrogenous bicycle H's; 7.94 (d), 8.25 (d): CONH.

STEP B: Internal salt of (6R(3(E), 6α, 7β(Z))) 1-(3-(7-(((2-amino-4-thiazolyl)-(carboxy-(2,3-dihydroxy- 4-fluorophenyl)-methoxy)-imino)-acetamido)-2-carboxy-8-oxo-5-thia-1-azabicyclo (4m2,0)oct-2-en-3-yl)-2-propenyl)imidazo (1,2-a) pyridinium Using the procedure of Step I of Example 16, 476 mg of the product of Step A were reacted to obtain 215 mg of desired product.

NMR Spectrum: (DMSO, 400 MHz 3.70 (m): $CH_2S$; 5.15 (d, resolved): $H_6$ cephalo; 5.74 (dd, d after exchange) 5.82 (dd, d after exchange): $H_7$ cephalo; 5.28 (m): $CH_2—N^+=$; 5.83 (s), 5.86 (s): Ar—CH (—O—) $CO_2^-$; 6.25 (m ): $CH=CH—CH_2$ (E); 6.89 (d, resolved, J=15.5): $CH=CH—CH_2(E)$; 6.60 (m), 6.78 (m): $H_6$, $H_5$ fluorophenyl; 6.76 (s) 6.80 (s): $H_5$ thiazole; 7.57 (m) 8.05 (m) 8.19 (m) and 8.28 (d, resolved. J=2.5) 8.44 (d, resolved, J=2.5) 8.96 (d, J=6.5): $H_5$1', $H_6$', $H_7$', $H_4$' and $H_2$', $H_3$', of the imidazo (1,2-a)pyridinium; 9.44 (d) 9,56 (d) CONH—C; 7.32 (m) 9.40 (m): mobile H's.

EXAMPLE 21

Internal salt of (6R-(3-(E]6α, 7β(Z))1-(3-( 7-(((2-amino-4thiazolyl-(carboxy-(2,3-dihydroxy-phenyl)-methoxy-imino)-acetamido)- 2-carboxy-8-oxo-5-thia-1-azabicyclo[4, 2,0 ]oct-2-en- 3-yl)-2-propenyl)-4-(methylthio) pyridinium STEP A: Ethyl [(2,3-dihydroxy) -phenyl]-hydroxy acetate 10 ml of a molar solution of titanium chloride in methylene chloride were added to a solution of 1.1 g of pyrocatechol in 20 ml of methylene chloride cooled to –20° C. and the mixture was stirred for 30 minutes at –20° C. Then, a solution of 1.02 g of ethyl glyoxylate in 10 ml of methylene chloride was added over 5 minutes and the mixture was stirred for 2 hours at –20° C. The mixture was allowed to return to ambient temperature and then was poured into 50 ml of a saturated solution of ammonium chloride, extracted with methylene chloride. The extracts were washed, dried and evaporated to dryness under reduced pressure. The residue was chromatographed on silica (eluant: methylene chloride-ethyl acetate (7-3)), to obtain 860 mg of the desired product melting at 86° C.

IR. Spectrum: $CHCl_3$
3595 $cm^{-1}$, 340 c, $^{-1}$ OH complex+associated, 1730 $cm^{-1}$ C=O, 1602-1402 $cm^{-1}$: aromatic.

NMR Spetrum: $CDCl_3$ 250 MHz ppm
5.33 (s): C—CH(OH)COOEt; 1.26 (t)-4.27 (m): COOEt; 3.75–5.86– 7.45: mobile H; 6.7 to 6.95: aromatic H's.

STEP B: Ethyl [2,3-bis-[(2-methoxy ethoxy)-methoxy]-phenyl]-hydroxy acetate 15.69 g of methoxy ethoxy methyl chloride and 16.35 g of N-ethyl diisopropylamine were added to a solution of 8.1 g of the product of Stp A in 750 ml of acetonitrile and the mixture was stirre for 16 hours at 0° C. Then, the mixture was poured into 100 ml of water and the acetonitrile was evaporated off, followed by taking up in methylene chloride, washing with 1N hydrochloric acid, with water, then with a 10% solution of sodium carbonate. After drying and evaporating to dryness under reduced pressure, the 12.3 g of product was chromatographed on silica (eluant: cyclohexane-ethyl acetate (5-5)) to obtain 6.7 g of the desired product.

IR Spectrum: $CHCl_3$
3315–3440 $cm^{-1}$: OH complex; 1735 $cm^{-1}$: C=O; 1601–1590 $cm^{-1}$: aromatics.

NMR Spectrum: $CDCl_3$ 250 MHz
1.21 and 4.22: $CO_2Et$; 3.37: $OCH_3$; 3.57–3.83–3.93: $CH_2$—$CH_2$—O; 5.25–5.28: O—$CH_2$—O; 4.07: OH; 5.39: C—CH(OH)—$CO_2Et$.

STEP C: Diphenylmethyl [2,3-bis-[(2-methoxy-ethoxy)-methoxy]-phenyl]-hydroxy acetate a) Saponification:

22 ml of 2N sodium hydroxide were added to a solution of 8.54 g of the product of Step B in 400 ml of ethanol and the mixture was stirred for 3 hours at ambient temperature, followed by acidifying to pH 2 with a N hydrochloric acid, concentrating to ½ volume under reduced pressure, diluting with 200 ml of water and extracting with methylene chloride and ethyl acetate. The extracts were dried and after evaporating to dryness under reduced pressure, 8.2 g of [2,3-bis-[(2-methoxy-ethoxy)-methoxy]-phenyl]-hydroxy acetic acid were obtained.

b) Esterification 109 ml of diphenyl diazomethane in a 0.3M solution in ethyl ether were added to a solution of 8.2 g of the above acid in 300 ml of methylene chloride cooled to 0° C. and the mixture was stirred for 16 hours at ambient temperature. Acetic acid was added at 0° C. followed by evaporation to dryness under reduced pressure to obtain 13 g of product which was chromatographed on silica, eluant: cyclohexane-ethyl acetate (6-4) to obtain 10.2 g of the desired product.

IR Spectrum: $CHCl_3$
3530–3520 $cm^{-1}$: OH complex; 1742 $cm^{-1}$: C=0; 1600-1585-1495 $cm^{-1}$: aromatics.

NMR Spectrum $CDCl_3$ 300 MHz
3.34–3.37: $CH_3$; 3.54–3.83: O—$CH_2$—$CH_2$; 4.08: 5.18–5.28: $OCH_2O$; 5.53: C—CH (OH)C—$(C_6H_5)_2$.

STEP D: Diphenylmethyl [2,3-bis-[( 2-methoxy-ethoxy)-methoxy]-phenyl]-phthalimidoxy acetate 226 mg of triphenyl phosphine and 77 mg of N-hydroxy phthalimide were added at ambient temperature to a solution of 227 mg of the product of Step C in 25 ml of tetrahydrofuran. The mixture is cooled to –5° C. and 136 ul (150 mg) of diethylazodicarboxylate were added over 2 hours. The mixture was stirred for 2 hours while allowing the temperature to rise to ambient and was then pourd into 25 ml of ice-cooled water, extracted with methylene chloride then with ethyl acetate. The extracts were dried and evaporated to dryness under reduced pressure to obtain 760 mg of residue which was chromatographed on silica (eluant: methylene chloride-acetone (97-3)) to obtain 230 mg of the desired product.

IR Spectrum:
$CHCl_3$ 1794–1738 $cm^{-1}$: C=O; 1602–1588-1488 $cm^{-1}$: aromatics.

NMR Spectrum: $CDCl_3$ 300 MHz
3.31 3.36: $CH_3$; 3.46–3.52–3.79–3.89: $CH_2$—$CH_2$-O; 5.24: O-$CH_2$-O; 6.43: C-CH(ON=)$CO_2$C-$(C_6H_5)_2$; 6.95: CH-$(C_6H_5)_2$; 7.72: Ar-H phthalimido; 7.0–7.35: Ar-H aromatic.

STEP E: Diphenylmethyl aminoxy [2,3-bis-[(2-methoxy-ethoxy)-methoxy] -phenyl]acetate 1.42 ml of (1.47 g) of hydrazine hydrate were added to a solution of 6.2 g of the product of Step D in 400 ml of ethanol and 20 ml of methylene chloride and the mixture was stirred for 3 hours at ambient temperature. After evaporating to dryness under reduced pressure, the dry extract was taken up in methylene chloride and the insoluble part was filtered out. The filtrate was evaporated to dryness under reduced pressure to obtain 5.0 g of desired product.

IR Spectrum $CHCl_3$:
3335 $cm^{-1}$: $ONH_2$; 1745 $cm^{-1}$: C=O; aromatics 1602, 1589, 1577, 1495 $cm^{-1}$ aromatics.

NMR Spectrum: $CDCl_3$ 250 MHz
3.35–3.37: $OCH_3$; 3.54–3.83–3.95: O-$CH_2CH_2$-O; 5.26–5.29: O-$CH_2$-O; 5.75: —C-CH($ONH_2$)$CO_2$C-$(C_6H_5)_2$; 5.86: O-$NH_2$; 6.95: COO-CH$(C_6H_5)_2$.

STEP F: [[[ 1-[2,3-bis-[(methoxy-ethoxy)-methoxy]-phenyl]-2-oxo -2-(diphenyl-methoxy)-ethyl]-oxy]-imino]-[2-triphenyl-methyl)-amino -thiazol-4-yl]acetic acid A mixture of 5.0 g of the product of Step E in solution in 60 ml of methanol with 4,016 g of [2-[(triphenyl-methyl)-amino]-thiazol-4-yl] acetic acid described in Belgian Patent Application No. 864,828) was stirred for 6 hours. After evaporating to dryness, the residue was chromatographed on silica, eluant: ethyl acetate—ethanol (7-3) to obtain 5.55 g of desired product.

IR Spectrum: CHCl$_3$
=C-NH: 3405 cm$^{-1}$; C=O: 1735 cm$^{-1}$; C=N, aromatic and CO$_2^-$: 1619–1602–1529–1494 cm$^{-1}$ NMR Spectrum: CDCl$_3$ 250 MHz
3.13–3.31: CH$_3$; 3.34–3.49–3.76: O-CH$_2$-CH$_2$-O; 5.14–5.18 O-CH$_2$-O; 6.11: —C-CH(ON=)CO$_2$C—; 6.46: —CO$_2$-CH(C$_6$H$_5$)$_2$; 6.81: CH thiazol; 6.75 to 7.3 aromatic H's.

STEP G: 4-methoxy-benzyl 7δ-[[[[[1-[2,3-bis-[(2-methoxy-ethoxy)-methoxy] -phenyl]-2-oxo-2-(diphenyl-methoxy)-ethyl]-oxy]-imino]-[2 -([triphenyl-methyl)-amino]-thiazol-4-yl]-acetamido]- 3-[(Z)-3-chloro-1-propenyl] -8-oxo-5-thia-1-azabicyclo-[4,2,0-oct-2-en-2-carboxylate 3.55 g of 4-methoxy benzyl 7δ-amino-3-[(Z)-3-chloro-1-propenyl]-8-oxo-5-thia-1 -azabicyclo[4,2,0]oct-2-en-2-carboxylate hydrochloride (described in EP Application No. 0,333,154) and 1.6 g of N-ethyl dimethylaminopropyl carbodiimide (EDAC) were added to a solution of 6.18 g of the product of Step F in 150 ml of methylene chloride and cooled to 0° C. The mixture was stirred for 10 minutes at 0° C., then for 2 hours while allowing the temperature to rise 20° C. The mixture was poured into a molar solution of potassium hydrogen phosphate and extraction took place with methylene chloride, then with ethyl acetate followed by drying and evaporating to dryness. After chromatography on silica and eluting with methylene chloride—ethyl acetate (9-1), 5.1 g of the desired product were obtained.

IR Spectrum: CDCl$_3$
3040 cm$^{-1}$: =C-NH; 1790–1731–1684 cm$^{-1}$: C=O; aromatics heteroatom, amide II: 1613, 1597–1526–1517–1496 cm$^{-1}$.

NMR Spectrum: CDCl$_3$ (300 MHz)
3.24 to 3.37: CH$_2$-O-CH$_3$ and C-s-CH$_2$—; 3.44 to 4.0:CH$_2$Cl and C$_6$H$_5$OCH$_3$; 3.44 to 4.0: O-CH$_2$-CH$_2$—; 5.15 to 5.28: —O-CH$_2$-O; 5.67 to 5.88, 6.29: C-CH-CH$_2$Cl; 6.77: CH thiazol; 6.7 to 7.4: aromatics; 8.01–8.37: NH.

STEP H: 4-methoxy-benzyl 7δ-[[[[[ 1-[ 2, 3-bis-[ (2-methoxy-ethoxy)-methoxy ]-phenyl]-2-oxo-2-(diphenyl-methoxy)-ethyl]-oxy]-imino]-[2 -(triphenyl-methyl)-amino]-thiazol-4-yl]-acetamido] -3-[ (Z)-3-iodo-1-propenyl] -8-oxo-5-thia-1-azabicyclo-[4,2,0]-oct-2-en-2 carboxylate 0.57 g of sodium iodide and 1 crystal of iodine were added to a solution of 1.25 g of the product of Step G in 5 ml of acetone and the mixture was stirred for 90 minutes at ambient temperature. After evaporating to dryness under reduced pressure, the dry extract was taken up in methylene chloride, washed with a 10% solution of sodium thiosulfate, then with salt water, followed by drying and evaporating to dryness under reduced pressure to obtain 1.28 g of the expected product which is used as is for the following step.

STEP I: 1-[3[7δ-[[[[[1-[2,3-bis-[(2-methoxy-ethoxy)-methoxy]-phenyl] -2-oxo-2-(diphenyl-methoxy)-ethyl]-oxy-imino] -[ 2-(triphenylmethyl) -amino] -thiazol-4-yl]-acetamido]-2- [(4-methoxy-benzyloxy) -carbonyl]-8-oxo-5-thia-1-azabicyclo- [4,2,0]-[ oct-2-en-3-yl]-2-propenyl]-4-methyl-thio pyridinium iodide 1.28 g of the product of Step H, 1.15 g of thiomethyl pyridine and 3 ml of methylene chloride were mixed together and after evaporating to dryness under reduced pressure, the residue was chromatographed on silica (eluant: methylene chloride—methanol (97-3), then (96-4) and (95-5)) to obtain 415 mg of the desired product.

NMR Spectrum: CDCl$_3$ 250 MHz
2.6: S-CH$_3$; 3.21, 3.25, 3.35, 3.36, 3.37: —OCH$_3$; 3.4 to 3.9: —O-CH$_2$-CH$_2$-O; 3.77, 3.79 C$_6$H$_5$-OCH$_3$

STEP J: Internal salt of (6R-(E) 6$^\alpha$, 7$^\delta$-(Z))) 1-3-(7-(((2-amino -4-thiazoyl)-(carboxy-(2,3-dihydroxy-phenyl)- methoxy)-imino)-acetamido) -2-carboxy-8-oxo-5-thia-1-azabicyclo-[ 4,2,0]-oct- 2-en-3-yl) -2-propenyl)-4-(methylthio) pyridinium 400 mg of the product of Step I, 4.5 ml of trifluoroacetic acid and 0.5 ml of anisole were stirred for 2 hours at ambient temperature and then, 0.5 ml of water were added. The mixture was stirred for 2 hours at ambient temperature, followed by filtering, rinsing twice with 3 ml of trifluoroacetic acid and 15 ml of ethyl ether were added. The mixture was stirred for 15 minutes, followed by separating and drying under reduced pressure to obtain 222 mg of the desired product.

MR Spectrum: DMSO (300 MHz) ppm
2.71: SCH$_3$; 3.72: C-S-CH$_2$-C; 5.19, 5.76, 5.83; —S-CH-(-N=)-CH-NH—; 5 22: —C=C-CH$_2$-N$^+$; 5.91, 5.95: H imino-carboxybenzyl; 6.28: —CH=CH-CH$_2$-N$^+$; 6.98: —CH=CH-CH$_2$-N$^+$; 6.59, 6.79: aromatic H's; 6.79 6.83: H thiazol; 9.49: NH.

EXAMPLE 22

Internal salt of (6R-(3-(E) 6$^\alpha$, 7$^\delta$-(Z))) 7-(3-(7-(((2-amino-4-thiazoyl) -(carboxy-(2,3-dihydroxyphenyl)-methoxy)-imino)- acetamido) -2-carboxy-8-oxo-5-thia-1-azabicyclo-[4,2,0] -oct-2-en-3-yl) -2-propenyl)-thieno-[2,3-b]-pyridinium

STEP A: 1-[3-[7$^\delta$-[[[[[-[2,3-bis-[(1-methoxy)-ethoxy)-methoxy] -phenyl] -2-oxo -2-(diphenyl-methoxy)-ethyl]-oxy]-imino]- [2-[(triphenylmethyl)-amino]-thiazol [4-yl ]-acetamido]-2-[ (4-methoxy-benzyloxy) -carbonyl]-8-oxo-5-thia-1-azabicyclo [4,2,0]-[oct-2-en-3-yl] pyridinium iodide Using the procedure of Step I of Example 21, 1.24 g of the product of Step H of Example 21 and 1.28 of thieno (2,3-b) pyridine were reacted to obtain after chromatography on silica, eluant: methylene chloride—methanol (97-3 then 96-4 and 95-5), 450 mg of the desired product.

IR Spectrum: CHCl$_3$

=C-NH: 3404 cm$^{-1}$; C=O: 1790, 1731, 1684 cm$^{-1}$; C=C. aromatics, heteroatoms, amide II: 1613, 1587, 1526, 1517, 1496 cm$^{-1}$; thieno pyridine: 1599 cm$^{-1}$.

NMR Spectrum: CDCl$_3$ 300 MHz 3.21, 3.26, 3.34, 3.37: CH$_2$-O-CH$_3$; 3.43, 3.55, 3.82: —O-CH$_2$-O-CH$_2$CH$_2$-CH$_2$-; 3.80: C$_6$H$_5$O-CH$_3$; 5.2 to 5.3: O-CH$_2$-O-CH$_2$—, CO$_2$CH$_2$C$_6$H$_5$-O—; 5.90: —CH-CH$_2$-N$^+$; 6.45 to 6.6: C-CH=CH-CH$_2$-N$^+$; 6.51 to 6.56: CO$_2$-CH(C$_6$H$_5$)$_2$; 6.73: H thiazol; 6.85 to 8.78: aromatic H's.

STEP B: Internal salt of (6R-(3-(E) 6$^\alpha$, 7$^\delta$-((Z)))-7-(3-(7-(((2-amino-4-thiazolyl)-(carboxy-(2,3-dihydroxy-phenyl)-methoxy)-imino)-acetamido)-2-carboxy-8-oxo-5-thia-1-azabicyclo[4,2,0]oct-2-en-3-yl) -2-propenyl)-thieno(2,3-b) pyridinium Using the procedure of Step J of Example 21, 430 mg of the product of Step A were reacted to obtain 206 mg of desired product.

IR Spectruma: Nujol

C=O: 1775 cm$^{-1}$ (δ-lactam) 1670 cm$^{-1}$ (complex); conjugated system, aromatic, NH$_2$, amide: 1599, 1580, 1520 cm$^{-1}$.

NMR Spectrum: CDCl$_3$ 400 MHz 3.69: —S-CH$_2$-C—; 5.18, 5.78, 5.86: —NH-CH-CH-S—; 5.67: =CH-CH$_2$-N$^+$; 5.91, 5.95: —C-CH(O-N=)CO$_2$H; 6.31 and 7.15: the H's of the propylene; 6.59 and 6.79: aromatic H's; 6.78 and 6.82: H thiazol; 7.89 to 9.22: thieno pyridine; 9.49 and 9.61: amide.

EXAMPLE 23

Internal salt of (6R-(3-(E) 6$^\alpha$, 7$^\delta$-(Z)))-7-(3-(7-(((2-amino-4-thiazolyl)-(carboxy-(2,3-dihydroxy-phenyl)-methoxy)-imino)-acetamido)-2-carboxy-8-oxo-5-thia-1-azabicyclo[4,2,0]oct-2-en-3-yl)-2-propenyl)-imidazo (1,2-a) pyridinium STEP A:
1-[3-[7δ-[[[[[1-[2,3-bis-[(2-methoxy-ethoxy)-methoxy] -phenyl ]-2-oxo-2-(diphenyl-methoxy)-ethyl]-oxy]-imino]-[2-[(triphenylmethyl)-amino]-thiazol-4-yl]-acetamido]-2-[(4-methoxy-benzyloxy)-carbonyl]-8-oxo-5-thia-1-azabicyclo[4,2,0] [oct-2-en-3-yl] -2-propenyl]-imidazo(1,2-a) pyridinium iodide Using the procedure of Step I of Example 21, 1.24 g of the product of Step H of Example 21 and 1.28 g of imidazopyridine were reacted to obtain 270 mg of expected product.

NMR Spectrum CDCl$_3$ 400 MHz 3.25, 3.20, 3,35, 3.37: CH$_2$OCH$_3$; 3.30 to 3.90: OCH$_2$-CH$_2$-OCH$_3$; 3.30 to 390: —S-CH$_2$-C—; 3.78, 3.79: —C$_6$H$_5$OCH$_3$; 4.88 and 5.72: NH-CH-CH-S; 5.10 to 5.50: C-O-CH$_2$-OCH$_2$—, =C-CH$_2$-N$^+$; 6.28: C-CH=CH$_2$—; 6.51 to 6.56: —C-CH(O-N=)CO$_2$CH; 6.7 to 7.4: aromatic H, H thiazol, H propylene; 7.93, 8.20: NH.

STEP B: Internal salt of (6R-(3-(E) 6$^\alpha$, 7$^\delta$-(Z))) 7-(3-(7-(((2-amino-4-thiazolyl)-(carboxy-(2,3-dihydroxy-phenyl)-methoxy-imino)-acetamido)-2-carboxy-8-oxo-5-thia-1-azabicyclo[4,2,0]oct-2-en-3-yl]-2-propenyl)-imidazo (1,2-a)pyridinium Using the procedure of Step J of Example 21, 280 mg of the product of Step A were reacted to obtain 140 mg of desired product.

IR Spectrum:

C=O: 1775, 1670 cm$^{-1}$; conjugated system, aromatic, amide II: 1598, 1530, 1510 cm$^{-1}$.

NMR Spectrum: DMSO 300 MHz 3.45 to 4.20: —S-CH$_2$—; 5.16, 5.76, 5.82: —NH-CH-CH-S-; 5.29: —CH$_2$-N$^+$—; 5.91, 5.94: C-CH(—O-N=)CO$_2$H; 6.26: 1H propylene; 6.58, 6.70 to 6.95: H thiazol, aromatic, 1H propylene; 9.47, 9.58: NH; 7.58, 8.06, 8.20, 8.96, 8.29, 8.44: bicycle.

EXAMPLE 24

Internal salt of (6R-(3-(E) 6$^\alpha$, 7$^\delta$-(Z)))-7-(3-(7-(((3-amino-4-thiazolyl)-(carboxy-(2,3-dihydroxy-phenyl)-methoxy)-imino)-acetamido)-2-carboxy-8-oxo-5-thia-1-azabicyclo[4,2,0]oct-2-en-3-yl)-2-propenyl)-quinolinium STEP A: 1-[3-[7δ-[[[[[1-[2,3-bis-[(2-methoxy-ethoxy)- methoxy]-phenyl ]-2-oxo-2-(diphenyl-methoxy)-ethyl]-oxy]-imino]-[2-[(triphenylmethyl)-amino]-thiazol-4-yl]-acetamido]-2-[(4-methoxy-benzyloxy)-carbonyl]-8-oxo-5-thia-1-azabicyclo[4,2,0] [oct.-2-en-3-yl]-2-propenyl]-quinolinium iodide Using the procedure of Step I of Example 21, 1.33 g of the product of Step H of Example 21 and 1.2 g of quinoline were reacted to obtain 475 mg of the desired product after chromatography on silica (eluant: methylene chloride—methanol (97-3 then 95-5)).

NMR Spectrum 3.42 to 3.95: OCH$_2$-CH$_2$-OCH$_3$; 3.78, 3.79: —C$_6$H$_4$-OCH$_3$; 5.13 to 5.28: —OCH$_2$-O-CH$_2$—, =C-CH-(O-N= ); 5.96, 6.11: —CH$_2$-N$^+$; 6.49, 6.55: —CO$_2$-CH-(C$_6$H$_5$)$_2$; 6.85, 8.93: aromatics.

STEP B: Internal salt of (6R-(3-(E) 6α, 7δ-(Z))) 7-(3-(7-(((2-amino-4 -thiazolyl) (carboxy-(2,3-dihydroxy-phenyl)-methoxy)-imino)-acetamido)-2-carboxy-8-oxo-5-thia-1-azabicyclo[4,2,0] oct-2-en-3-yl) -2-propenyl) quinolinium Using the procedure of Step J of Example 21, 465 mg of the product of Step A were reacted to obtain 255 mg of the desired product.

NMR Spectrum: DMSO 300 MHz 3.3 to 3.8: —S-CH$_2$—; 5.15 and 5.78: —NH-CH-CH-S—; 5.91: —C-CH(O-N=)CO$_2$H and CH$_2$-N$^+$—; 6.39: =C-CH=CH—; 6.99: =C-CH-CH— 6.7 to 6.9: aromatic H's; 8.08 to 9.58: bicyclic H.

EXAMPLE 25

Internal salt of (6R-(3-(E) 6α, 7δ-(Z)))
1-(3-(7-(((2-amino-4-thiazolyl)
(carboxy-(2,5-dichloro-3,4-dihydroxy-phenyl)
-methoxy)-imino)-acetamido)
-2-carboxy-8-oxo-5-thia-1-azabicyclo[4,2,0]
oct-2-en-3-yl)-2-propenyl)-N,N-dimethyl
benzenaminium STEP A: [[[1-[2,5-dichloro-3,4-bis-[(2-methoxy
ethoxy)-methoxy]-phenyl ]-2-oxo-2-(diphenyl
methoxy)-ethyl]-oxy]-imino]-[2-[(triphenylmethyl)
-amino]-thiazol-4-yl]acetic acid Using the procedure of Step E of Example 1, 3.5 g diphenyl methyl aminoxy [2,5-dichloro-3,4-bis-[(2-methoxy-ethoxy)-methoxy]-phenyl] -acetate in Step E of Example 9) and 2.37 g oxo [2-[(triphenyl-methyl)-amino] -thiazol-4-yl]-acetic acid in Belgian Patent Application No. 864,828 were reacted to obtain after chromatography on silica (eluant: ethyl acetate—ethanol (9-1)) 5.14 g of the desired product.

NMR Spectrum: 300 MHz CDCl$_3$ 3.30 (s): OCH$_3$; 3.51, 3.92 (m): —O-CH$_2$-OCH$_3$; 5.16 (s) 5.18 (s): O-CH$_2$-O; 6.25: CH-CO-CHø$_2$, H$_6$; 7.20 to 7.30: aromatic H's.

STEP B: 4 -methoxy-benzyl 7δ
-[[[[1-[2,5-dichloro-3,4-bis-[(2-methoxy-ethoxy)
-methoxy]-phenyl]-2-oxo-2-(diphenyl-methoxy)-ethyl
oxy]-imino]-[2-[(triphenylmethyl)-amino]-thiazol-4-
yl]-acetamido]
-3-[(Z)-3-chloro-1-propenyl]-8-oxo-5-thia-1-
azabicyclo[4,2,0]oct -2-en-2-carboxylate Using the procedure of Step F of Example 1, 4.8 g of the product of Step A and 2.26 g of 4-methoxy-benzyl 7δ-amino-3-[(Z)-3-chloro-1 -propenyl]-8-oxo-5-thia-1-azabicyclo[4,2,0[oct-2-en-2-carboxylate hydrochloride (EP Patent No. 0,333,154) were reacted to obtain after chromatography on silica (eluant: methylene chloride—ethyl ether (9-1)), 4.6 g of desired product.

NMR Spectrum: 300 MHz CDCl$_3$ 3.05 (m) 3.45 (m): —CH$_2$-Cl; 3.36, 3.37 (s): —O-CH$_3$; 3.57 (m) 3.97 (m) : O-CH$_2$-O—; 3.81 (s,d): —o-OCH$_3$; 4.99, 5.02 (d) : NH-CH-CH-S; 5.86, 5.90: NH-CHCH-S; 5.15 to 5.26: O-CH$_2$-O—; 5.75 (m): H$_2$ propylene; 6.26 (J=11.5) (d) 6.35 (J=11.5) (d) : H$_1$ propylene; 6.47 to 6.50 (s) —CO$_2$-CH-o$_2$; 6.85 to 7.40 the aromatic H's.

STEP C: 4 -methoxy-benzyl 7δ
-[[[[1-[2,5-dichloro-3,4-bis-[(2-methoxy-ethoxy)
-methoxy]-phenyl]-2-oxo-2-(diphenyl-methoxy)-ethyl]
-oxy]-imino]-[2-[(triphenylmethyl)-amino]-thiazol-4-
yl]-acetamido]
-3-[(Z)-3-chloro-1-propenyl]-8-oxo-5-thia-1-
azabicyclo[4,2,0]oct -2-en-2-carboxylate Using the procedure of Step G of Example 1, 150 mg of the product of Step B were reacted to obtain 160 mg of the desired product.

STEP D: 1-[3-[7δ-[[[[[1-[2,5-dichloro-3,4-bis-
[(2 -methoxy-ethoxy)-methoxy]-phenyl ]
-2-oxo-2-(diphenyl-methoxy)-ethyl]-oxy]-imino]-
[2-(triphenylmethyl)
-amino]-thiazol-4-yl]-acetamido]-2-[(4-methoxy-
benzyloxy)-carbonyl]
-8-oxo-5-thia-1-azabicyclo[4,2,0]oct-2-en-3-yl]
-2-propenyl]-N,N-dimethyl benzene aminium iodide Using the procedure of Step H of Example 1, 155 mg of the product of Step C and 64 mg of N,N-dimethylaniline were reacted to obtain after chromatography on silica (eluant: methylene chloride—methanol (96-4)), 55 mg of the desired product.

NMR Spectrum: CDCl$_3$ 300 MHz
2.95 (s):

3.30 to 3.45: —S-CH$_2$—; 3.35, 3.36, 3.37 (s): O-CH$_3$; 3.82 (s,d) ø-OCH$_3$; 3.90 to 4.05: —O-CH$_2$CH$_2$-O—, =C-CH$_2$-N (CH$_3$)$_2$o; 4.94 (d)–4.98 (d): NH-CH-CH-S; 5.87 (m): NH-CH-CH-S; 5.18 to 5.30 (m): O-CH$_2$-O and O-CH$_2$-o; 6.14 (m) (E) C-CH=CH-CH$_2$—; 6.70 to 7.40 (m) C-CH-CH-CH$_2$—, H thiazole, aromatic H's; 8.17, 8.25 (d): NH.

STEP E: Internal salt of (6R-(3-(E) 6$^α$, 7$^δ$-(Z)))
1-(3-(7-(((2-amino-4
-thiazolyl)-(carboxy-(2,5-dichloro-3,4-dihydroxy
-phenyl)-methoxy)-imino)-acetamido)
-2-carboxy-8-oxo-5-thia-1-azabicyclo[4,2,0]oct-2-en-3-
yl)-2-propenyl)-N,N-dimethyl benzene aminium Using the procedure of Step I of Example 1, 50 mg of the product of Step D were reacted to obtain 22 mg of the desired product.

EXAMPLE 26

Internal salt of (6R-(3-(E) 6α,
7δ-(Z)))-1-(3-(7-(((2-amino-4-thiazolyl)
-(carboxy-(2,5-dichloro-3,4-dihydroxy-phenyl)-
methoxy)-imino)-acetamido)
-2-carboxy-8-oxo-5-thia-1-azabicyclo[4,2,0]
oct-2-en-3-yl)-2-propenyl)-imidazo(1,2-a)
pyridinium STEP A: 1-[3-[7δ
-[[[[[1-[2,5-dichloro-3,4-bis-[(2-methoxy-ethoxy)
-methoxy]-phenyl]-2-oxo -2-(diphenyl
-methoxy)-ethyl], oxy]-imino ]
-[2-(triphenylmethyl)-amino]-thiazol-4-yl]-
acetamido]-2-[ (4-methoxy-benzyloxy)-carbonyl]
-8-oxo-5-thia-1-azabicyclo [4,2,0]
oct-2-en-3-yl]-2-propenyl]-imidazo (1,2-a)
pyridinium iodide Using the procedure of Step H of Example 1, 1.24 g of the product of Step C of Example 25 and 0,497 g of imidazo(1, 2-a) pyridine were reacted to obtain after chromatography on silica (eluant: methylene chloride—methanol (95-5)), 625 mg of the desired product.

NMR Spectrum: CDCl$_3$ 400 MHz 3.34, 3.36: —$CH_2$-O-$CH_3$; 3.50, 3.87: O-$CH_2$-$CH_2$-OMe; 3.8 0 (s) —o-$OCH_3$; 4.94 (d,d): —NH-CH-CH-S—; 5.20, 5.24: —O-$CH_2$-O—, $CO_2$-$CH_2$-ø ; 5.86: NH-CH-CH-S; 6.15, 6.35: H propylene; 6.47, 6.51: =N-O-CH—; 6.77: H thiazole; 6.90 to 7.40: the aromatic H's; 7.88, 8.04: H of the imidazole; 7.88: —NHCø$_3$.

STEP B: Internal salt of (6R-(3-(E) 6α, 7δ-(Z)))
1-(3-(7-(((2-amino-4
-thiazolyl)-(carboxy-(2,5-dichloro-3,4-dihydroxy-
phenyl)-methoxy)-imino)-acetamido)
-2-carboxy-8-oxo-5-thia-1-azabicyclo[4,2,0]
oct-2-en-3-yl)-2-propenyl)-imidazo (1,2-a)
pyridinium Using the procedure of Step I of Example 1, the product of Step A were reacted to obtain 327 mg of desired product.

NMR Spectrum: $CDCl_3$ 3300 MHZ 3.50 to 3.75: —S-$CH_2$-C=; 5.16: —NH-CH-CH-S—; 5.79 (m): —NH-CH-CH-S—; 6.24 (m): ≡C-CH=CH-C—; 6.91 (dd): =C-CH=CH-C—; 6.83 (dd): H thiazole; 7.58, 8.06 (t) and 8.21, 8.96 (d): H pyridine; 8.29, 8.45: H imidazole; 9.62: NH; 993: $NH_2$, $CO_2H$.

EXAMPLE 27

STEP E: Internal salt of (6R-(3-(E) 6α, 7δ-(Z)))
1-(3-(7-(((2-amino-4
-thiazolyl)-(carboxy-(2,5-dichloro-3,4-dihydroxy-
phenyl)-methoxy)-imino)-acetamido)
-2-carboxy-8-oxo-5-thia-1-azabicyclo[4,2,0]
oct-2-en-3-yl)-2-propenyl)-6,7-dihydro
-5H-pyrindinium STEP A: 1-[3-[7δ-[[[[[1-[2,5-dichloro-3,4-bis
-[(2-methoxy-ethoxy)-methoxy]-phenyl
]-2-oxo-2-(diphenyl-methoxy)-ethyl]-oxy]-imino]-
[2-[(triphenylmethyl)
-amino]-thiazol-4-yl]-acetamido]-2-
[(4-methoxy-benzyloxy)-carbonyl]
-8-oxo-5-thia-1-azabicyclo[4,2,0]oct-2-en-3-yl]
-2-propenyl]-6,7-dihydro-5H-pyrindinium iodide Using the procedure of Step H of Example 1) 1.13 g of the product of Step C of Example 25 and 457 mg of cyclopentano [2,3-a] pyridine were reacted to obtain after chromatography on silica (eluant: methylene chloride—methanol (9-1)) 460 mg of the desired product.

NMR Spectrum: $CDCl_3$ 300 MHz ppm 2.41, 3.23, 3.45: —S-$CH_2$ and $CH_2$ of the cyclopentane; 3.34 to 3.37: O-$CH_3$; 3.57 to 3.98: —O-$CH_2$-$CH_2$-O—; 3.81: O-O-$ch_3$; 4.97, 5.88: NH-CH-CH-S—; 5.12 to 5.25: —O-$CH_2$-O—; 6.22 and 6.45 (ΔE) =C-CH-CH-$CH_2$—; 6.85 t 7.35: ≡C-CH=CH-$CH_2$—; 6.46, 6.50 (s) =N-O-CH-$CO_2$—; 6.72: H thiazole; 6.85 to 7.35: aromatic H's 7.97, 8.23 (d): NH; 7.79, 9.20: H pyridine.

STEP B: Internal salt of (6R-(3-(E) 6α, 7δ-(Z)))-1-(3-(7-(((2-amino-4
-thiazolyl)-(carboxy-(2,5-dichloro-3,4-dihydroxy-
phenyl)-methoxy)-imino)-acetamido)
-2-carboxy-8-oxo-5-thia-1-azabicyclo
[4,2,0]oct-2-en-3-yl)-2-propenyl)-6,7-dihydro-5H-
pyrindinium Using the procedure of Step I of Example 1,447 mg of the product of Step A were reacted to obtain 194 mg of the desired product.

NMR Spectrum: DMSO 300 MHz 2.23 (m): the central $CH_2$'s; 3.19 (t) the =C-$CH_2$'s; 5.17 (d): $H_6$; 5.33 (m): =CH-$CH_2$-$N^+$; 5.78 (m) (2H): the $H_7$'s and O-CH-ø's; 6.23 (m): $CH_2$-CH= E; 6.82 (s) (d): $H_5$, thiazole's; 6.89 (d) d) the =C-CH=CH (ΔE)'s; 7.01 (s, d) aromatic H; 7.91 (t): $H_5$'; 8.42 (d): $H_4$'; 8.76 (d): $H_6$'; 7.35 (1): $NH_2$; 9.56 to 10.0 the mobile H's.

EXAMPLE 28

Internal salt of (6R-(3-(E) 6α, 7δ-(Z)))
1-(3-(-(((2-amino-4-thiazolyl)
-carboxy-(2,5-dichloro-3,4-dihydroxy-phenyl)-
methoxy)
-imino)-acetamido)-2-carboxy-8-oxo-5-thia-1-
azabicyclo[4,2,0 ]oct-2-en-3 -yl)
-2-propenyl)-1-methyl-pyrrolidinium STEP A:
1-[3-[7δ-[[[[[1-[2,5-dichloro-3,4-bis-[(2-methoxy-
ethoxy)-methoxy]
-phenyl]-2-oxo-2-(diphenyl-methoxy)-ethyl]
-oxy]-imino]
-[2-triphenylmethyl)-amino]-thiazol-4-yl]acetamido]-2-
[(4-methoxy-benzyloxy)-carbonyl]
-8-oxo-5-thia-1-azabicyclo[4,2,0]oct-2-en-3
-yl]-2-propenyl]-1-methyl pyrrolidinium iodide Using the procedure of Step H of Example 1, 605 mg of the product of Step C of Example 25 and 174 mg of N-methyl pyrrolidine were reacted to obtain after chromatography on silica (eluant: methylene chloride—methanol (9-1)), 210 mg of the desired product.

NMR Spectrum: 400 MHz in $CDCl_3$ 3.49 to 3.72 and 3.97: the central $CH_2$'s and $N^+CH_3$; 3.20, 3.33 3.34: the $OCH_3$'s 2.6: pyrrolidine; 4.01, 4.28, 4.52; $N^+$-$CH_2$; 5.25: $CO_2$-$CH_2$-ø and O-$CH_2$-O; 6.09 and 6.17 =C-CH=CH-$CH_2$—; 6.85 to 7.42; =C-CH=$CH_2$— and $CO_2$-$CH_2$.

STEP B: Internal salt of (6R (3-(E) 6α,
7δ-(Z)))-1-(3-(7-(((2-amino-4
-thiazolyl)-(carboxy-(2,5-dichloro-3,4-dihydroxy-
phenyl)-methoxy)
-imino)-acetamido)-2-carboxy-8-oxo-5-thia-1-
azabicyclo
[4,2,0]oct-2-en-3-yl)-2-propenyl)-1-methyl
pyrrolidinium Using the procedure of Step I of Example 1, 200 mg of the product of Step A were reacted to obtain 93 mg of the desired product.

NMR Spectrum: DMSO 300 MHz ppm 2.09 (sl): $CH_2$ in position 3', 4'; apporox. =3.45 (sl) $CH_2$ in position 2', 5'; 2.99 (s): $N^+CH_3$; 3.61 (d,d) and 3.80 (d) 3.86 (d): $CH_2$-S; 4.10 (d): =CH-$CH_2$-$N^+$; 5.21 (d): $H_6$; 5.84 (m): $H_7$; 5.78 (s) 5.81 (s) =C-CH-O; 6.16 (m) : CH=CH-$CH_2$ (ΔE); 7.03 (d, J=15) CH=CH-$CH_2$; 7.01 (s) 7.06 (s) 6.83 (s) 6.84 (s) : $H_5$ of the thiazole and aromatic 1H; 9.60 (d) 9.66 (d) CONH-CH; 9.95 (m) 7.40 (m): mobile H's.

EXAMPLE 29

Internal salt of (6R-(3-(E) 6α, 7δ-(Z)))
1-(3-(7-(((2-amino-4-thiazolyl)
-(carboxy-(2,5,-dichloro-3,4-dihydroxy-phenyl)-
methoxy)-imino)
-acetamido)-2-carboxy-8-oxo-5-thia-1-azabicyclo
[4,2,0]oct-2-en-3 -yl)-2-propenyl)-thieno (2,3-c)
pyridinium

STEP A:

1-[3-[7$^δ$-[[[[1-[2,5-dichloro-3,4-bis-[(2-methoxy-
ethoxy)-methoxy
]-phenyl]-2-oxo-2-(diphenyl-methoxy)-ethyl]-oxy]
-imino]-[2-(triphenylmethyl)
-amino]-thiazol-4-yl]-acetamido]-2-
[(4-methoxy-benzyloxy)
-carbonyl]-8-oxo-5-thia-1-azabicylo
[4,2,0]oct-2-en-3-yl ]-2-propenyl]-thieno-(2,3-c)
pyridinium iodide Using the procedure of Step H of Example 1, 1 g of the product of Step C of Example 25 and 458 mg of thieno-[2, 3-c]-pyridine were reacted to obtain after chromatography on silica (eluant: methylene chloride—methanol (9-1)) 520 mg of the desired product.

NMR Spectrum: CDCl$_3$ 300 MHz 3.56 (s) 3.98 (s): the central CH$_2$'s and S-CH$_2$; 3.79 (s): ø-OCH$_3$; 5.20 to 5.30: O-CH$_2$-O and CO$_2$-CH$_2$-ø; 4.95, 5.26 (m) : NH-CH-CH-S; 6.33, 6.48 (m) E: C-CH=CH—; 6.80 to 7.40: =C-CH=CH; 5.59 (m) to 5.80 (m): =CH-CH$_2$-N=; 6.80 to 7.40: aromatic H; 6.77 (sd): H thiazole; 11.50 (sl,d) NH, —N=CH—.

STEP B: Internal salt of (6R-(3-(E) 6$^α$, 7$^δ$-(Z)))-1-(3-(7-(((2-amino-4 -thiazoyl)-(carboxy-(2,5-dichloro-3,4-dihydroxy-phenyl)-methoxy) -imino)-acetamido)-2-carboxy-8-oxo -5-thia-1-azabicyclo [4,2,0]oct-2-en-3-yl)-2-propenyl)-thieno-(2,3-c) pyridinium Using the procedure of Step I of Example 1, the product of Step A was reacted to obtain 114 mg of the desired product.

NMR Spectrum: DMSO 300 MHz 5.19 (d): H$_6$; 5.46 (d) N$^+$CH$_2$-CH=; 5.79 (m): —O-CH-o, H$_7$; 6.35 (m): =CH-CH$_2$(E); 6.81 (s) d: H$_5$ thiazole; 7.00 (s): H of the phenyl; 7.07 (dJ=16): =C-CH=CH (E) ; 7.34 (1): NH$_2$; 7.94 (dJ=5,5) H$_3$' 8.76 (dJ=5.5): H$_2$'; 8.53 (d, J=6.5) 8.73 (d, J=6.5): H$_4$' and H$_5$'; 9.91 (s,l): H$_6$'; 9.59 (d,d) =C-NH-CH; 9.88: mobile H.

EXAMPLE 30

Internal salt of (6R-(3-(E)
6α,7δ-(Z)))-7-(3-(7-(((2-amino-4-thiazolyl)
(carboxy-(4-cyano-2,3-dihydroxy-phenyl)-methoxy)
-imino)-acetamido)
-2-carboxy-8-oxo-5-thia-1-azabicyclo[4,2,0]
oct-2-en-3-yl)
-2-propenyl]-thieno-(2,3-b)-pyridinium

STEP A:
[4-cyano-2,3-bis-[(2-methoxy-ethoxy)-methoxy]
-phenyl] bromoacetic acid 440 microliters of bromoform were added at −5° C. to a mixture of 4.26 mg of lithium bromide, 598 mg of potassium hydroxide and 5 ml of water and then, a solution of 825 mg of a 4-cyano-2,3-bis-[ (2-methoxy-ethoxy)-methoxy]-ben-zaldehyde (preparation given hereafter) in 5 ml of dioxane was added dropwise. The mixture was stirred for 72 hours at 0° C. to −5° C. and was poured into a stirred mixture at 0° C. to −5° C. of 15 ml of ethyl acetate and 11 ml of hydrochloric acid. Extraction was carried out with ethyl acetate and the extracts were washed, dried and evaporated to dryness under reduced pressure. The oil obtained was used as is for the following step.

STEP B: Diphenymethyl [4,cyano-2,3-bis-[(2-methoxy-ethoxy)methoxy] -phenyl]-bromoacetate The product of Step A was dissolved in 10 ml of methylene chloride and 470 mg of diphenyl diazomethane were added. Evaporation was carried out followed by chromatography on silica (eluant: cyclohexane—ethyl acetate (2-1)) to obtain 450 mg of the desired product.

NMR Spectrum 3.31 (s), 3.37 (s): (OCH$_3$'s: 3.43 (m), 3.61 (m), 3.77 (m), 4.05 (m) central CH$_2$'s: 5.18 (d), 5.25 (d), 5.29 (AB), OCH$_2$O's; 6.02 (s): =CH-X.

STEP C: Diphenymethyl 4-cyano-[2,3-bis]-[(2-methoxy-ethoxy) -methoxy]-phenyl]-phthalimidoxy-acetate 326 mg of N-hydroxyphthalimide and 196 mg of potassium acetate were added to a solution of 820 mg of the product of Step B in 13 ml of dimethylformamide and the mixture was stirred for 3 hours at ambient temperature and evaporated to dryness. Chromatography on silica (eluant: cyclohexane—ethyl acetate (1-1)) yielded 640 mg of the desired product which was used as is for the following step.

STEP D: Diphenylmethyl 4-cyano-[2,3-bis]-[(2-methoxy-ethoxy)methoxy] -phenyl]-aminoxy-acetate Using the procedure of Step D of Example 1, 640 mg of the product of Step C and 50 microliters of hydrazine hydrate were reacted to obtain 320 mg of the expected product.

STEP E:
[[[1-[4-cyano-2,3-bis-[(2-methoxy-ethoxy)-methoxy]
-phenyl]
-2-oxo-2-(diphenylmethoxy)-ethyl]-oxy]-imino]2-
[(triphenylmethyl)-amino] -thiazole-4-yl-acetic acid Using the procedure of Step E of Example 1, 320 mg of the product of Step C and 234 mg of triphenylamino-thiazol-4-yl acetic acid were reacted to obtain 550 mg of the desired product.

NMR Spectrum CDCl$_3$ ppm 3.32 (s), 3.37 (s): OCH$_3$'s; 3.48 (t) 3.60 (t) 3.75 (m) 4.03 (m): centrl CH$_2$'s; 5.13 (AB), 5.24 (AB), O-CH$_2$-O's; 6.27 (s):

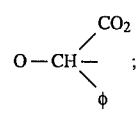

6.74 (s) : H$_5$ thiazole; 6.29 (s) : —CO$_2$-CH-Co$_2$; 7.09 to 7.32: aromatic H's; 2.60 mobile H: NH

STEP F:
4-methoxy-benzyl-7δ-[[[[[1-[4-cyano-2,3,-bis-
[(2- methoxy-ethoxy) -methoxy]
-phenyl]-2-oxo-2-(diphenylmethoxy)-ethyl]-
oxy]-amino]
[2-(triphenylmethyl)-amino]-thiazol-4-yl]-
acetamido]-3-[(Z)
-3-chloro-1-propenyl]-8-oxo-5-thia-1-azabicyclo-
oct-2-en-2 carboxylate Using the procedure of Step F of Example 1, 550 mg of the product of Step E were reacted to obtain after chromatography on silica (eluant: methylene chloride—ethyl acetate (8-2)), 580 mg of the desired product.

STEP G: 4-methoxy-benzyl
7δ-[[[[[1-[4-cyano-2,3,bis-[(2-methoxy-ethoxy)-
methoxy]
-phenyl]-2-oxo-2-(diphenylmethoxy)-ethyl]-oxy]-
imino]
[2-(triphenylmethyl)-amino]-thiazol-4-yl]-acetamido]
-3-[(Z)
-3-iodo-1-propenyl]-8-oxo-5-thia-1-azabicyclo-oct-2-
en-2-carboxylate Using the procedure of Step G of Example 1, 580 mg of the product of Step F were reacted to obtain 615 mg of the desired product.

NMR Spectrum: $CDCl_3$ 3.25 (s), 3.27 (s), 3.37 (s), 3.2 to 3.6 (m): $OCH_3$'s and $CH_2S$'s; 3.44 (m), 3.60 (m), 3.80 (m): central $CH_2$'s; 4.01 (m): $CH_2$-I; 4.93 (d): $H_6$; 5.17 to 5.38 (m): O-$CH_2$-O's; 5.78 (dd, 5.86 (dd): $H_7$; 6.12 (m) : CH=CH-CH; 6.43, 6.46 (s) : O-CH-o; 6.75 (s), 6.76 (s) : $H_5$ thiazole; 6.83 to 7.45 (m) : aromatic H's, HC=, $CO_2$-CH-$ø_2$; 7.82, 8.15 (d): mobile H: CONH.

STEP H:
1-[3-[7δ-[[[[[1-[4-cyano-2,3-bis-[(2-methoxy-ethoxy)-
methoxy]
-phenyl]-2-oxo-2-(diphenylmethoxy)-ethyl]
-oxy]-imino]
[2-(triphenylmethyl)-amino]-thiazol-4-yl]-acetamido]-
2-[(4-methoxy-benzyloxy)-carbonyl]
-8-oxo-5-thia-1-azabicyclo[4,2,0]
[oct-2-en-3-yl]-2-propenyl]-thieno-(2,3-b)
pyridinium iodide Using the procedure of Step H of Example 1, 615 mg of the product of Step G and 290 microliters of thieno-(2,3-b)-pyridine were reacted to obtain after chromatography on silica (eluant methylene chloride—methanol (9-1)), 300 mg of the desired product.

NMR Spectrum: $CDCl_3$ ppm 3.20 (s), 3.26 (s), 3.35 (s), 3.37 (s): the $CH_3O$'s; 3.43 (m), 3.50 (m), 3.78 (m), 4.02 (m): central $CH_2$'s; 3.80, 3.81 (s): ø-O-$CH_3$; 4.93 (d,d); $H_6$; 5.76, 5.84 (m) : $H_7$; 5.71, 5.96 (m) : C-$CH_2$-$N^+$; 6.40, 6.45 (s):

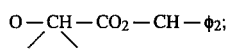

6.91 (m) =CH-$CH_2$ (E); 6.73, 6.74 (s): $H_5$ thiazole; 6.94 (m): aromatic H, —O-CH-$ø_2$, CH=CH—(ΔE); 7.05 to 7.45: the aromatic H's.

STEP I: Internal salt of (6R-(3-(E) 6α, 7δ-(Z)))-7-(3-(7-(((2-amino-4 -thiazolyl) (carboxy, (4-cyano-2,3-dihydroxyphenyl)-methoxy) -imino)-acetamido)-2-carboxy-8-oxo-5-thia-1-azabicyclo[4,2,0]oct-2-en-3-yl)-2 -propenyl)-thieno-(2,3-b) pyridinium Using the procedure of Step I of Example 1, 292 mg of the product of Step H were reacted to obtain 176 mg of the desired product.

NMR Spectrum: DMSO 5.18 (d,d): $H_6$; 5.82 (m) : $H_7$; 5.68 (d) : =C-CH-$N^+$; 5.93 (s,d): O-CH-o; 6.29 (m) : $CH_2$-CH=CH— (ΔE); 6.79 (s,d): $H_5$ thiazole; 6.94 (d,d), 7.03 (d) : aromatic H; 7.89 (d) $H_3$40 , 8.28 $H_2$', 8.15 $H_5$', 9.22 $H_4$': thieno pyridine; 9.54, 9.69: CO-NH-CH; 10.33: mobile H.

PREPARATION EXAMPLE 30

4-cyano-2,3-bis-[(2-methoxy-ethoxy)-methoxy]-
benzaldehyde

STEP A: 1,4-dicyano-2,3-dihydroxyphenyl 46 g of sodium ethylate were added to a mixture of 400 ml of tetrahydrofuran, 50 g of dicyanoethylsulfide and 52 g of diethyloxalate and the mixture was stirred for one hour and concentrated under reduced pressure. The residue was taken up in 600 ml of water and 250 ml of ethyl acetate and washed with ethyl acetate. The aqueous phase was acidified with concentrated hydrochloric acid and extraction was carried out with ethyl acetate. The extracts were evaporated to dryness under reduced pressure and the dry extract was taken up in 400 ml of nitromethane, followed by separation and washing with water to obtain 12.46 g of the desired product with a Rf=0.31 in $CH_2Cl_2$-MeOH 85-15.

STEP B: 1,4-dicyano-2,3-dimethoxy phenyl

A mixture of 1 g of the product of Step A, 60 ml of acetone, 3.15 g of potassium acetate and 1.5 ml of dimethyl sulfate was stirred for 16 hours at reflux, then cooled, filtered and evaporated to dryness under reduced pressure. The residue was chromatographed on silica (eluant: methylene chloride—hexane (9-1)) to obtain 820 mg of the desired product.

IR Spectrum: ($CHCl_3$)

conjugated CN 2240 $cm^{-1}$
aromatic 1595–1555 $cm^{-1}$

STEP C: 4-cyano-2,3-dimethoxy benzaldehyde 900 ml of toluene were added to a solution of 15.70 g of the product of Step B and 61 ml of a 1.5M solution of diisobutyl aluminium hydride in toluene were added over 15 minutes at −74° C. The mixture was stirred for 30 minutes at −70° C. to −74° C. and 20 ml of acetone were added slowly. The mixture was stirred for 10 minutes and then was poured into 700 ml of 1N hydrochloric acid and 200 ml of ethyl acetate. The mixture was stirred for 30 minutes at ambient temperature, followed by decanting and extracting with ethyl acetate. The extracts were dried and evaporated to dryness to obtain 15.5 g of the desired product. 4.9 g of a previous product were added to the dry extract and the 20.4 g of crude product was chromatographed on silica three times, eluting with toluene—ethanol (95-5) to obtain 7.5 g of the desired product.

NMR Spectrum: CDCl₃

4.06, 4.10: the O-CH₃'s; 7.38 (d) 7.60 (d): aromatic 2H, ortho coupling; 10.42 (s): CHO.

STEP D:
4-cyano-2,3-bis-[(2-methoxy-ethoxy)-methoxy]-benzaldehyde 124 ml of a molar solution of boron tribromide were added at −70° C. to a solution of 5.9 g of the product of Step C in 150 ml of methylene chloride and the mixture was stirred for 72 hours at ambient temperature, then cooled to −30° C. 30 ml of methanol were added slowly and the mixture was stirred for 30 minutes followed by evaporation to dryness under reduced pressure. The residue was taken up in 200 ml of ethyl acetate, washed with water, dried and evaporated to dryness under reduced pressure to obtain 6.4 g of residue to which was added 190 ml of methylene chloride. After cooling to 0° C., 21 ml of diisopropyl ethyl amine and 141 ml of methoxy ethoxy methyl chloride were added and the mixture was stirred for 3 hours at ambient temperature. The solution was washed with N hydrochloric acid, N sodium hydroxide and water, dried and evaporated to dryness. The residue was chromatographed on silica (eluant: methylene chloride—ethyl acetate (9-1)) to obtain 4.93 g of the desired product.

NMR Spectrum: CDCl₃

3.35, 3.38 (s): the O-CH₃'s; 3.53, 3.62, 3.88, 4.08 (m): central CH₂'s; 5.33, 5.39 (s): O-CH₂-O; 7.45 (dd=J=8 and 0.5 Hz): H₆; 7.67 (d, J=8 Hz): H₅; 10.39 (d,J=0.5 Hz): CHO.

EXAMPLE 31

Internal salt of (6R-(3-(E) 6α, 7δ-(Z)))-7-(3-(7-(((2-amino-4thiazolyl) (carboxy, (4-cyano-2,3-dihydroxy-phenyl)-methoxy)-imino)-acetamido)-2-carboxy-8-oxo-5-thia-1-azabicyclo[4,2,0]oct-2-en-3-yl) -2-propenyl)-quinolinium STEP A:
1-[3-[7δ-[[[[[1-(4-cyano-2,3-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl]-8-oxo-5-thia-1-azabicyclo[4,2,0]oct-2-en-3-yl]-2-propenyl] quinolinium iodide Using the procedure of Step H of Example 1, 615 mg of the product of Step G of Example 30 and 200 microliters of quinoline were reacted to obtain after chromatography on silica (eluant: methylene chloride—methanol (91-9)), 145 mg of the desired product.

STEP B: Internal salt of (6R-(3-(E) 6α, 7δ-(Z)))-7-(3-(7-(((2-amino-4 -thiazolyl) (carboxy-(4-cyano-2,3-dihydroxy-phenyl)-methoxy)-imino)-acetamido)-2-carboxy-8-oxo-5-thia-1-azabicyclo[4,2,0]oct-2 -en-3-yl)-2-propenyl) quinolinium Using the procedure of Step I of Example 1, 230 mg of the product of Step A were reacted to obtain 137 mg of the desired product.

NMR Spectrum: DMSO 3.30 to 3.8 (m) : CH₂-S; 5.15 (d): H₆; 5.60 (dd): H₇; 5.91, 5.93 (s):

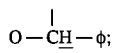

5.90 (m): CH₂-N⁺; 6.37 (m): HC=CH-CH₂; 6.93 (d, J=16) HC=CH-CH₂; 6.78, 6.94 (d): H₅', H₆'; 7.01 (s): H thiazole; 8.08, 8.28 (t): H₆", H₇"; 8.23 (dd) (J=6 and 8 Hz): H₃"; 8.51 (d) 8.55 (dd): H₅" and H₄" or H₈"; 9.34 (d, J=8 Hz) H₄" or H₈"; 9.55 (d, J=6 Hz): H₂";9.52 (d) 9.68 (d): HC-NH-CO.

EXAMPLE 32

Internal salt of (6R-(3-(E) 6α, 7δ-(Z)))-7-(3-(7-(((2-amino-4 -thiazolyl) (carboxy-(5-cyano-3,4-dihydroxy-phenyl)-methoxy)-imino) -acetamido)-2-carboxy-8-oxo-5-thia-1-azabicyclo [4,2,0]oct-2-en-3-yl) -2-propenyl)-thieno-(2,3-b)-pyridinium (RS isomer)

STEP A:
1-[3-[7δ-[[[[1-[5-cyano-3,4-bis-[(2-methoxy-ethoxy)-methoxy] -phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy) -carbonyl]-8-oxo-5-thia-1-azabicycl o[4,2,0][oct-2-en-3-yl]-2-propenyl)-thieno-(2,3-b)-pyridinium iodide (RS isomer)

Using the procedure of Step H of Example 2, 1.5 g of the product of Step G of Example 2 and 1.35 g of thieno-[2,3-b]-pyridine were reacted to obtain 1.22 g of the expected product (R/S mixture).

NMR Spectrum: CDCl₃ 300 MHz 3.27 (s), 3.29 (s), 3.35 (s), 3.36 (s): the C=OMe's; 3.80 (s), 3.81 (s): the =C-OMe's; 3.30 to 4.10: central CH₂'s and CH₂S's; approx. 5.00 to 5.11: the H₆'s; approx. 5.20 to 5.40: the O-CH₂-O's; 6.76 (s) and 6.77 (s): H₅ thiazoles; approx. 6.90 to 7.50: COOCH₂ and C₆H₅'s; 9.58 (d) resolved: the H₆"s; 7.52 to 8.90 the other quinoline H's; 8.22 and 8.34 (d): the =C-NH-CH's.

STEP B: Internal salt of (6R-(3-(E) 6<sup>α</sup>, 7δ(Z)))-7-(3-(7-(((2-amino-4 -thiazolyl) (carboxy-(5-cyano-3,4-dihydroxy-phenyl)-methoxy) -imino)-acetamido)-2-carboxy-8-oxo-5-thia-1- azabicyclo[4,2,0]oct-2-en-3-yl)-2 -propenyl)-thieno-(2,3-b)-pyridinium (R/S mixture).

Using the procedure of Step I of Example 1, 1.2 g of the product of Step A were reacted to obtain 730 mg of the desired product.

NMR Spectrum: DMSO 300 MHz 5.17 (d) resolved): H$_6$; 5.40 (s):

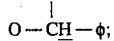

5.68 (d): CH$_2$-N$^+$; 5.79 (m): H$_7$; 6.87 (m): =C-CH=CH-CH$_2$ (Δ E); 6.77 (s) and 6.79 (s): H$_5$ thiazole; 7.12 and 7.17: aromatic and =C-CH=CH—; 7.89 (d): H$_3$'; 8.28 (d): H$_2$'; 8.15 (dd): H$_5$'; 9.09 (d): H$_4$'; 9.23 (d) resolved H$_6$'; 9.68 (d) resolved: NH; 10.38: mobile H; 7.39 (m): NH$_2$.

EXAMPLE 33

Internal salt of (6R-(3-(E) 6α, 7δ-(Z)))-7-(3-(7-(((2-amino-4-thiazolyl) (carboxy-(5-cyano-3,4-dihydroxy-phenyl)-methoxy)- imino) acetamido) -2-carboxy-8-oxo-5-thia-1-azabicyclo[4,2,0] oct-2-en-3-yl) -2-propenyl)-thieno-(2,3-b)-pyridinium (S isomer)

240 mg of the product were chromatographed on a microbondapack column, eluant: water, acetonitrile 82/18 (pH = 2.7) to obtain 45 mg of the desired product.

NMR Spectrum: DMSO 300 MHz 5.15 (d, J=5): H$_6$; 5.40 (s): O-CH-ø; 5.67 (d): =CH-CH$_2$-N$^+$; 5.80 (dd, J=5 and 8): H$_7$; 6.25 (m) : =CH-CH$_2$; 6.79 (s) : H$_5$ thiazole; 7.13 (m): aromatic and =CH-CH (ΔE); 7.89 (d, J= 6): 8.28 (d, J= 6): H$_3$' and H$_2$'; 8.15 (m) : H$_5$'; 9.09 (d, J=8): H$_4$'; 9.22 (d, J= 6): H$_6$'; 9.62 (d, J= 8): =C-NH-CH; 10.34, 10.43: OH; 7.33: the NH$_2$'s.

EXAMPLE 34

Internal salt of (6R-(3-(E) 6α, 7δ-(Z)))-1-(3-(7-(((2-amino-4-thiazolyl) (carboxy-(3-chloro-4,5-dihydroxy-phenyl)-methoxy) -imino) -acetamido)-2-carboxy-8-oxo-5-thia-1-azabicyclo [4,2,0]oct-2-en-3-yl) -2-propenyl)-imidazo-(1,2-a)-pyridinium STEP A:
[[[1-[3-chloro-4,5-bis-[(2-methoxy-ethoxy)-methoxy] -phenyl]-2-oxo-2-(diphenylmethoxy)-ethyl]-oxy]- imino] [2-[(triphenylmethyl)-amino] -thiazol-4-yl]-acetic acid Using the procedure of Step E of Example 1, 2.56 g of the product of Step D of Example 4 and 1.84 g of oxo-[2-[(triphenyl-methyl)-amino]-thiazol-4-yl]-acetic acid (Belgium Patent Application No. 864,828) were reacted to obtain after chromatography on silica (eluant: methylene chloride—methanol (97-3)), 3.34 g of the desired product with a Rf=0.54 (CH$_2$Cl$_2$-MeOH (9-1)).

STEP B: 4-methoxy-benzyl 7δ-[[[[[1-[3-chloro-4,5-bis-[(2-methoxy-ethoxy)- methoxy] -phenyl]-2-oxo-2-(diphenylmethoxy)-ethyl]-oxy]-imino] [2-(triphenylmethyl)-amino]-thiazol-4-yl]- acetamido]-3-[ (Z)-3-chloro-1-propenyl]-8-oxo-5-thia-1- azabicyclo[4,2,0]oct-2-en -2-carboxylate Using the procedure of Step F of Example 1, 1.42 g of 4-methoxy-benzyl 7δ-amino-3-[(Z)-3-chloro-1-propenyl]-8-oxo-5-thia -1-azabicyclo[4,2,0oct-2-en-2-carboxylate hydrochloride (EP 0,333,154) and 3.34 g of the product of Step A to obtain 2.88 g of the desired product with a Rf= 0.44 (CH$_2$Cl$_2$-ACOEt (8-2)).

STEP C: 4-methoxy-benzyl 7δ-[[[[[1-[3-chloro-4,5-bis-[(2-methoxy-ethoxy)- methoxy] -phenyl]-2 -oxo -2-(diphenylmethoxy)-ethyl]-oxy] -imino] [2-(triphenylmethyl)-amino]-thiazol-4-yl]-acetamido] -3-[(Z )-3-iodo-1-propenyl]-8-oxo-5-thia-1-azabicyclo [4,2,0]oct-2 -en-2 -carboxylate Using the procedure of Step G of Example 1, 1.88 g of the product of Step B were reacted to obtain 1.75 g of the desired product with a Rf= 0.52 (CH$_2$Cl$_2$-ACOEt (8-2)).

STEP D:
1-[3-[7δ-[[[[1-[3-chloro-4,5-bis-[(2-methoxy- ethoxy)-phenyl] -2-oxo-2-(diphenylmethoxy)-ethyl]-oxy]-imino] [2-(triphenylmethyl)-amino]-thiazol-4-yl]-acetamido]- 2-[(4-methoxy-benzyloxy-carbonyl] -8-oxo-5-thia-1-azabicyclo[4,2,0]oct-2-en-3-yl] -2-propenyl]-(1,2-a)-pyridinium iodide Using the procedure of Step H of Example 1, 876 mg of the product of Step C and 0,308 ml of imidazo-[1,2-a]- pyridine were reacted to obtain after chromatography on silica (eluant: methylene chloride—methanol (97-3)) 450 mg of the desired product.

NMR Spectrum (CDCl$_3$ 300 MHz 3.25, 3.29 (s); 3.35, 3.36 (s): the OCH$_3$'s; 3.43, 3.55, 3.72, 4.01 (m) : the central CH$_2$'s and CH$_2$S's; 3.78 (s,d) ø-O-Me; 4.94 (d,d) and 5.83 (m) : H$_6$ and H$_7$ (cis); 5.17 to 5.35 and 5.43 (d,t): OCH$_2$O, CO$_2$CH$_2$-ø, NCH$_2$-CH=; 5,94 (s) : O-CH-ø; 6.25 (m) : =CH-CH$_2$ (ΔE); 6.76 (s) : H$_5$ thiazole; 6.89—CH-ø$_2$; 6.85 to 7.40: ø-C, aromatic, CH=CH-C= (ΔE); 7.85 (d,d): H$_5$', H$_6$'; 8.05 (d,d): H $_4$'; 8.38 (d,d): H$_3$'; 8.64 (d,d): H$_1$'; 9.11 (d,d): H$_7$'; 7.97 to 8.19 (d) the NH's.

STEP E: Internal salt of (6R-(3-(E) 6α, 7δ-(Z)))-1-(3-(7-(((2-amino-4-thiazolyl) (carboxy-(3-chloro-4,5-dihydroxy-phenyl)-methoxy)-imino)-acetamido)-2-carboxy-8-oxo-5-thia-1-azabicyclo 4,2,0]oct-2-en-3-yl)-2-propenyl)-imidazo-(1,2-a)-pyridinium Using the procedure of Step I of Example 1, 489 mg of the product of Step D were reacted to obtain 187 mg of the expected product.

NMR Spectrum: DMSO 300 MHz 3.62: $CH_2S$; 5.29 (m): $N^+-CH_2-CH=$; 5.34 (s,d):

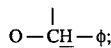

6.22 (m): $=CH-CH_2$ (E); 6.77 (s): $H_5$ thiazole; 6.85 (s); 6.90: $-CH-\phi_2$, aromatic and $CH=CH-CH_2$ (ΔE); 7.33: $NH_2$ and ø-C; 5.13 and 5.75: $H_6$-$H_7$; 7.58 (t): 8.06 (t): $H_5'$-$H_6'$; 8.28 (m): 8.44 (sl): $H_3'$-$H_2'$; 8.96 (d): $H_4'$; 9.59 (d,d): $H_7'$; 9.29 (sl), 13.03, 13.66: mobile H.

EXAMPLE 35

Internal salt of (6R-(3-(E) 6α, 7δ-(Z)))-1-(3-(7-(((2-amino-4-thiazolyl) (carboxy-(3-chloro-4,5-dihydroxy-phenyl)-methoxy)-imino)-acetamido-2 -carboxy-8-oxo-5-thia-1-azabicyclo[4,2,0]oct-2-en-3-yl) -2-propenyl)-4-methylthio pyridinium STEP A:
1-[3-[7δ-[[[[1-[3-chloro-4,5-bis-[(2-methoxy-ethoxy)-methoxy] -phenyl]-2 -oxo-2-(diphenylmethoxy)-ethyl]-oxy]-imino]-[2-(triphenylmethyl)-amino]-thiazol-4-yl]-acetamido]-2-[(4-methoxy-benzyloxy-carbonyl] -8-oxo-5-thia-1-azabicyclo[4,2,0]oct-2-en-3-yl]-2 -propenyl]-4 -methylthio pyridinium iodide Using the procedure of Step H of Example 1, 875 mg of the product of Step C of Example 34 and 385 mg of 4-S-methyl thiopyridine were reacted to obtain after chromatography on silica (eluant: methylene chloride methanol (97-3 then 90-10)), 389 mg of the desired product.

NMR Spectrum: $CDCl_3$ 300 MHz 2.61, 2.63: $S-CH_3$; 3.25, 3.28, 3.36, 3.37: the $OCH_3$'s; 3.78 (s): 3.79 (s): the oOMe's; 3.44, 3.58, 3.72, 4.01: the central $CH_2$'s and $CH_2$-S's; 4.97 (d,d): $H_6$; 5.05 to 5.35: $OCH_2O$, $CO_2CH_2$-ø, $CH_2N^+$ (1H); 5.56 (m); 5.85: $CH_2N^+$ (1H); 6.24, 6.39 (m): $CH=CHCH_2$ (ΔE); 6.78 (sl): $H_5$ thiazole; 6.89 (sl): $CO_2CH_2$-ø; 7 to 7.40: oC, aromatic and $=C-CH=CH-$ (ΔE); 7.66 (d,d) and 8.90 (m) thiopyridinium.

STEP B: Internal salt of (6R-(3-(E) 6α, 7δ-(Z)))-1-(3-(7-(((2-amino-4-thiazolyl) (carboxy-(3-chloro-4,5-dihydroxy-phenyl)-methoxy)-imino)-acetamido)-2 -carboxy-8 -oxo-5-thia-1-azabicyclo [4,2,0]oct-2 -en-3 -yl)-2-propenyl)-4-methylthio pyridinium Using the procedure of Step I of Example 1, 389 mg of the product of Step A were reacted to obtain 174.7 mg of the desired product.

NMR Spectrum: DMSO 300 MHz 2.72: $SCH_3$; 3.49 (s); 3.549 (d); 3.71 (d): $CH_2S$; 5.13, 5.17 (d): $H_6$ (cis); 5.76 (m) : $H_7$ (cis); 5.23 (m) : $N^+-CH_2$; 6.24: $=CH-CH_2$ (ΔE); 6.77 and 6.78 (s): $H_5$ thiazole; 6.85 to 7.02: aromatic and $=CH-CH=$; 7.95, 8.70: pyridinium; 9.30 (sl); 9.62 (d,d); 9.96 (ml): the mobile H's; 7.34: $NH_2$.

EXAMPLE 36

Internal salt of (6R-(3-(E) 6α, 7δ-(Z)))-1-(3-(7-(((2-amino-4-thiazolyl) (carboxy-(3-chloro-4,5-dihydroxy-phenyl)-methoxy)-imino) -acetamido)-2-carboxy-8-oxo-5-thia-1-azabicyclo [4,2,0]oct-2-en-3-yl)-2 -propenyl) quinolinium STEP A:
1-[3-[7δ-[[[[1-[3-chloro-4,5-bis-[(2-methoxy-ethoxy)-methoxy] -phenyl]-2-oxo-2-(diphenylmethoxy)-ethyl]-oxy]-imino] 2-[(triphenylmethyl)-amino]-thiazol-4-yl]-acetamido]-2-[(4-methoxy-benzyloxy-carbonyl] -8-oxo-5-thia-1-azabicyclo[4,2,0]oct-2-en-3-yl]-2 -propenyl]quinolinium iodide Using the procedure of Step H of Example 1, 900 mg of the product of Step C of Example 34 and 0.366 ml of quinoline were reacted to obtain after chromatography on silica (eluant:methylene chloride—methanol (97.3)), 384 mg of the desired product.

NMR Spectrum: $CDCl_3$ 300 MHz 3.24 s) , 3.29 (s) , 336 (s,d): the $O-CH_3$'s; 3.78 (s): ø-OMe; 3.40 (m), 3.58 (m), 3.71 (m), 4.00 (m): the central $CH_2$'s; 5.07 and 5.26, $CO_2CH_2$ø and $O-CH_2-O$; 4.94 (s): $H_6$; 5.04 (m), $H_7$; 6.00 to 6.20: $=CH-CH_2-N^+$; 5.99 (s) resolved: ø-CH-O; 6.38 (m), 6.55 (m): $=CH-CH_2$ (ΔE); 6.75 (s) resolved: $H_5$ thiazole; 6.85 to 7.40; aromatics and $=C-CH=CH-CH_2$; 7.91 (m), 8.08 to 826 (m), 8.42 (m), 8.95 (m), 10.49 (d): quinoline and mobile H.

STEP B: Internal salt of (6R-(3-(E) 6α, 7δ-(Z)))-1-(3-(7-(((2-amino-4 -thiazolyl) (carboxy-(3-chloro-4,5-dihydroxy-phenyl)-methoxy) -imino)-acetamido)-2-carboxy-8-oxo-5-thia-1-azabicyclo [4,2,0]oct-2-en-3-yl)-2-propenyl) quinolinium Using the procedure of Step I of Example 1, 384 mg of the product of Step A were reacted to obtain 192 mg of the desired product.

NMR Spectrum: DMSO 300 MHz 3.35 to 3.70: $CH_2S$; 5.11 (d, J=5); 5.15 (d, J= 5): $H_6$; 5.32 (o) 5.34 (s):

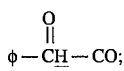

5.74 (m): $H_7$; 5.89 (m): $=CH-CH_2-N$; 6.36: $=CH-CH_2$; 6.75 to 7.00 (m) : other CH=, aromatic and $H_5$ thiazole; 7.33: mobile H's, 8.07, 8.26, 8.52, 9.33: quinoline; 9.57, 9.29, 9.60, 9.91 (m) 13.00 (eq) 13.70 (m): mobile H's.

EXAMPLE 37

Internal salt of (6R-(3-(E) 6α, 7δ-(Z)))-1-(3-(7-(((2-amino-4-thiazolyl) (carboxy)-3,4-dihydroxy-2-fluorophenyl]-methoxy)- imino)-acetamido)-2 -carboxy-8-oxo-5-thia-1-azabicyclo[4,2,0] oct-2-en-3-yl) -2 -propenyl)-quinolinium

STEP A
:1α-(hydroxy)-2-fluoro-(3,4-bis-[(2-methoxy-ethoxy)-methoxy] phenyl]-acetic acid Using the procedure of Step A of Example 1, 15.5 g of 2-fluoro -3,4-bis-[(2-methoxy-ethoxy]-methoxy]-benzaldehyde were reacted to obtain 20.7 g of the desired product which was used as is for the following step.

STEP B: Diphenylmethyl [2-fluoro-(3,4-bis-[(2-methoxy-ethoxy]-methoxy] -phenyl]-hydroxy acetate Using the procedure of Step B of Example 1, 20.6 g of the product of Step A and 9.08 g of diphenyl diazometane were reacted to obtain after chromatography on silica (eluant: cyclohexane—ethyl acetate (7-3)), 3.2 g of the desired product.
IR Spectrum: CHCl$_3$
OH 3600 cm$^{-1}$ and 3530 cm$^{-1}$
C=O 1733 cm$^{-1}$
Aromatics 1620, 1603, 1588, 1498 cm$^{-1}$

STEP C: Diphenylmethyl [2-fluoro-(3,4-bis-[(2-methoxy-ethoxy)-methoxy] -phenyl]-phthalimidoxy acetate Using the procedure of Step C of Example 1, 3.2 g of the product of Step B were reacted to obtain after chromatography on silica, (eluant: methylene chloride—acetone (95-5)), 2.9 g of the desired product.
IR Spectrum (CHCl$_3$
C=O 1754, 1737 cm$^{-1}$
Aromatics 1619, 1597, 1498 cm$^{-1}$

STEP D: Diphenylmethyl aminoxy-[2-fluoro-(3,4-bis-[(2-methoxy-ethoxy)-methoxy]-phenyl]-acetate Using the procedure of Step D of Example 1, 1.05 g of the desired product were obtained.
IR Spectrum: CHCl$_3$
O-NH$_2$ 3340 cm$^{-1}$
C=O 1744 cm$^{-1}$
starting NH$_2^+$1620, 1580, 1498 cm$^{-1}$
Aromatic

STEP E:
[[[1-[2-fluoro-(3,4-bis-[(2-methoxy-ethoxy)-methoxy]-phenyl] -2-oxo-2-(diphenylmethoxy)-ethyl]-oxy]-imino]- [2-[(triphenyl)-amino]-thiazol-4-yl acetic acid Using the procedure of Step E of Example 1, 1.05 g of the product of Step D and 0.777 g of oxo-[2-[(triphenylmethyl)-amino]-thiazol-4-yl acetic acid (Belgium Application No. 864,828) were reacted to obtain 1.74 g of the desired product which was used as is for the following step.

STEP F: 4-methoxy-benzyl 7δ-[[[[[1-[2-fluoro-3,4-bis-[(2-methoxy-ethoxy)-methoxy] -phenyl]-2-oxo-2-(diphenylmethoxy)-ethoxy] -oxy]imino] [2-(triphenylmethyl)-amino]-thiazol-4-yl] -acetamido]-3-[(Z) 3-chloro-1-propenyl-8-oxo-5-thia-1-azabicyclo[4,2,0] oct-2-en-2-carboxylate Using the procedure of Step F of Example 1, 1.74 g of the product of Step E and 0.784 g of 4-methoxy-benzyl 7δ-amino-3-[(Z) -3-chloro-1-propenyl]-8-oxo-5-thia-1-azabicyclo[4,2,0]oct-2-en-2-carboxylate were reacted to obtain after chromatography on silica (eluant: methylene chloride -ethyl acetate (8-2)), 1.7 g of the desired product which was used as is for the following step.

STEP G: 4-methoxy-benzyl 7δ-[[[[[1-[2-fluoro-(3,4-bis-[(2-methoxy-ethoxy) -methoxy]-phenyl]-2-oxo-2-(diphenyl-methoxy)-ethyl] -oxy]-imino]-[2-[(triphenylmethyl)-amino]-thiazol-4-yl] -acetyl]-amino] -3-[(Z)-3-iodo-1-propenyl-8-oxo-5-thia-1- azabicyclo[4,2,0] oct-2-en-2-carboxylate Using the procedure of Step G of Example 1, 840 mg of the product of Step F were reacted to obtain 814 mg of the desired product with a Rf=0.45 (CH$_2$Cl$_2$-ACOEt (8-2)).

STEP H:
1-[3-[7δ-[[[[1-[2-fluoro-(3,4-bis-[(2-methoxy-ethoxy] -methoxy]-phenyl]-2-oxo-2-(diphenylmethoxy)- ethyl]-oxy]-imino] [2-(triphenylmethyl)-amino]-thiazol-4-yl]- acetamido]-2-[(4-methoxy-benzyloxy)-carbonyl] -8-oxo-5-thia-1-azabicyclo[4,2,0]oct-2-en-3-yl] -2-propenyl quinolinium iodide Using the procedure of Step H of Example 1, 814 mg of the product of Step G and 0.337 ml of quinoline were reacted to obtain after chromatography on silica (eluant: methylene chloride—methanol (98-2) 368 mg of the expected product.
NMR Spectrum: CDCl$_3$ 300 MHz
3.31 to 3.35: the O-CH$_3$'s; 3.45 (d, J=16): CH$_2$S; 3.51, 3.81, 3.94: the central CH$_2$'s; 3.79 (s) 3.80 (s): the Oø-O-CH$_3$'s; 4.91 (m): H$_6$; 5.15 to 5.30: CO-CH$_2$-ø, O-CH$_2$-O; 5.83: H$_7$; 6.05 (ml): =C-CH$_2$-N$^+$; 6.31 and 6.35 (m) : the O-CH-ø's; 6.49 (ml): CH$_2$-CH-CH; 6.72, 6.75: H$_5$ thiazole; 6.87 to 7.40: aromatics, CO$_2$-CHø$_2$, CH=CH-C; 7.90 to 8.20: quinoline, 8.40 (d,d): H$_4$'; 8.90 (d,d): H$_2$'.

STEP I: Internal salt of (6R-(3-(E) 6α, 7δ-(Z)))-1-(3-(7-(((2-amino-4 -thiazolyl ((carboxy -(3,4-dihydroxy-2-(fluoro-phenyl)-methoxy) -imino)-acetamido)-2-carboxy-8-oxo-5-thia-1-azabicyclo [4,2,0]oct-2-en-3-yl)-2-propenyl) quinolinium Using the procedure of Step I of Example 1, 357 mg of the product of Step H were reacted to obtain 176.9 mg of the desired product.
NMR Spectrum: DMSO 300 MHz
5.14: the H$_6$'s; 5.41 (s) resolved: O-CH-ø; 5.70 to 5.90: 2 CH$_2$N$^+$ and H$_7$; 6.54 (d, J=8.5) and 6.70 to 6.80: aromatic and H$_5$ thiazole; 6.37 (m): —CH=CH-CH$_2$ (ΔE); 6.97 (d, d): —CH=CH-CH$_2$; 7.34 (l): NH$_2$; 8.07 to 9.58: quinoline; 9.16, 9.49, 9.69: mobile H's.

PREPARATION OF EXAMPLE 37

2-fluoro-3,4-bis-[(2-methoxy-ethoxy)-methoxy]benzaldehyde

STEP A: 2-fluoro-3,4-bis-dihydroxy-benzaldehyde

A mixture of 74.3 g of hexamethylenetetramine and 125 ml of trifluoroacetic acid was stirred for 2 hours at 80° C. and then a solution of 34 g of 3-fluorocatechol in 130 ml of trifluoroacetic acid was added. The mixture was stirred for 2 hours at 80° C. and for 16 hours at ambient temperature. The trifluoroacetic acid was distilled at reduced pressure and the residue was taken up in water and neutralized by the addition of potassium carbonate until a pH of 7 wa achieved. After filtration and extraction with ether, the extracts were dried and evaporated to dryness under reduced pressure to obtain 39 g of the product which was used as is for the following step.

STEP B: 2-fluoro-3,4-bis-[(2-methoxy-ethoxy)-methoxy]-benzaldehyde 261 ml of N-ethyl diisopropylamine were added to a solution of 39 g of the product of Step A in 390 ml of acetonitrile and the mixture was cooled to –5° C. 113 ml of (2-methoxyethoxy) methyl chloride were added slowly and the mixture was stirred for 16 hours at –5° C. The acetonitrile was evaporated and the residue was taken up in 250 ml of methylene chloride, then washed with N hydrochloric acid, with water, with N sodium hydroxide and then with water, followed by drying, filtering and evaporating to dryness under reduced pressure to obtain 49.5 g of product which was chromatographed on silica (eluant: methylene chloride—acetone (96-4)) to obtain 10.4 g of the desired product.

NMR Spectrum: CDCl$_3$ 200 MHz 3.37, 3.38 (s): the OCH$_3$'s; 5.24 (s); 5.37 (s): the O-CH$_2$-O's; 3.56 (m), 3.83 (m), 4.00 (m): the central CH$_2$'s; 10.26 (s): CHO; 7.03 (dd J= 1.5–9): H$_4$; 7.59 (dd J=7.5–9): H$_3$.

EXAMPLE 38

Internal salt of (6R-(3-(E) 6$^\alpha$, 7$^\delta$(Z)))-1-(3-(7-(((2-amino-4-thiazolyl) (carboxy--(3,4-dihydroxy-2-fluorophenyl)-methoxy)-imino)-acetamido)-2 -carboxy-8-oxo-5-thia-1-azabicyclo[4,2,0oct-2-en-3-yl) -2-propenyl)-imidazo(1,2-a)pyridinium

STEP A: 1-[3-[7$^\delta$-[[[[[1-[2-fluoro-(3,4-bis-[(2-methoxy-ethoxy)-methoxy]-phenyl]-2-oxo-2-(diphenylmethoxy)-ethyl]-oxy]-imino] [2-(triphenylmethyl)-amino]-thiazol-4-yl]-acetamido]-2-[(4-methoxy-benzyloxy)-carbonyl] -8-oxo-5-thia-1-azabicyclo[4,2,0oct-2-en-3-yl] -2-propenyl-imidazo(1,2-a)pyridinium iodide Using the procedure of Step H of Example 1, 704.5 g of the product of Step G of Example 37 and 0.25 ml of imidazo(1,2-a) pyridine were reacted to obtain after chromatography on silica (eluant:methylene chloride—methanol (95-5), 275 mg of the expected product.

NMR Spectrum: CDCl$_3$ 400 MHz 3.32, 3.33 (s); the —OCH$_3$'s; 3.46, 3.47 (d): CH$_2$S; 3.78 (m): the o-O-CH$_3$'s; 3.53, 3.81, 3.95: the central CH$_2$'s; 4.82: H$_6$; 5.78: H$_7$; 5.00 to 5.32: OCH$_2$O—, CO$_2$CH$_2$ø, =CH-CH$_2$N$^+$; 5.40: the other H of CH$_2$N$^+$; 6.32, 67.37 (s): O-CH-ø; 6.28 (m): CH$_2$-CH=CH (ΔE); 6.74 (s) 6.76 (s) : H$_5$ thiazole; 6.8 to 7.40: oC, COCH$_2$-o$_2$, aromatic, =CH-CH=CH (ΔE); 7.84 (m) to 9.13 (5H) imidazo pyridinium.

STEP B: Internal salt of (6R, (3-(E) 6$^\alpha$, 7$^\delta$(Z)))-1-(3-(7-(((2-amino-4 -thiazolyl) (carboxy-(3,4-dihydroxy-2-fluoro-phenyl-methoxy) -imino)-acetamido)-2-carboxy-8-oxo-5-thia-1-azabicyclo [4,2,0]oct-2-en-3-yl)-2-propenyl)-imidazo (1,2-a)pyridinium Using the procedure of Step I of Example 1, 275 mg of the product of Step A were reacted to obtain 116.2 mg of the desired product.

NMR Spectrum: DMSO 300 MHz 3.60: CH$_2$S; 5.11, 5.14 (d): H$_6$; 5.75 (dd) 5.79 (dd): H$_7$; 5.30 (m): CH$_2$N$^+$; 5.64, 5.65 (s): O-CH-ø; 6.25 (m): CH=CH—; 6.91, 6.93 (d): CH=CH-CH$_2$; 6.57, 6.74 (m): H$_5$" and H$_6$"; 6.77 (s) 6.79 (s): H$_5$ thiazole; 7.57, 8.05 (dd): H$_5$' and H$_6$'; 8.22 (d) 8.98 (dd):H$_4$', H$_7$40 ; 8.30 8.46 (m): H$_2$', H$_3$', 9.48 (d) 9.55 (d): CH-NH-C=O; 7.32, 9.13, 9.64 (m): mobile H's.

EXAMPLE 39

Internal salt of (6R-(3-(E) 6$^\alpha$, 7$^\delta$(Z)))-1-(3-(7-(((2-amino-4-thiazolyl) (carboxy-(2,5-difluoro-3,4-dihydroxyphenyl)-methoxy)-imino) -acetamido)-2-carboxy-8-oxo-5-thia-1-azabicyclo [4,2,0]oct-2-en-3 -yl)-2-propenyl)-imidazo (1,2-a)pyridinium

STEP A: Diphenylmethyl [2,5-difluoro-3,4-bis-dihydroxy]-phenyl-hydroxy acetate Using the procedure of Step B of Example 1, 3.30 g of [2,5-difluoro-3,4 -bis-dihydroxy]-phenyl hydroxy acetic acid and 2.77 g of diphenyl diazomethane were reacted to obtain after chromatography on silica (eluant: cyclohexane—acetone (6-4)), 3.75 g of the desired product.

IR Spectrum

Complex absorptions OH/NH region

C=O 1752 cm$^{-1}$

Aromatic 1630–1535–1485 cm$^{-1}$

STEP B: Diphenylmethyl [2,5-difluoro-3,4-bis-[(2-methoxy-ethoxy)-methoxy)-phenyl] -hydroxy-acetate 2.96 g of diisopropylethylamine and 10 ml of methylene chloride were added to a solution of 4.21 g of the product of Step A in 45 ml of methylene chloride and the mixture was cooled to –5° C. 2.71 g of methoxy-ethoxymethyl chloride and 5 ml of methylene chloride were added slowly and the mixture was stirred for 30 minutes at –5° C. and poured into 30 ml of 0.1N hydrochloric acid. The mixture was decanted and washed with a saturated solution of sodium bicarbonate (pH 8), drying, filtering and concentrating to dryness under reduced pressure to obtain 6.9 g of product which was chromatographed on silica (eluant: methylene chloride—ethyl acetate (85-15)) to obtain 3,577 g of the desired product.

IR Spectrum: CHCl$_3$ approx. 3600 cm$^{-1}$ (f)—3530 cm$^{-1}$ complex: OH 1734 cm$^{-1}$: C=O 1624-1600-1589-1492 cm$^{-1}$: aromatic.

NMR Spectrum 19$_F$ 140.6 F$^2$, J$_{F1-F4}$=14, J$_{F1H5}$=6.5

135.2 F$^5$, J$_{F4-F5}$=11.

STEP C: Diphenylmethyl
2,5-difluoro-3,4-bis-[(2-methoxy-ethoxy)-methoxy)-
phenyl]-phthalimidoxy acetate Using the procedure of Step C of Example 1, 4.419 g of product of Step B and 1.41 g of hydroxyphthaliideand 4.12 g of triphenyl-phosphine were reacted to obtain after chromatography on silica (eluant: methylene chloride—acetone (97-3) then cyclohexane—ethyl acetate (1-1)), and 2.56 g of the desired product.

NMR Spectrum: CDCl$_3$ 300 MHz 3.33 (s), 3.36 (s): OCH$_3$; 3.50 (m), 3.91 (m): O-CH$_2$-CH$_2$-O; 5.20 (A, B system) 5.26 (A, B system): OCH$_2$O; 6.26 (s):

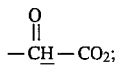

6.94 (s): CO$_2$CH Ph$_2$—; 7.15, 7.3 (m); 7.76 (m): aromatic H's.

STEP D: Diphenylmethyl aminoxy-[2,5-difluoro-3,4
-bis-[(2-methoxy-ethoxy)-methoxy)-phenyl] -acetate Using the procedure of Step D of Example 1, 2,537 g of the product of Step C and 0.21 ml of hydrazine hydrate were reacted to obtain after chromatography on silica (eluant: cyclohexane—ethyl acetate (1-1)), 1.67 g of the desired product is obtained.

NMR Spectrum $^{19}$F: CDCl$_3$ 135.5 (dd) F$_5$ 139.8 (dd) F$_2$

J$_{F5-F2}$=14

J$_{F5-H6}$=10.5

J$_{F2-H6}$=6

STEP E:
[[[1-[2,5-difluoro-3,4-bis-[(2-methoxy-ethoxy)-
methoxy)-phenyl]
-2-oxo-2-(diphenylmethoxy]-ethyl]-oxy]-imino]
[2-[(triphenylmethyl) -amino]-thiazol-4-yl]acetic
acid Using the procedure of Step E of Example 1, 909 mg of the product of Step D and 652 mg of oxo-[2-[(triphenylmethyl)-amino]-thiazol] -4-yl]-acetic acid Belgian Application No. 864,828) were reacted to obtain after chromatography on silica (eluant: methylene chloride—methanol (96-4)), 1.138 g of the desired product is obtained.

IR Spectrum

=C-NH+approx. 3405 cm$^{-1}$ general absorption OH/NH

C=O 1740-1727 cm$^{-1}$

C=N

Aromatic+1615-1597-1526-1495 cm$^{-1}$

Heteroaromatic

STEP F: 4-methoxy benzyl
7δ-[[[[1-[2,5-difluoro-3,4-bis[
(2-methoxy-ethoxy)-methoxy]-phenyl]-2-oxo
-2-(diphenyl-methoxy)-ethyl]-oxy] -imino]
[2-[(triphenylmethyl)-amino]-thiazol-4-yl]-acetyl]-
amino]
-3-[(Z)-3-chloro-1-propenyl]-8-oxo-5-thia-1-azabicyclo
[4,2,0] oct-2 -en-2-carboxylate Using the procedure of Step F of Example 1, 1.12 g of the product of Step E were reacted to obtain after chromatography on silica (eluant: methylene chloride—ethyl acetate (9-1)), 979 mg of the expected product.

NMR Spectrum: CDCl$_3$ 400 MHz 3.08, 3.20, 3.40: CH$_2$S; 3.34, 3.35 (s): the C-O-CH$_3$'s; 3.54, 3.92 (m): the central CH$_2$'s; 3.80, 3.81 (s): Ar-O-CH$_3$; 3.70, 4.00: CH=CH$_2$Cl; 4.95, 5.03: H$_6$ cephalo; 5.16, 5.25: OCH$_2$O, CO$_2$CH$_2$Ar; 5.75 (m) : =CH-CH$_2$ (ΔZ); 5.85, 6.00: H$_7$ cephalo, =CH-CH$_2$; 6.26 (d, J= 11) 6.35 (m) : C-CH=CH-CH$_2$Cl, ARCHO; 6.70, 678 (m) : H$_5$ thiazole; approx. 7.00 to 7.35: aromatic H's; 7.80, 8.30: NH-CH.

STEP G: 4-methoxy-benzyl
7δ-[[[[1-[2,5-difluoro-3,4-bis-[(2-methoxy
-ethoxy)-methoxy]-phenyl]-2-oxo-2-
(diphenyl-methoxy)-ethyl] -imino]
[2-(triphenylmethyl)-amino]-thiazol-4-yl]-
acetamido]-3-[ (Z)-3 -iodo-1-propenyl]-8-oxo-5-
thia-1-azabicyclo[4,2,0] oct-2-en-2-carboxylate Using the procedure of Step G of Example 1, 969 mg of the product of Step F were reacted to obtain 725 mg of the expected product.

STEP H: 1-[3-[7δ-[[[[1-[2,5-difluoro-3,4-bis-
[(2-methoxy-ethoxy)-methoxy]
phenyl]-2-oxo-2-(diphenylmethoxy)-ethyl]-oxy]
-imino]
[2-(triphenylmethyl)-amino]-thiazol-4-yl]-acetamido]-
2-[ (4-methoxy-benzyloxy)-carbonyl]-8-oxo-5-thia-1-
azabicyclo[4,2,0]
oct-2-en-3-yl]-2-propenyl]-imidazo (1,2-a)
pyridinium iodide Using the procedure of Step H of Example 1, 717 mg of the product of Step G and 313 mg of imidazo(1,2-a)pyridine were reacted to obtain after chromatography on silica (eluant: methylene chloride—methanol (95-5)), 350 mg of the desired product.

NMR Spectrum: CDCl$_3$ 400 MHz 3.32, 3.33, 3.34 (s): C-O-CH$_3$; 3.53, 3.92 (m): central CH$_2$'s; 3.30, 3.80: CH$_2$S; 3.79, 3.80 (s) : Ar-O-CH$_3$; 4.94 (dd): H$_6$ cephalo; 5.80, 5.88 (d) after exchange: H$_7$ cephalo; (td); 6.31 (td): =CH-CH$_2$N$^+$; 6.31 (s) 6.37 (s): Ar-CH-CO$_2$; 7.84, 8.18 (d): CO-NH-CH; 7.86, 8.02 (m): heterocycle; 8.32 to 9.18: imidazopyridine; 6.75, 7.45 (m): aromatic, H$_5$ thiazole, CH-CH-CH$_2$, CO$_2$-CH-ø$_2$; 5.18, 5.30, 5.43: CH$_2$-N$^+$, OCH$_2$O,

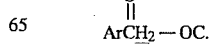

STEP I: Internal salt of (6R-(3-(E) 6α, 7δ(Z)))-1-(3-(7-(((2-amino-4 -thiazolyl) (carboxy-(2,5-difluoro-3,4-dihydroxyphenyl)-methoxy)-imino)-acetamido) -2 -carboxy-8-oxo-5-thia-1-azabicyclo [4,2,0]oct-2-en-3-yl)-2-propenyl)-imidazo (1,2-a) pyridinium Using the procedure of Step I of Example 1, 344 mg of the product of Step H were reacted to obtain 170 mg of the expected product.

NMR Spectrum: DMSO 300 MHz 5.16 (dd): L $H_6$ cephalo; 5.77 (m): $H_7$ cephalo; 5.29 (m): $CH_2-N^+$; (s,d):

ArC$\underline{H}$;

6.70 (dd): aromatic H coupled with 2F; 6.80 (s,d): $H_5$ thiazole; 6.87 (dd): CH=CH-$CH_2$ (ΔE): 7.33 (sl): $NH_2$; 8.28, 8.44 (m) : $H_2$' and $H_3$'; 7.18 to 8.96 (4H) imidazopyridine; 9.03, 9.63 (d) : C-NH-CH; 9.84 other mobile H's.

PREPARATION OF EXAMPLE 39

2,5-difluoro-3,4-dihydroxy]-phenyl hydroxy-acetic acid

STEP A: 2,5-difluorophenol 325 ml of n-butyl lithium in a 1.6M solution with hexane were added at −65° C to a solution of 62.19 g of 1,4-difluorobenzene in 500 ml of tetrahydrofuran and the mixture was stirred for 150 minutes. Then, a solution of 53.8 g of trimethylborate in 250 ml of ether was added over 30 minutes at −65° C. and the mixture was stirred for 90 minutes, allowing the temperature to rise to −15° C. The mixture was stirred for 15 minutes and 350 ml of 10% hydrochloric acid were added. After decanting, the residue was washed with water, dried and evaporated to dryness under reduced pressure to obtain 63.5 g of product which was taken up in 400 ml of toluene. After heating to 108° C. 180 ml of 30% hydrogen peroxide were added dropwise and heating was continued for 2 hours at 90° C. The medium was allowed to cool and was filtered. The filtrate was decanted and the organic phase was washed with water, then with a 10% solution of ferrous ammonium sulfate, then with water. The organic phase was extracted twice with 300 ml of 2N sodium hydroxide and acidification was carried out with concentrated hydrochloric acid, followed by extraction with methylene chloride. The extracts were dried and evaporated to dryness under reduced pressure to obtain the desired product.

NMR Spectrum: $CDCl_3$ 5.21 (sl): OH; 6.55 (dddd): $H_4$, $JH_4-H_2$=9, $JH_4-F_2$=3.5, $JH_4-H_6$=3, $JH_4F_5$= 8; 6.74 (ddd): $H_6$, $JH_6-H_4$=3, $JH_6-F_2$= 7; 7.01 (ddd); $H_3$, $JH_3H_4$=9, $JH_3-F_2$= 10, $JH_3-F_5$= 5.

STEP B: 2,5-difluoroanisole 35.0 g of the product of Step A, 350 ml of acetone, 44.6 g of potassium carbonate and 40.7 g of dimethyl sulfate (neutralized on potassium bicarbonte) and was allowed to return to ambient temperature. Water was added and extraction was carried out with ether. The extracts were washed, dried and concentrated to dryness under reduced pressure to obtain 39.8 g of the desired product.

NMR Spectrum: $^{19}F$ $CDCl_3$ 188 MHZ 119.1 (dddd) $F_5$ 144.1 (dddd) $F_2$ $J_{F2-F5}$= 15

$J_{F5-H3}$= 5 $J_{F2-H3}$= 10.5

$J_{F5-H4}$= 8 $J_{F2-H4}$= 3.5

$J_{F5-H6}$= 10 $J_{F2-H6}$= 7

STEP C: 3,6-difluoroguaiacol

Using the procedure of Step A, 55.15 g of the product of Step B and 220 ml of n-butyl lithium, 1,6M in hexane, 36.4 g of trimethyl borate and 200 ml of 30% hydrogen peroxide were reacted to obtain 44.7 g of the desired product.

NMR Spectrum: $CDCl_3$ 200 MHz 4.02 (d, J= 2) $OCH_3$ 5.56 (sl) OH 6.57 (ddd ) $H_4$ 6.75 (dt) $H_5$ $J_{H5-H4}$=9.5; $J_{H5-F3}$= 5; $J_{H5-F-6}$=9.5; $J_{H4-F3}$=10.5; $J_{H4-F6}$= 5.

STEP D: 3,6 difluorocatechol

Using the procedure of Step B of Preparation 1, 21.15 g of the product of Step C and 260m 1 of a molar solution of boron tribromide were reacted to obtain 17.62 g of the desired product.

STEP E: 2,5-difluoro-3,4-dihydroxy]-phenyl-hydroxy-acetic acid 7.69 g of sodium hydroxide dissolved in 80 ml of water were added at +10° C. to a solution of 11.7 g of the product of Step D and 7.37 g of monohydrated glyoxylic acid in 40 ml of water and the mixture was stirred for 30 minutes at 10° C. then for 3 hours 30 minutes at ambient temperature. 0.74 g of monohydrated glyoxylic acid were added and the mixture was stirred for one hour at ambient temperature. Concentrated hydrochloric acid was added until a pH of 1 was achieved. Extraction was carried out with ethyl acetate and the extracts were dried, filtered and concentrated to dryness under reduced pressure to obtain 17.0 g of the desired product.

IR Spectrum: Nujol

Complex absorption OH/NH region

C=O 1700 $cm^{-1}$

Aromatic 1640, 1612, 1526, 1488 $cm^{-1}$

EXAMPLE 40

Internal salt (6R-(3-(E) 6α, 7δ(Z)))-1-(3-(7-(((2-amino-4-thiazolyl) (carboxy-(2-chloro-4,5-dihydroxy-3-methoxy-phenyl)-methoxy) -imino)-acetamido)-2-carboxy-8-oxo-5-thia-1-azabicyclo [4,2,0]oct-2-en-3-yl)-2 -propenyl)-imidazo-(1,2-a) pyridinium

STEP A:

[2-chloro-4,5-bis-[(2-methoxy-ethoxy)-methoxy]-3-methoxy] benzaldehyde and 2-chloro-3,4-bis-[(2-methoxy-ethoxy)-methoxy]-5-methoxy benzaldehyde 2.17 g of 3,4-bis-[(2-methoxy-ethoxy)-methoxy]-5-methoxy benzaldehyde and 21.7 ml of methylene chloride and 4 ml of a solution of 1.76 g of calcium hypochlorite (at 65%) in 10 ml of water were stirred for 20 minutes at 0° to +5° C.

Extraction was carried out with methylene chloride and the extracts were washed with water, dried and evaporated to dryness under reduced pressure to obtain 2.34 g of a mixture of isomers (7/3).

NMR Spectrum: CDCl₃ 250 MHz 3.37: the OCH₃'s; 3.7 to 4.1: the central CH₂'s; 5.29 to 5.33: OCH₃; 3.91: OCH₃; 7.54 and 7.30: H₆; 10.38 and 10.40: CHO.

STEP B:
[2-chloro-4,5-bis-[(2-methoxy-ethoxy)-methyl]-3-methoxy-styryl carboxylate and corresponding 5-methoxy isomer 2.97 ml of triethylamine, then a solution of 6.72 g of the mixture of isomers of Step A dissolved in 60 ml of tetrahydrofuran were added to a stirred mixture, a +5° to +10° C. of 2.162 g of lithium bromide with 60 ml of tetrahydrofuran and 4.03 ml of triphenylphosphoro-acetate. The mixture was stirred for 16 hours at ambient temperature and concentrated to dryness under reduced pressure. The residue was taken up in methylene chloride, washed with 1N hydrochloric acid, then with water, dried and evaporated to dryness under reduced pressure to obtain 8.9 g of the expected product (mixture of 2 isomers 7/3).

NMR Spectrum: CDCl₃ 250 MHz 1.35 (t,d) 4.28 (q,d): CO₂Et; 3.37, 3.38: the OCH₃'s; 3.57 (m); 3.84 to 4.04 (m): the central CH₂'s; 3.88 (s); 3.86 (s): OCH₃; 5.24 to 5.28: the OCH₂'S; 6.34 (d), 6.38 (d): CH=CH-CO₂; 8.03, 8.05 (d): —CH=CH-CO₂; 6.93, 7.30: aromatic H.

STEP C:
[2-chloro-4,5-bis-[(2-methoxy-ethoxy)-methoxy]-3-methoxy] styrol and corresponding 5-methoxy isomer 11.7 ml of a molar solution of diisobutyl aluminium hydride in hexane were added to a solution cooled to −70° C. of 2.83 g of the isomer mixture of Step B in 20 ml of methylene chloride. The mixture was stirred for 20 minutes, at −70° C. and 2 ml of water were added The mixture was stirred for 30 minutes at 20° C. followed by drying, filtering and evaporation to dryness under reduced pressure to obtain 1.95 g of the desired product (mixture of isomers 7/3).

NMR Spectrum: CDCl₃ 250 MHz 3.37, 3.38: the OCH₃'s; 3.54, 3.84, 3.97 (m): the central CH₂'s; 3.87 (s): OCH₃ (in position 3); 4.34 (d): —CH₂-OH; 6.29 (t): CH=CHCH₂; 6.93 (d): —CH=CH-CH₂; 7.19 (s): aromatic H.

STEP D:
[2-chloro-4,5-bis-[(2-methoxy-ethoxy)-methoxy]-3-methoxy] (1,2-epoxy) styrol (isomer A) and
[2-chloro-3,4-bis-[(2-methoxy-ethoxy)-methoxy]-5-methoxy](1,2-epoxy) styrol (isomer B)

A solution of 2.79 g of m-chloroperbenzoic acid in 50 ml of methylene chloride was added at +5° C. to a solution of 4.78 g of the isomer mixture of Step C in 50 ml of methylene chloride and the mixture was stirred for 16 hours at 20° C. 20 ml of a saturated solution of sodium bicarbonate and 50 ml of methylene chloride were added, followed by decanting, washing with water, drying and evaporting to dryness under reduced pressure. The residue was chromatographed on silica (eluant: methylene chloride—acetone 85-15) to obtain 2.12 g of isomer A product and 716 mg of isomer B.

NMR Spectrum: CDCl₃ 250 MHz
3.07 (t,d):

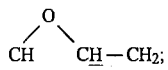

3.37, 3.38 (s): the OCH₃'s; 3.57, 3.83, 3.93 (m): the central CH₂'s; 3.88 (s): OCH₃ (in position 3); 3.83, 4.06 (ddd): —CH₂OH; 4.19 (d, J=2):

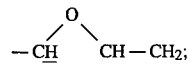

5,2, 5.26 (s): the OCH₂'s; 1.94 (d,d, J=5.5, 7.5): OH.

STEP E: Diphenylmethyl
[[2-chloro-4,5-bis-[e-methoxy-ethoxy)-methoxy]-3-methoxy]-phenyl]-chloroacetate a) Opening of the epoxide A solution prepared at +5° C. of 1,306 g of copper chloride, 20 ml of tetrahydrofuran and 1 g of lithium chloride was stirred for 5 minutes and then, 2.055 g of the isomer A epoxide of Step D dissolved in 10 ml of tetrahydrofuran were added to this solution at 20° C. The mixture was stirred for 5 hours at 20° C. and 10 ml of water were added, followed by decanting, washing, drying and evaporating to dryness under reduced pressure to obtain 2.09 g of intermediate diol.

b) Oxidation 9 ml of water and 3.79 g of sodium periodate and 50 mg of hydrated ruthenium chloride (with 35/40% Ru) were added at +5° C. to +10° C. to a solution of 2,035 g of the diol above with 6 ml of carbon tetrachloride and 6 ml of acetonitrile. The mixture was stirred for one hour at 20° C. and 20 ml of methylene chloride and 10 ml of water were added, followed by decanting, washing, drying and evaporating to dryness under reduced pressure to obtain 1.8 g of the intermediary acid.

c) Esterification 790 mg of diphenyl diazomethane were added to a solution of 1.8 g of the above product in 20 ml of methylene chloride and the mixture was stirred for one hour at 20° C. and concentrated to dryness under reduced pressure. After chromatography on silica (eluant: methylene chloride (9-1)), 1.525 g of the desired product was obtained.

NMR Spectrum CDCl₃ 250 MHz 3.34, 3.37: the OCH₃' s; 3.47, 3.57, 3.74, 3.97 (m): the central CH₂'s; 3.87 (s): 3-methoxy; 5.12, 5.24: the OCH₂'s; 5.94:

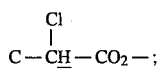

6.89 (s): CO₂-CH

STEP F: Diphenylmethyl
aminoxy-[[2-chloro-4,5-bis-[(2-methoxy-ethoxy)-methoxy] -3-methoxy]-acetate a) Phthalimidoxylation 1.48 g of the product of Step E, 7.5 ml of dimethylformamide with 363 mg of potassium acetate and 604 mg of N-hydroxyphthalimide were stirred together for 5 hours.

b) Hydrazinolysis

180 μl of hydrazine hydrate were added at 20° C. and after the mixture was stirred for 20 minutes at 20° C. the phthalylhydrazide was separated out and washed with acetonitrile. The organic fractions were evaporated to dryness to obtain after chromatography on silica (eluant: methylene chloride—ethyl acetate (3-1)), 1.11 g of the desired product.

NMR Spectrum: CDCl₃ 250 MHZ 3.33, 3.37 (s): the OCH₃'s; 3.44, 3.57, 3.71, 3.97 (m): the central CH₂'s; 3.88 (s): 3-methoxy; 5.09 and 5.23: the OCH₂'s; 5.73 (s):

5.84: NH₂; 6.91 (s); 6.94: CO₂CH-ϕ₂; 7.07 to 7.35: aromatics.

STEP G:
[[[1-[2-chloro-4,5-bis-[(2-methoxy-ethoxy)-methoxy]-3-methoxy]
-phenyl]-2-oxo-2-(diphenylmethoxy)-ethyl]-oxy]-imino]
[2-[(triphenylmethyl)-amino]-thiazol-4-yl]-acetic acid Using the procedure of Step E of Example 1, 1.1 g of the product of Step F and 835 mg of oxo-[2-[(triphenylmethyl)-amino]-thiazol-4-yl]-acetic acid (Belgian Application No. 864,828) were reacted. The product was not isolated and was used as is for the following step.

STEP H: 4-methoxy-benzyl
7δ-[[[[[1-[2-chloro-4,5-bis-[-(2-methoxy-ethoxy)-methoxy]-3-methoxy]-phenyl]-2-oxo-2-(diphenyl-methoxy)-ethoxy]-oxy]-imino]
[2-(triphenylmethyl)-amino]-thiazol-4-yl]-acetamido]
-3-[(Z)-3-chloro-1-propenyl]-8-oxo-5-thia-1-azabicyclo[4,2,0]oct-2-en-2-carboxylate Using the procedure of Step F of Example 1, the crude product of Step G and 781 mg of 4-methoxy-benzyl 7δ-amino-3[(Z)-3-chloro-1-propenyl]-8-oxo-5-thia-1-azabicyclo[4,2,0]oct-2-en-2-carboxylate hydrochloride (EP 0,333,154) were reacted to obtain after chromatography on silica, (eluant: methylene chloride—ethyl acetate (9-1)), 1.36 g of the desired product.

NMR Spectrum: CDCl₃ 300 MHz 3.25, 3.29, 3.36, 3.37, 3.81: the OCH₃'s; 3.20 to 4.0: —SCH₂—, C-CH₂Cl, the central CH₂'s; 4.94 (d) to 5.25: CO₂CHϕ₂, NH-CH-CH-S, the OCH₂O's; 5.75 (m) : —CH=CH-CH₂ (Z) ; 5.9 (m) : NH-CH-CH-S; 6.28 (d) : —CH=CH-CH₂ (ΔZ); 6.8 to 7.15: aromatics+ H₅ thiazole.

STEP I: 4-methoxy-benzyl
7δ-[[[[[1-[2-chloro-4,5-bis-[(2-methoxy-ethoxy)-methoxy] -3-methoxy]-phenyl]-2-oxo
-2-(diphenyl-methoxy)-ethyl] -oxy]-imino]
[2(triphenylmethyl)-amino]-thiazol-4-yl]-acetamido]
-3-[(Z)-3-iodo-1-propenyl]-8-oxo-5-thia-1-azabicyclo[4,2,0] oct -2-en-2-carboxylate Using the procedure of Step G of Example 1, 1.33 g of the product of Step H were reacted to obtain after chromatography on silica (eluant: methylene chloride—ethyl acetate (9-1)), 990 mg of the desired product.

NMR spectrum: CDCl₃ 400 MHz 3.24 (s); 3.26 (s); 3.35 (s); 3.36 (s): the 2 OCH₃'s; 3.2 to 4.0 (m): —SCH₂-C and the central CH₂'s; 3.8 (s,d) 3.85, 3.88 (s): the 2=C-OCH₃'s; 4.9 to 5.07 (m) 5.18 to 5.25 (m): the O-CH₃'s; 4.97, 5.02 (d): CH-CH-S—; 5.87 (ddd) NH-CH-CH-S—; 6.51, 6.53 (s): =NH-O-CH=; 6.79, 6.80 (s): H₅ thiazole; 6.84 to 7.37 (m): aromatics other CH=C and CO₂-CH-ϕ₂; 7.78, 8.3 (d)

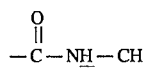

STEP J:
1-[3-7δ-[[[[[1-[2-chloro-4,5-bis-[(2-methoxy-ethoxy)-methoxy)
-3-methoxy]-phenyl]-2-oxo-2-(diphenyl-methoxy)-ethyl]-oxy]
-imino]-[2-(triphenylmethyl)-amino]-thiazol-4-yl]acetamido]
-2-[(4-methoxy-benzyloxy)-carbonyl]-8-oxo-5-thia-1-azabicyclo
[4,2,0]oct-2-en-3-yl]-2-propenyl]-imidazo(1,2-a)
pyridinium iodide Using the procedure of Step H of Example 1, 735 mg of the product of Step I and 260 microliters of imidazo(1,2-a)pyridine were reacted to obtain 750 mg of the expected product.

NMR Spectrum: CDCl₃ 300 MHz 3.14 to 3.38: —S-CH₂-C=, the

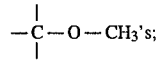

3.78, 3.79, 3.85, 3.87: =C-OCH₃; 3.3 to 4.0: the central CH₂'s; 4.9 to 5.02: NH-CH-CH-S—; 5.8 (m): =NH-CH-CH-S; 6.27 (m): —CH=CH-CH₂ (ΔE); 6.53, 6.54:

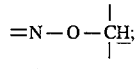

6.76 to 7.3:CO₂-CH-ϕ₂, —CH=CH-CH₂ and the aromatics; 7.6 to 91.0: imidazopyridine.

STEP K: Internal salt of (6R(3-(E) 6ᵅ, 7δ(Z)))-1-(3-(7-(((2-amino-4 -thiazolyl) (carboxy-(2-chloro-4,5-dihydroxy-3-methoxyphenyl) -methoxy)-imino)-acetamido)-2-carboxy-8-oxo-5-thia-1-azabicyclo [4,2,0]oct-2-en-3-yl]-2-propenyl]-imidazo(1,2-a]) pyridinium Using the procedure of Step I of Example 1, 750 mg of the product of Step J were reacted to obtain 463 mg of the desired product.

NMR Spectrum: DMSO 300 MHz 5.12 (d,d): =NH-CH-CH-S—; 528 to 5.3: =CH-CH-N⁺; 5.74 (m): =NH-CH-CH-S; 5.75: =N-O-CH—; 6.23 (m): =C-CH=CH—; 6.78 (s): H₅ thiazole; 6.84 (d, J= 15): =C-CH=CH— (ΔE); 7.36: NH₂; 7.58 to 8.93: imidazopyridine; 9.55: mobile H's.

EXAMPLE 41

Internal salt of (6R-(3-(E) 6α,
7δ(Z)))-1-(3-(7-(((2-amino-4thiazolyl)
(carboxy-(2-chloro-3,4-dihydroxy-5-methoxy-
phenyl)-methoxy)
-imino)-acetyl)-amino)-2-carboxy-8-oxo-5-
thia-1-azabicyclo
[4,2,0]oct-2-en-3-yl)-2-propenyl)-imidazo
(1,2-a)pyridinium Using the procedure of Steps E to K of Example 40, isomer B of Step D of Example 40 were reacted to obtain the desired product.

NMR Spectrum: DMSO 300 MHz 3.5 to 3.7 (m): S-CH$_2$-C=; 3.73, 3.74 (s): OCH$_3$; 5.18: NH-CH-CH-S; 5.29: —CH$_2$N$^+$; 5.79 (ddd): NH-CH-CH—; 5.83, 5.85 (s): =N-O-CH=; 6.25 (m): CH=CH—; 6.6 (s): 6.78 (s): 6.82 (s): aromatic, H$_5$ thiazole; 6.88 (d,d J=16): —CH=CH-CH$_2$ (ΔE); 7.58 to 8.96 96H) imidazopyridine.

EXAMPLE 42

Internal salt of (6R-(3-(E) 6α,
7δ(Z)))-1-(3-(7-(((2-amino-4-thiazolyl)
(carboxy-(2-chloro-4,5-dihydroxy-3-methoxy-
phenyl)-methoxy)
-imino)-acetamido)-2-carboxy-8-oxo-5-thia-1-
azabicyclo [4,2,0]oct-2-en-3-yl)-2-propenyl)
quinolinium

STEP A:
1-[3-[7δ-[[[[1-[2-chloro-4,5-bis-[(2-methoxy-
ethoxy)-methoxy]
-3-methoxy]-phenyl]-2-oxo-2-(diphenyl-methoxy]-
ethyl]-oxy]-imino]
[2-(triphenylmethyl)-amino]-thiazol-4-yl]-
acetamido]-2-[ (4-methoxy-benzyloxy)-carbonyl]
-8-oxo-5-thia- 1-azabicyclo [4,2,0]oct-2-en-3
-yl]-2-propenyl]quinolinium iodide Using the procedure of Step J of Example 40, 700 mg of the product of Step I of Example 40 and 282 microliters of quinoline were reacted to obtain 706 mg of the desired product.

STEP B: Internal salt of (6R-(3-(E) 6α, 7δ(Z)))-1-(3-(7-(((2-amino-4 -thiazolyl) (carboxy-(2-chloro-4,5-dihydroxy-3-methoxy-phenyl)-methyl)-imino) -acetamido)-2-carboxy-8-oxo-5-thia-1-azabicyclo [4,2,0]oct-2-en-3-yl)-2-propenyl) quinolinium Using the procedure of Step K of Example 40, 690 mg of the product of Step A were reacted to obtain 434 mg of the desired product.

NMR Spectrum: DMSO 300 MHz 3.4 to 3.8 (m): S-CH$_2$—; 3.65, 3.73 (s): =C-OCH$_3$; 5.1, 5.14 (d): —NH-CH-CH—; 5.73: —NH-CH-CH—; 5.75 (s): =N-O-CH=; 5.89 (m): —CH-CH-CH$_2$; 6.75, 6.76, 6.78, 6.79 (s) : H$_5$ thiazole, aromatic H; 6.35 (m): —CH=CH-C (ΔE); 6.97 (dl J= 16 ): —CH=CH-C (ΔE); 8.07 to 9.58 (7H) quinoline; 9.53: —NH-CH-CH—; 7.35, 9.24, 13.0: mobile H's.

EXAMPLE 43

Internal salt of (6R(3-(E) 6δ,
7δ(Z)))-1-(3-(7-(2-amino-4-thiazolyl)
(carboxy-(2-chloro-3,4-dihydroxy-5-methoxy-phenyl)-
methoxy)
-imino-acetamido]-2-carboxy-8-oxo-5-thia-1-azabicyclo
[4,2,0]oct-2-en-3-yl)-2-propenyl) quinolinium

STEP A: 1-[3-[7δ
-[[[[(1-[(2-chloro-3,4-dihydroxy-5-methoxy]-phenyl]
-2-oxo-2-(diphenylmethoxy)-ethyl]-oxy-]-imino]
[2-(triphenylmethyl)
-amino]-thiazol]-4-yl]-acetamido]-2-[(4-methoxy-
benzyloxy) -carbonyl]-8-oxo-5-thia-1-azabicyclo
[4,2,0]oct-2-en -3-yl]-2-propenyl]quinolinium
iodide Using the procedure of Step J of Example 40, 450 mg of the product of Step E of Example 41 were reacted to obtain 440 mg of the desired product.

STEP B: Internal salt of (6R-(3-(E) 6α, 7δ(Z)))-1-(3-(7-(((2-amino-4 -thiazolyl) (carboxy-(2-chloro-3,4,dihydroxy-5-methoxyphenyl) -methoxy)-imino)-acetamido)-2-carboxy-8-oxo-5-thia-1-azabicyclo [4,2,0]oct-2-en-3-yl)-2-propenyl) quinolinium Using the procedure of Step K of Example 40, 440 mg of the product of Step A were reacted to obtain 256 mg of the desired product.

NMR Spectrum: DMSO 300 MHz 3.48 to 3.84 (m): S-CH$_2$; 3.71, 3.73 (s): =C-OCH$_3$; 5.17 (d,d): —NH-CH-CH-C; 5.8 (m): —NH-CH-CH—; 5.82, 5.84 (s): N-O-CH=; 5.88 (m): —CH=CH-CH$_2$—; 6.38 (d, m): CH=CH-CH$_2$; 6.97 (d, d) (dJ=16): —CH=CH— (ΔE); 6.59 (s) : 6.77 (s) : 6.81 (s) : H$_5$ thiazole, aromatic; 8.06 to 9.58: quinoline (7H); 9.53, 9.64 (d): C-NH—; 7.54 (m): 9.25 (m): 13.70 (m): mobile H's.

EXAMPLE 44

Internal salt of (6R-(3-(E) 6α, 7δ-Z
(S*)))-1-(3-(7-(((2-amino-4-thiazolyl)
(carboxy-(3,4-dihydroxy-5-fluorophenyl)-methoxy)-
imino)-acetamido)
-2-carboxy-8-oxo-5-thia-1-azabicyclo[4,2,0]
oct-2-en-3-yl) -2-propenyl) quinolinium 10 mg of the product of Example 3 were chromatographed on a MICROBONDAPACK C$_{18}$ column (eluant: water (at pH 2.7 with trifluoroacetic acid)—acetonitrile containing 0.025% trifluoroacetic acid 86-14 to obtain 1.5 mg of the expected (S) isomer and 1.5 mg of (R) isomer.

NMR Spectrum: DMSO 400 MHz 3.40 to 3.60 (m): CH$_2$S; 5.13 (d, J= 5): H$_6$; 5.77 (dd, J = 5 and 8): H$_7$ (d, after exchange); 5.32 (s) ø-CH-O; 5.87 (m) : CH$_2$N$^+$; 6.31 (m) : CH=CH-CH$_2$; 7.00 (d, J= 16): CH=CH-CH$_2$; 6.77 (s) : H$_5$ thiazole; 6.72 (m): H$_4$', H$_6$'; 7.25 (s): mobile 2H's; 8.06 (dd, J= 7 and 8) and 8.28 (ddl) J=7 and 9): H$_6$", H$_7$"; 8.22 (dd J= 6 and 8): H$_3$"; 8.50 (d, J= 8) and 8.55 (d, J= 9): H$_4$" and H$_5$"; 9.33 (d, J= 8): H$_8$"; 9.57 (d, J= 6): H$_2$".

EXAMPLE 45

Internal salt of (6R-(3-(E) 6α, 7δ-(Z(R*)))-1-(3-(7-(((2-amino -4-thiazolyl) (carboxy-(3,4-dihydroxy-5-fluorophenyl)-methoxy)-imino) -acetamido)-2-carboxy-8-oxo-5-thia-1-azabicyclo [4,2,0]oct-2-en-3 -yl)-2-propenyl) quinolinium R isomer isolated during the chromatography in Example 44.

NMR Spectrum: DMSO 400 MHz 3.39 to 3.75 (m): $CH_2S$; 5.16 (d, J=5): $H_6$; 5.32 (s) o-CH-O; 5.74 (dd, J= 5 and 8); $H_7$; 5.88 (m): $CH_2N^+$; 6.36 (dt): $CH=CH-CH_2$; 6.99 (d, J= 16): $CH=CH-CH_2$; 6.73 (m) (3H): $H_5$ thiazole and $H_2'$ and $H_6'$; 7.26 (s): mobile 2H's; 8.07 (t, J= 8) and 8.28 (t, J= 8): $H_6''$ and $H_7''$; 8.22 (dd, J= 6 and 8): $H_3''$; 8.50 (d, J= 8) and 8.55 (d, J= 9): $H_5''$ and $H_4''$; 9.33 (d, J= 8): s; 9.59 (d, J= 6): $H_2''$; 9.59 (d, m): CONH-CH; 9.14 (s): mobile 1H.

EXAMPLE 46

Internal salt of [[6R-[3-(E) 6α, 7δ(Z)(S*)-1]]-1-[3-7-[[(2-amino-4-thiazolyl] [carboxy-(2,5,-dichloro,3,4-dihydroxy-phenyl)-methoxy] -imino]-acetamido]-2-carboxy-8-oxo-5-thia-1-azabicyclo [4,2,0]oct-2-en-3-yl]-2-propenyl]-4-(methylthio) pyridinium corresponding to resolved isomer of the compound of Example 14

NMR Spectrum: DMSO 300 MHZ 2.71 (s): ø-SMe; approx 3.57: =C-$CH_2S$; 5.15 to 5.25: $H_6$ and $N^+$-$CH_2$-CH=; approx. 5.80 (sl): O-CH-o and $H_7$; 6.25 (m): =CH-$CH_2$; approx. 6.98 (d) : =C-CH=CH; 6.81 (s) : $H_5$ thiazole; 7.00: $H_6'$; 7.32 (l) 2H: $NH_2$; 7.96, 8.70 (d): H pyridine; 9.58 (d): C-NH-CH; 9.84 (s) 9.92 (s) : the OH's; 13.28, 13.78: the other mobile H's

EXAMPLE 47

Internal salt of (6R-(3-(E) 6α, 7δ-(Z)(S*)))-1-(3-(7-(((2-amino -4-thiazolyl) (crboxy-(2,5-dichloro-3,4-dihydroxy-phenyl)-methxoy)-imino) -acetamido)-2-carboxy-8-oxo-5-thia-1-azabicyclo [4,2,0]oct-2-en-3 -yl)-2-propenyl)-imidazo(1,2-a) pyridinium NMR Spectrum DMSO 300 MHz 5.15 (d, J= 5): $H_6$; 5.29 5 (m): CH-$N^+$; 5.79 (s): O-CH-ø; 5.79 (dd, d after exchange): $H_7$; 6.24 (dt, J= 15.5 and 6.5): —CH-$CH_2$, approx. ¾ H; 6.81 (s) 6.99 (s) : $H_5$ thiazole, aromatic 1H; 6.86 (d, J= 15.5) =C-CH=CH; 7.58 (t): 8.06 (t): $H_5'$, $H_6'$; 8.20 (d): $H_7'$; 8.96 (d): $H_4'$; 8.28 (d): 8.44 (d): $H_2'$, $H_3'$; 9.56 (d): CH-NH-CO; 7.35 (m) : approx. 2H; 9.87 (sl): 1H; 9.96 (sl): 1H; mobile H.

EXAMPLE 48

Internal salt of (6R-(3-(E) 6α, 7δ-(Z)(R*)))-1-(3-(7-(((2-amino-4 -thiazolyl) (carboxy-(2,5-dichloro-3,4-dihydroxy-phenyl)-methoxy)-imino) -acetamido)-2-carboxy-8-oxo-5-thia-1-azabicyclo [4,2,0]oct-2-en-3 -yl)-2-propenyl)-imidazo[1,2-a) pyridinium NMR Spectrum: DMSO 300 MHz 5.15 (d, J= 5): $H_6$; 5.27 (m): $CH_2$-$N^+$; 5.78 (d, J= 5): $H_7$; 5.81 (s): O-CH-ø, approx. 1.7 H; 6.24 (dt, J= 16 and 6): =CH-$CH_2$, approx 0.85 H; 6.84 (s) : 6.99 (s) : approx. 1.7 H, $H_5$ and aromatic 1H; 6.85 (d, J=16): =C-CH=CH; 7.57 (dd, J= 6 and 7): $H_5'$; 8.05 (dd, J= 7 and 8.5): $H_6'$; 8.17 (d, J=8.5): $H_7'$; 8.94 (d, J= 6): $H_4'$; 8.26 (d, J=2): 8.42 (d, J=2): $H_2'$, $H_3'$.

Using the procedure described in the previous examples and starting with appropriate intermediates the following products were obtained:

EXAMPLE 49

Internal salt of (6R-(3-(E) 6α, 7δ-(Z)))-1-(3-(7-(((2-amino-4-thiazolyl) (carboxy-(2,3-dihydroxy-4-methoxy-phenyl)-methoxy)-imino)--acetamido)-2 -carboxy-8-oxo-5-thia-1-azabicyclo[4,2,0]oct-2-en-3 -yl]-2-propenyl) quinolinum NMR Spectrum DMSO 300 MHz 3.52 (d) 3.70: $CH_2S$; 3.72, 3.74: C-OMe; 5.15 (d, resolved): $H_6$; 5.57 (dd) 5.80 (m): $H_7$; 5.83, 5.87:

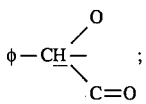

5.70 to 6.0: $CH_2$-$N^+$; 6.42 (d, resolved): 6.75 (d, resolved) aromatic H; 6.40 (m) 6.99 (d, resolved, J approx. 16): ethylene (ΔE); 6.78, 6.82: $H_5$ thiazole; 8.07 (t) : 8 26: a$H_3'$, $H_6'$, $H_7'$; 8.53 (d): 8.56 (d): 9.34 (d): $H_4'$, $H_5'$; 9.53 (d): $H_8'$; 9.45 (d): 9.56 (d):

7.45 and 8.84: mobile H.

EXAMPLE 50

Internal salt of (6R-(3-(E) 6α, 7δ-(Z)))-7-(3-(7-(((2-amino-4 -thiazolyl) (carboxy-(2,3-dihydroxy-4-methoxy-phenyl)-methoxy)-imino) -acetamido)-2-carboxy-8-oxo-5-thia-1-azabicyclo [4,2,0]oct-2-en-3 -yl)-2-propenyl)-thieno (2,3-b) pyridinium NMR Spectrum: DMSO 400 MHz 3.54 (d) approx. 3.68 (d): =C-$CH_2S$; 5.18 (m): the $H_6$'s; 5.76 (m): 5.96 (m): $H_7$; 5.72 (s): 5.74 (s): the ø-OMe's; 5.67 (m): $CH_2$-CH=; 5.83 (s): 5.87 (s): C-CH-ø; approx. 6.8 (s) resolved: the H thiazoles; 6.42 (m): 6.73 (m): $H_5$, $H_6$; 6.30 (m): 7.15 (d) resolved: =C-CH=CH-CH (ΔE) ; 7.88 (d) : $H_3'$; 8.29 (d): $H_2'$; 8.15 (m): $H_5'$; 9.08 (d): $H_4'$; 9.22 (d): $H_6'$; 9.44 (d): 9.53 (d): =C-NH-CH; 7.44 (m): 8.60 to 8.90: mobile $H_s$.

EXAMPLE 51

Internal salt of (6R-(3-(E) 6α, 7δ-(Z)))-1-(3-(7-(((2-amino-4-thiazolyl) (carboxy-(2,3-dihydroxy-4-methoxy-phenyl)-methoxy)-imino) -acetamido)-2-carboxy-8-oxo-5-thia-1-azabicyclo [4,2,0]oct-2-en-3 -yl)-2-propenyl)-imidazo (1,2-a) pyridinium NMR Spectrum: DMSO 300 MHz 7.35 (m): 8.69 (m): 8.82 (m): mobile H's; 3.52 (m) approx. 3.70 (m): $CH_2S$; 3.74 (s) : 3.75 (s): $CH_3O$-ø; 5.15 (d, resolved): $H_6$; 5.74 (dd, d after exchange): 5.81 (dd, d after exchange): $H_7$; 5.29 (m) : $CH_2$-$N^+$: 5.83 (s): 5.86 (s): O-CH-ø; 6.25 (m): 6.90 (d, resolved): CH=CH-$CH_2$; 6.43 (d) : $H_6'$; 6.72 to 6.80 (m): $H_5'$ and $H_5$ thiazole; 7.58 (t): $H_{5''}$; 8.06 (t): $H_6''$; 8.21 (d): 8.96 (d): $H_4''$, $H_7''$; 8.29 (sl): $H_3''$; 8.44 (sl): $H_2''$; 9.44 (d): 9.54 (d): CO-NH-CH.

EXAMPLE 52

Internal salt of (6R,(3-(E) 6α, 7δ-(Z)))-1-(3,(7-(((2-amino-4-thiazolyl) (carboxy-(2,3,4-trihydroxy-phenyl)-methoxy)-imino)-acetamido) -2-carboxy-8-oxo-5-thia-1-azabicyclo[4,2,0] oct-2-en-3-yl) -2-propenyl)-imidazol (1,2-a) pyridinium NMR Spectrum: DMSO 300 MHz 3.54 (m) : $CH_2$S; 5.15 (d) : $H_6$; 5.82 (m) : $H_7$ and O-CH-ø; 5.28 (m): =CH-$CH_2$-$N^+$; 6.26 (m) : CH=; 6.5 to 7.4 (m) : aromatic 6H; 7.58 (t): $H_5'$; 8.06 (t): $H_6'$; 8.20 (d): 8.96 (d): $H_4'$, $H_7'$; 8.29 (sl): 8.44 (sl): $H_2'$, $H_3'$; 9.41 (d): 9.53 (d): CO-NH-CH; 8.68 (m): 9.27 (m): 7.36 (m): mobile H's.

EXAMPLE 53

Internal salt of (6R-(3-(E) 6α, 7δ(Z)))-1-(3-(7-(((2-amino-4-thiazolyl) (carboxy-(2,3-difluoro-4,5-dihydroxy-phenyl)-methoxy)-imino)-acetamido)-2-carboxy-8-oxo-5-thia-1-azabicyclo [4,2,0]oct-2-en-3 -yl)-2-propenyl]-imidazo (1,2-a) pyridinium NMR Spectrum: DMSO 300 MHz approx. 3.70: $CH_2$S; 5.09 (d): 5.14 (d): $H_6$; 5.29 (m): $CH_2$-$N^+$; 5.58 (s): 5.59 (s): O-CH-o; 5.72 (m): $H_7$; 6.22 (m): CH=CH-$CH_2$; 6.68 (m): $H_6'$; 6.77 (s): 6.789 (s): $H_5$ thiazole; 6.85 (d, J= 16): =C-CH=CH; 7.58 (t): 8.06 (t): $H_5''$, $H_6''$; 8.19 (d): 8.96 (d): $J_4''$, $H_7''$; 8.28 (m): 8.44 (sl): $H_2''$, $H_3''$; 7.32 (m): 9.5 to 9.9 (m): mobile H's.

EXAMPLE 54

Internal salt of (6R-(3(E) 6α, 7δ(Z)))-1-(3-(7-(((2-amino-4-thiazolyl) (carboxy-2,3-difluoro-4,5-dihydroxy-phenyl)-methoxy)-imino)-acetamido)-2-carboxy-8-oxo-5-thia-1-azabicyclo[4,2,0]oct-2-en-3 -yl)-2-propenyl) quinolinium NMR Spectrum: DMSO 300 MHz 3.45 (m): L $CH_2$S; 5.09 (d) 5.14 (d): $H_6$; 5.72 (m): $H_7$; 5.58 (s): 5.59 (s): O-CHCO; 5.88 (m): CH-$N^+$; 6.34 (m): CH=CH-$CH_2$; 6.94 (d, J = 16): 6.97 (d, J= 16): CH=CH-$CH_2$; 6.67 (m): $H_6''$; 6.76 (s): 6.77 (s): $H_5$ thiazole; 8.07 (m): 8.26 (m): 8.53 (m): 9.34 (d): 9.57 (d): quinoline; 7.32 (m): 9.5 to 9.9 (m): mobile H's.

EXAMPLE 55

Internal salt of (6R-(3-(E) 6α, 7δ(Z)))-1-(3-(7-(((2-amino-4-thiazolyl) (carboxy-(2,5-difluoro-3,4-dihydroxy-phenyl)-methoxy)-imino)-acetamido)-2-carboxy-8-oxo-5-thia-1-azabicyclo[4,2,0]oct-2-3 -yl )-2-propenyl) pyridinium NMR Spectrum: DMSO 300 MHz 3.58 (m): $CH_2$S; 5.18 (d,d): $H_6$; 5.79 (m): $H_7$; 5.41 (sl): $CH_2N^+$; 5.64 (s): 5.65 (s): O-CH-C=; 6.30 (m): CH=CH-$CH_2$; 7.02 (dd, J=16): CH=CH-$CH_2$; 6.70 (dd): $H_6'$; 6.78 (s): 6.80 (s): $H_5$ thiazole; 8.18 (m) $H_3''$, $H_5''$; 8.63 (m) : $H_4''$; 9.05 (d) : $H_2''$, $H_6''$; 9.35 (d): 9.62 (d): CO-NHCH; 7.33 (m): 9.80 (m): mobile H.

EXAMPLE 56

Internal salt of (6R-3-(E) 6α, 7δ(Z)))-1-(3-(7-(((2amino-4-thiazolyl) (carboxy-(2,5-difluoro-3,4-dihydroxy-phenyl)-methoxy)-imino)-acetamido)-2-carboxy-8-oxo-5-thia-1-azabicyclo [4,2,0]oct-2-en-3 -yl)-2-propenyl)-6,7-dihydro-5H-pyrindinium NMR Spectrum: DMSO (300 MHz)

2.24 (m): $CH_2$ in position 6'; 3.14 (m)—3.37 (m): $CH_2$ in position 5' and 7'; 3.56 (m): $CH_2$S; 5.15 (d)—5.18 (d): $H_6$; 5.79 (m): $H_7$: 5.33 (d) : =CH-$CH_2$-$N^+$; 5.63 (s)—5.65 (s): O-CH-ø; 6.23 (m): CH=CH-$CH_2$; 6.85 (d)—6.88 (d, J=16): CH=CH-$CH_2$; 6.71 (dd, J=10.5 and 6) : $H_6''$; 6.78 (s)—6.81 (s): $H_5$ thiazole; 7.91 (m) : $H_3'$; 8.43 (d, J=8): $H_4'$; 8.76 (d, J=6): $H_2'$; 9.54 (d)—9.63 (d): CH-NH-CO; 7.35 (m)—9.85 (m) : mobile H's.

EXAMPLE 57

Internal salt of (6R -(3(E) 6α, 7δ(Z)))-1(3-(7-(((2-amino-4-thiazolyl) (carboxy-(2,5-difluoro-3-4-dihydroxy-phenyl)-methoxy)-imino)-acetamido)-2-carboxy-8-oxo-5-thia-1-azabicyclo [4,2,0]oct-2-en-3 -yl)-2-propenyl) qinolinium NMR Spectrum: DMSO (300 MHz)

3.4 to 3.7 (m) : $CH_2$S; 5.15 (dd): $H_6$; 5.79 (m): $H_7$; 5.62 (s)— 5.64(s): —O-CH-ø; 5.89 (m): =CH-$CH_2$-$N^+$; 6.37 (m): CH=CH-$CH_2$; 6.97 (dd, J=15.5): CH=CH-$CH_2$; 6.76 (s)—6.80 (s): $H_5$ thiazole; 6.70 (dd, J=11 and 6): $H_6''$; 8.07 (m)—8.27 (m)—8.53 (m)—9.34 (d): quinoline; 9.58 (d) : $H_2$; 9.53 (d)—9.62 (d) : CO-NH-CH; 7.30 (m)—9.83 (m) : mobile H.

EXAMPLE 58

Internal salt of (6R-(3-(E) 6α, 7δ(Z)))-3-(3-(7-(((2-amino-4 -thiazolyl) (carboxy-2,5-difluoro-3,4-dihydroxy-phenyl)-methoxy) -imino)-acetamido)-2-carboxy-8-oxo-5-thia-1-azabicyclo [4,2,0]oct-2-en-3-yl)-2-propenal) thiazolium Spectrum: DMSO (300 MHz)

3.50 to 3,75 (m): $CH_2$S; 5.16 to 5.19 (d): $H_6$; 5.81 (m): $H_7$; 5.33 (m): =CH-$CH_2$-$N^+$; 5.63 (s) —5.65 (s): O-CH-ø; 6.26 (m) CH=CH-$CH_2$; 6.71 (dd, J=6 and 11): $H_6''$; 6.78 (s) —6.81 (s): $H_5$ thiazole; 8.37 (m) —8.51 (m): $H_4'$, $H_5'$; 10.20 (sl): $H_2'$; 7.30 (m): 9.5 to 9.9 (m) —13.25 (m) —13.75 (m): mobile H's.

EXAMPLE 59

Internal salt of (6R-(3-(E) 6α, 7δ(Z)))-2-(3-(7-(((2-amino-4-thiazolyl) (carboxy-(2,5-difluoro-3,4-dihydroxy-phenyl)-methoxy)-imino)-acetamido)-2-carboxy-8-oxo-5-thia-1-azabicyclo[4,2,0]oct-2-en-3 -yl )-2-propenyl) isoquinolinium NMR Spectrum: DMSO (300 MHz) 3.50 to 3.75 (m): $CH_2$S; 5.18 (dd): $H_6$; 5.80 (m) $H_7$; 5.53 (d): =CH-$CH_2$-$N^+$; 5.63 (s)—5.65 (s) : O-CH-ø; 6.37 (m) : CH=CH-$CH_2$; 7.09 (dd, J=15.5) : CH=CH-$CH_2$; 6.71 (dd, J-11 and 6) : $H_6''$;

6.78 (s)— 6.80 (s) : $H_5$ thiazole; 8.09 (t)—8.28 (t) : $H_6'$, $H_7'$; 8.37 (d)— 8.53 (d) : $H_5'$, $H_8'$; 8.61 (d)—8.74 (d): $H_3'$, $H_4''$; 10.06 (s): $H_1'$; 7.35 (m)—9.84 (m): mobile H's; 9.56 (d)—9.65 (d): CH-NH-CO.

EXAMPLE 60

Internal salt of (6R-(3-(E) 6α, 7δ-(Z))) 1-(3-(7-(((2-amino 4-thiazolyl) (carboxy (2,5-difluoro 3,4-dihydroxy phenyl) methoxy) imino) acetamido) 2-carboxy 8-oxo 5-thia 1-azabicyclo [4,2,0]oct-2-en-3 -yl) 2-propenyl) 4-(methylthio) pyridinium NMR Spectrum: (DMSO) 300 MHz 2,71 (s): ΦSMe; 3,54 (d), 3,66 (d); CH-S; 5,17 (m): les $H_6$; 5,22 (s,l) : =CH-CH$_2$-N$^+$; 5,63 (s) resolved: OCH-ø; 5,79 (m) : les $H_7$; 6,26 (m) CH=CH-CH$_2$ ΔE; 6,98 (d,J=16) resolved: CH=CH-CH$_2$; 6,71 (dd, J=6 et 11) : H difluorophenyl; 6,78 (s) resolved: $H_5$ thiazole; 7,30 (s,l): NH$_2$; 7,95 (d), 8,70 (d): methylthiopyridinium; 9,62–9,67 (d), 9,85: H mobile; 19,49.

EXAMPLE 61

Internal salt of (6R-(3-(E) 6α, 7δ-(Z)))4-(3-(7-(((2-amino 4-thiazolyl) (carboxy (2,5-difluoro 3,4-dihydroxy phenyl) methoxy) imino) acetamido) 2-carboxy 8-oxo 1-azabicyclo 5-thia 1-azabicyclo [4,2,0]oct-2-en-3-yl) 2-propenyl) 2-amino thiazolo (5,4-b) -pyridinium NMR Spectrum: (DMSO) 300 MHz ~3,60: CH$_2$S; 5,19 (d) resolved: $H_6$; 5,81 (d) : $H_7$; 5,47 (d) : =CH-CH$_2$-N$^+$; 5,63 (s) : O-CH-Φ; 6,21 (m) CH=CH-CH$_2$, 7,08 (d) resolved J=16: CH=CH-CH$_2$; 6,78 (S) : $H_5$ thiazole; 6,70 (dd, J=6 et 11) : $H_6''$; 7,83 (m) : $H_5'$; 8,29 CH-NH-CO; 8,73 (s), 9,84 (m), 7,33 (m) : H mobile.

EXAMPLE 62

Internal salt of (6R-(3-(E) 6α, 7δ-(Z)))7-(3-(7-(((2-amino 4-thiazolyl) (carboxy (2,5-difluoro 3,4-dihydroxy phenyl) methoxy) imino) acetamido) 2-carboxy 8-oxo 5-thia 1-azabicyclo[4,2,0]oct-2-en-3 -yl) 2-propenyl)thieno (2,3,-b)-pyridinium NMR Spectrum: (DMSO)

3,4 to 3,8: CH$_2$S; 5,18 (d, resolved) : $H_6$; 5,81 (dd, resolved) : $H_7$; 5,66 (m) 3H =CH-CH$_2$-N$^+$et O-CH-Φ; 6,30 (m) CH=CH-CH$_2$, 7,14 (d, resolved, J=16 : CH=CH-CH$_2$; 6,70 (dd, J=6 et 11) : $H_6''$; 6,77 (s), 6,81 (s) : $H_5$ thiazole; 7,89 (d J=6): $H_3'$; 8,28 (d, J=6) : $H_2'$; 8,16 (m) : $H_5'$; 9,09 (d, J=8) : $H_4'$; 9,23 (d, J=6) : $H_6'$; 9,35 (d), 9,65 (d) : CO-NH-CH; 7,32 (m), 9,83 (m) : H mobile.

EXAMPLE 63

Internal salt of (6R-(3-(E) 6α, 7δ-(Z)))7-(3-(7-(((2-amino 4-thiazolyl) (carboxy (3,4 -dihydroxy 2,5-difluorophenyl) methoxy) imino) acetamido) 2-carboxy 8-oxo 5-thia 1-azabicyclo[4,2,0]oct-2-en-3 -yl) 2-propenyl) imidazo (2,1-b)-thiazolium

EXAMPLE 64

Internal salt of (6R-(3-(E) 6α, 7δ-(Z)))3-(3-(7-(((2-amino 4-thiazolyl) (carboxy (3,4-dihydroxy 2,5-difluorophenyl) methoxy) imino) acetamido) 2-carboxy 8-oxo 5-thia 1-azabicyclo[4,2,0]oct-2-en-3 -yl) 2-propenyl) 1-methyl 1H-benzimidazolium

EXAMPLE 65

Internal salt of (6R-(3-(E) 6α, 7δ-(Z)))7-(3-(7-(((2-amino 4-thiazolyl) (carboxy (3,4-dihydroxy 2,5-difluorophenyl) methoxy) imino) acetamido) 2-carboxy 8-oxo 5-thia 1-azabicyclo[4,2,0]oct-2-en-3 -yl) 2-propenyl) 4-methylthieno (2,3-b)-pyridinium In addition to the compounds described above, the following products constitute compounds which can be obtained by the methods of the invention.

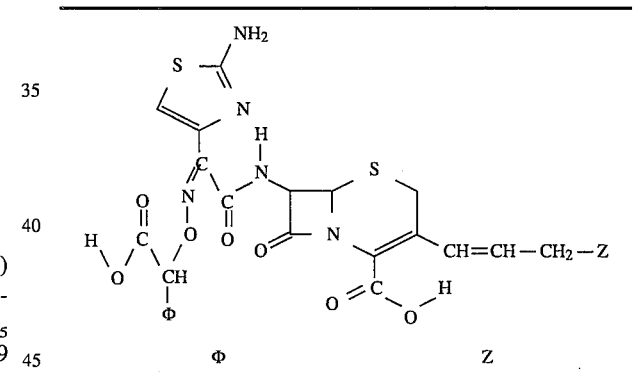

| Φ | Z |

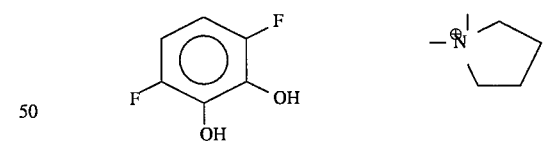

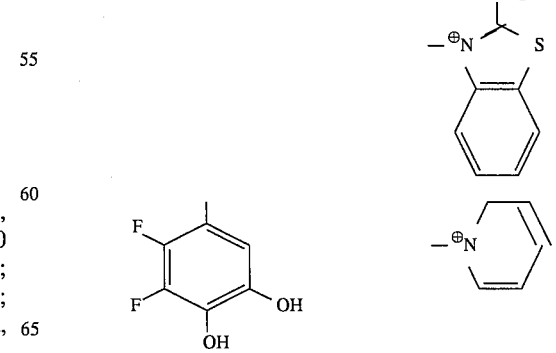

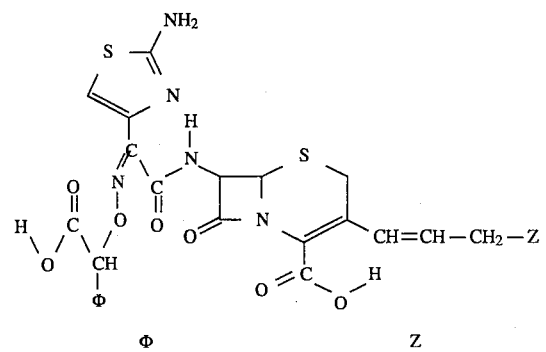
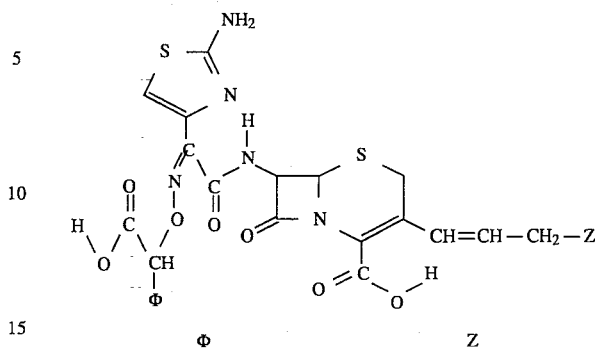
| Φ | Z |
|---|---|
| 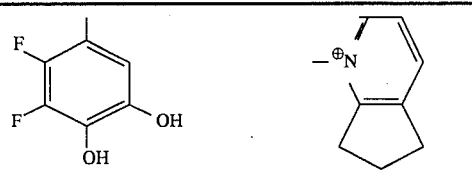 |  |
| " | 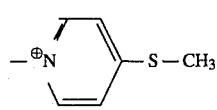 |
| " | 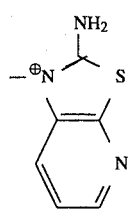 |
| 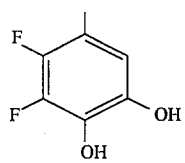 | 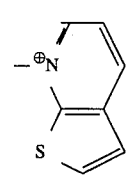 |
| " | 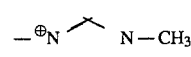 |
| " | 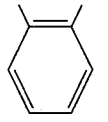 |
| " | 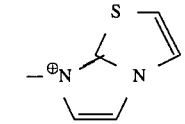 |
| " | 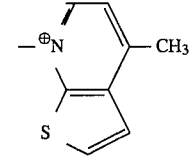 |
| Φ | Z |
|---|---|
| " | 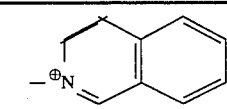 |
| 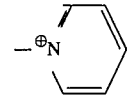 | 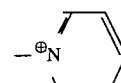 |
| " | 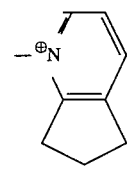 |
| " | 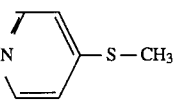 |
| " | 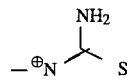 |
| " | 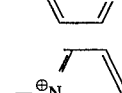 |
| " | 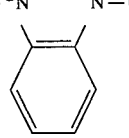 |

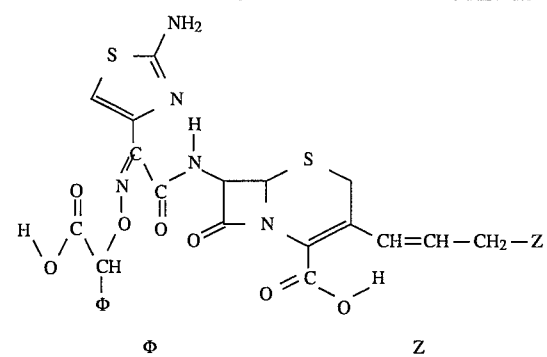
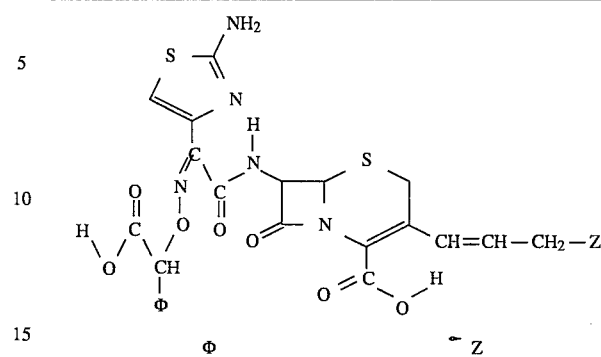

-continued
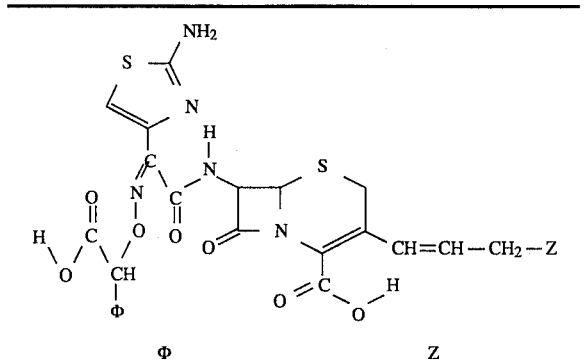
| Φ | Z |
|---|---|
| " | 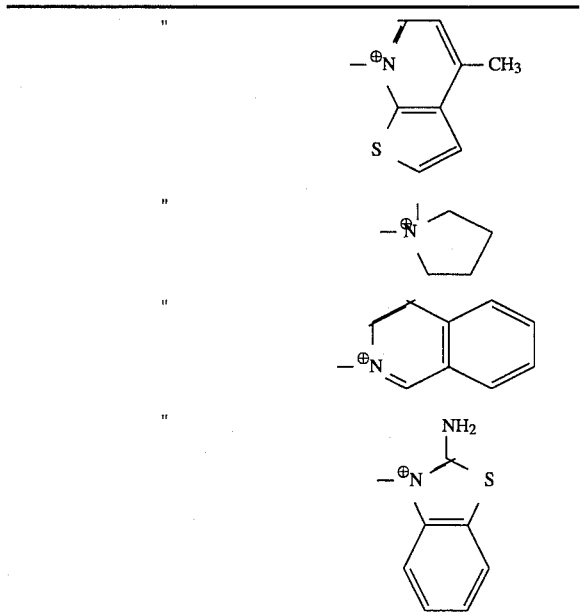 |
| 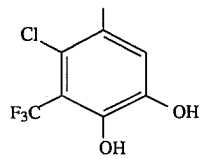 | |
| " | |
| " | |
| " | |
-continued
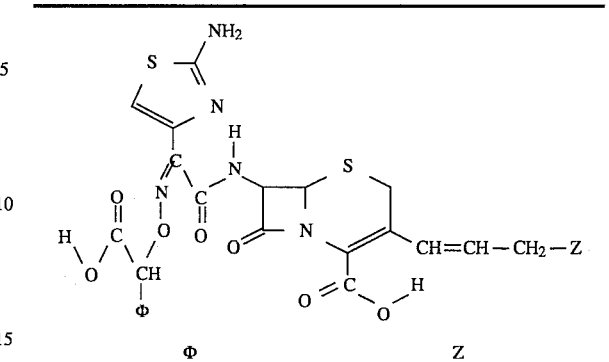
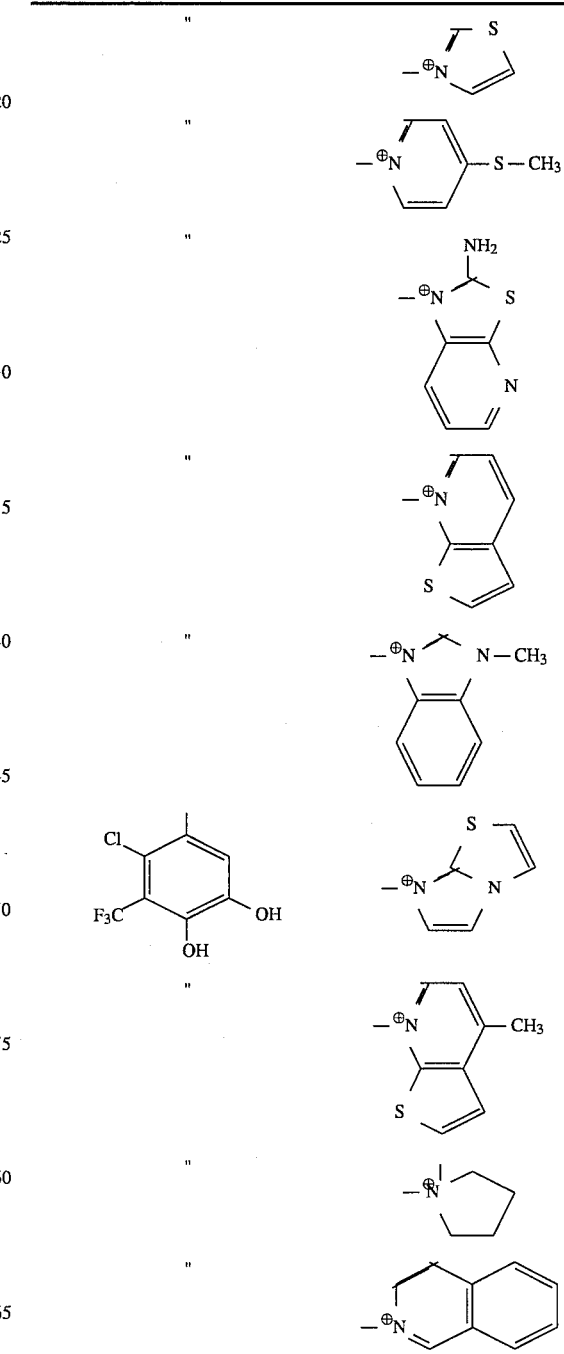

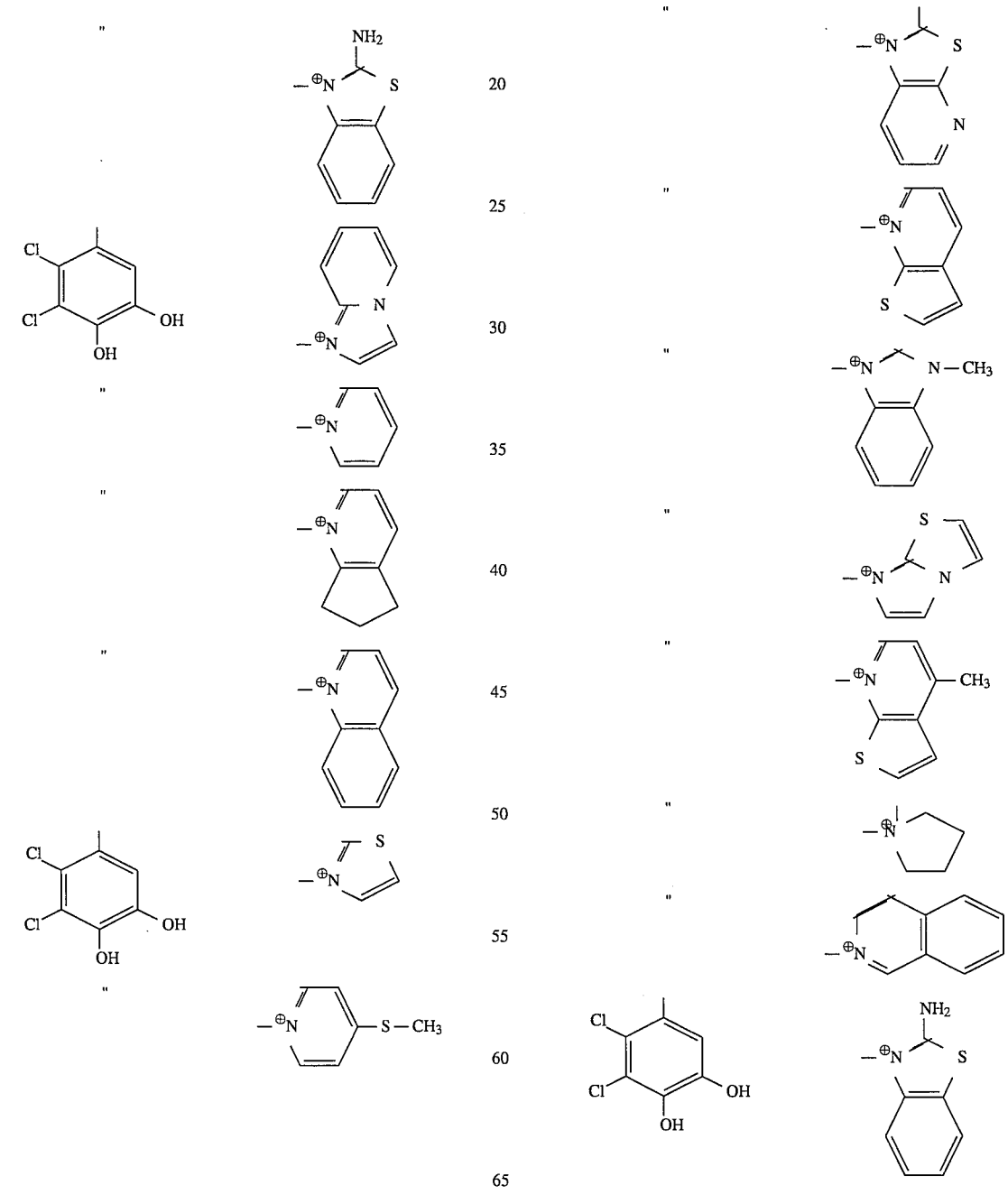

-continued
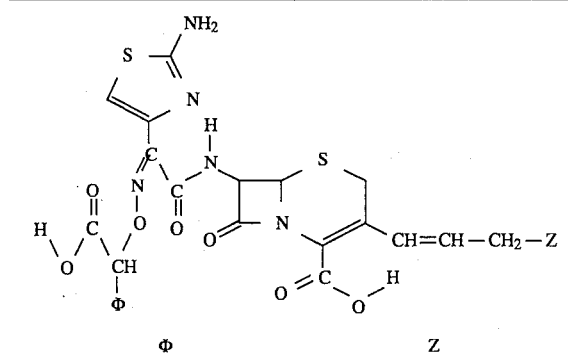
| Φ | Z |
|---|---|
| 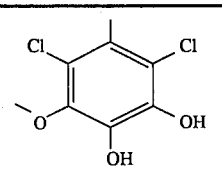 | 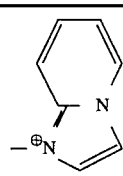 |
| " | 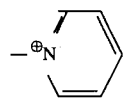 |
| " | 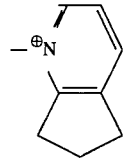 |
| " | 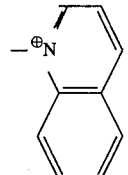 |
| " | 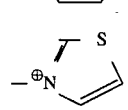 |
| " | 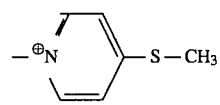 |
| " | 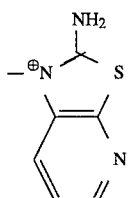 |
| 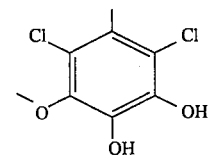 | 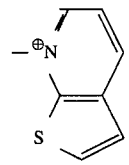 |
-continued
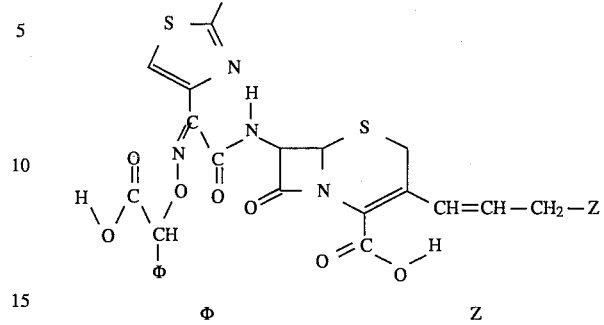
| Φ | Z |
|---|---|
| " | 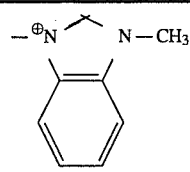 |
| " | 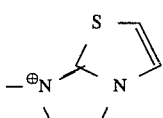 |
| " | 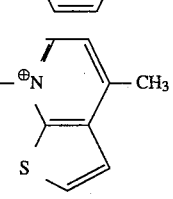 |
| " | 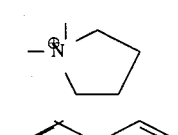 |
| " | 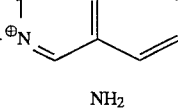 |
| " | 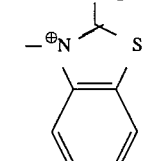 |
| 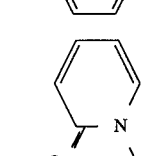 | 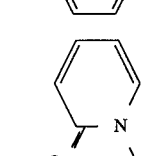 |
| 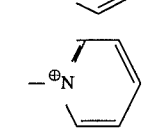 | 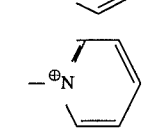 |

-continued
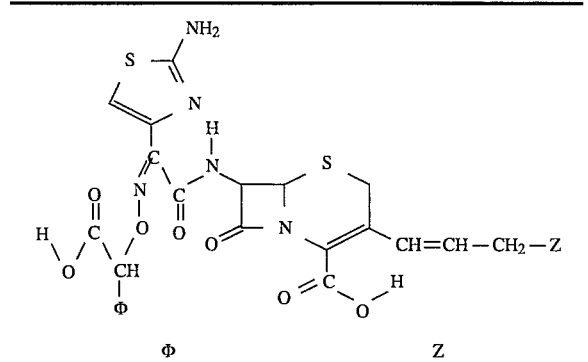
| Φ | Z |
|---|---|
| " | 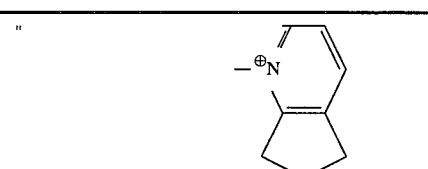 |
| " | 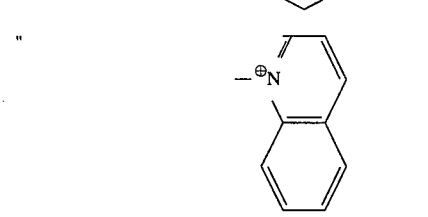 |
| " | 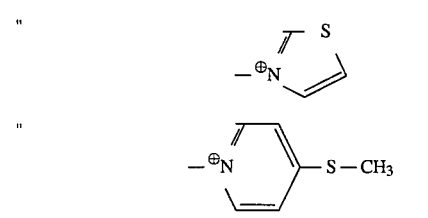 |
| " | 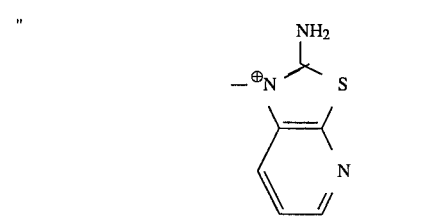 |
| " | 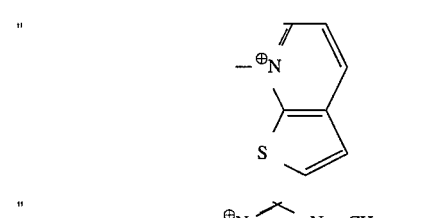 |
| " | 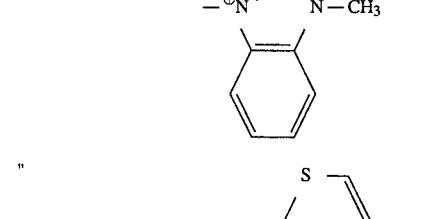 |
| " | 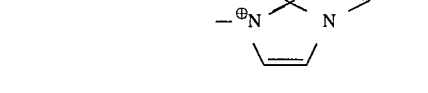 |
-continued
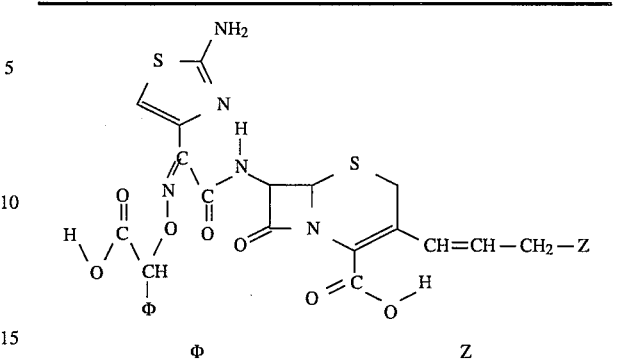
| Φ | Z |
|---|---|
| 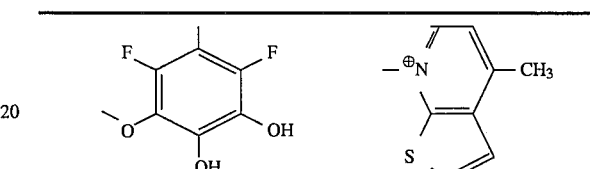 | 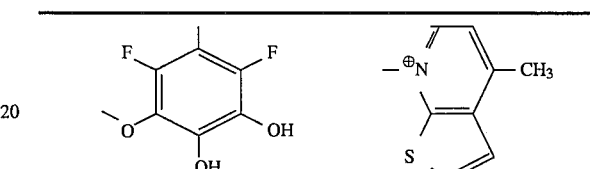 |
| " | 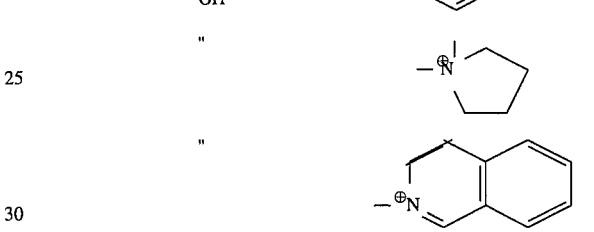 |
| " |  |
| " | 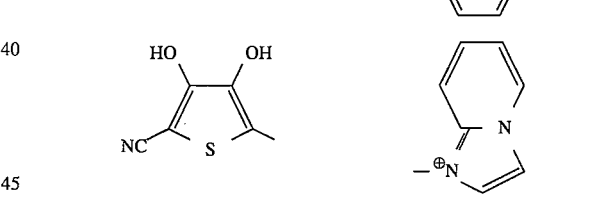 |
| 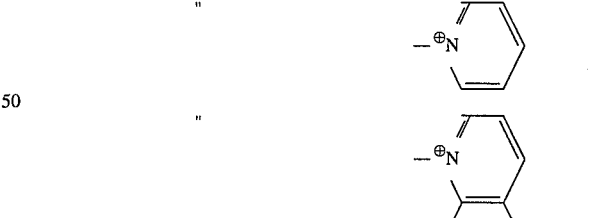 | 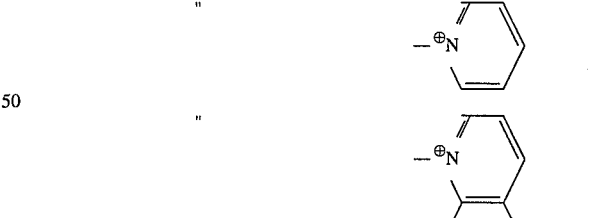 |
| " |  |
| " |  |

-continued
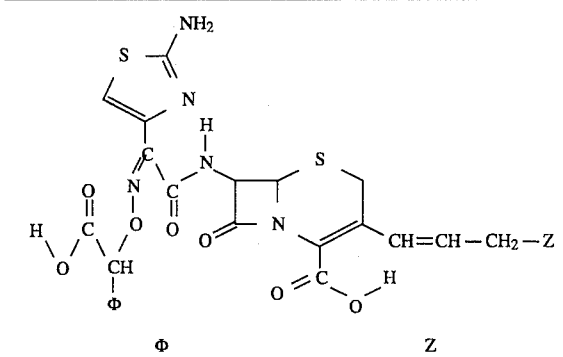
| Φ | Z |
|---|---|
| 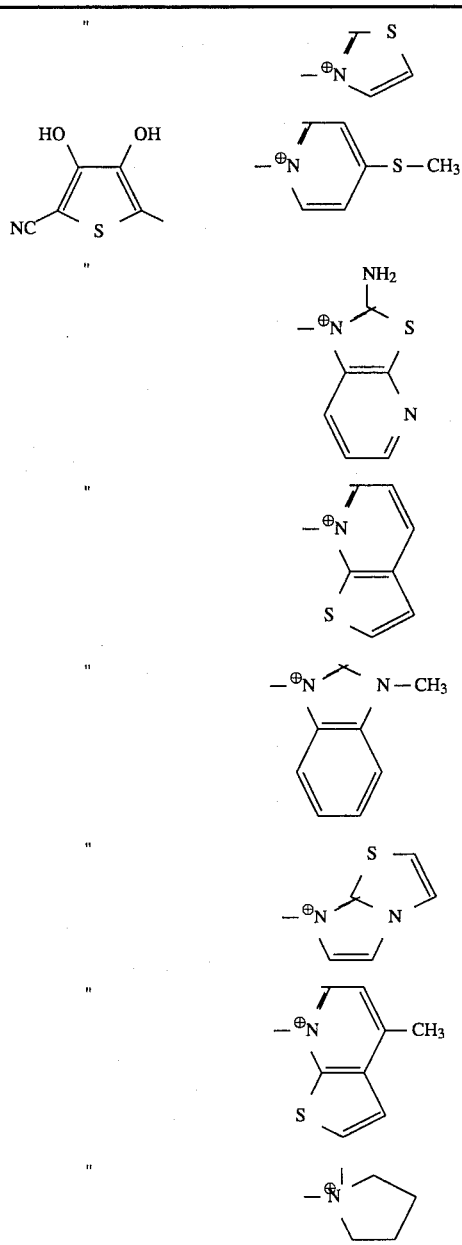 | (multiple Z groups shown) |
-continued
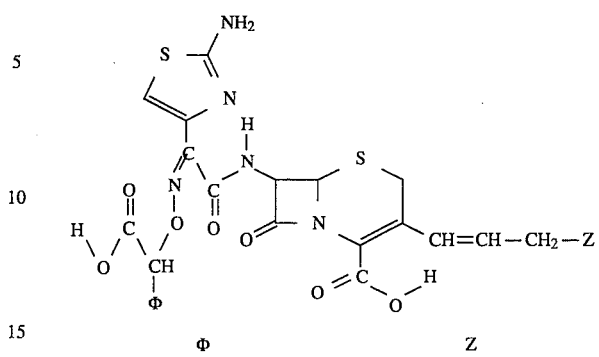
| Φ | Z |
|---|---|
| 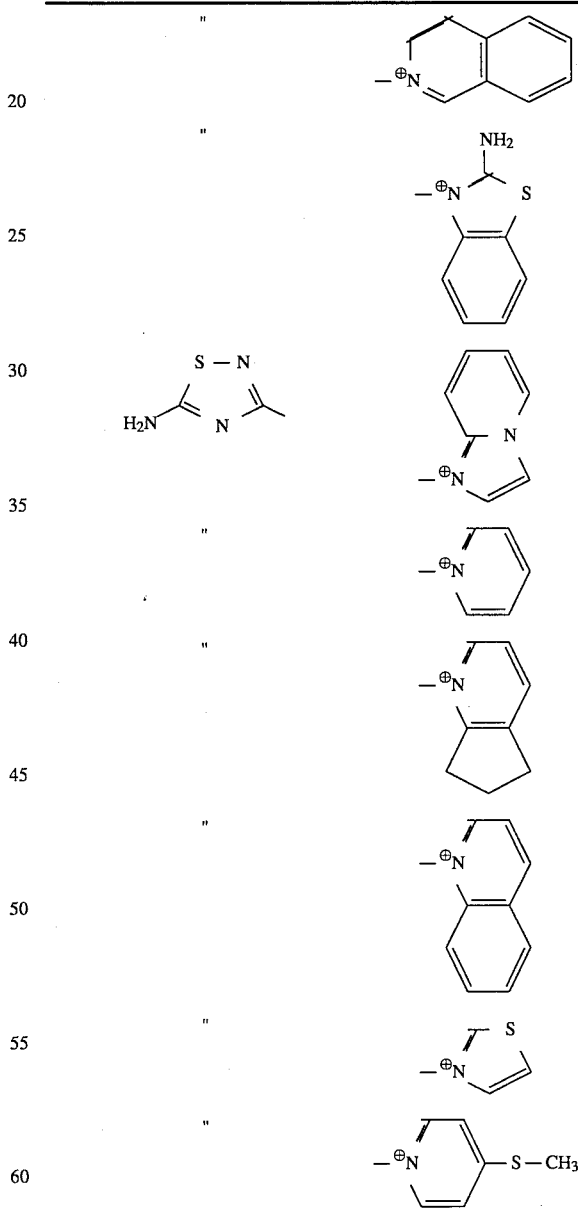 | (multiple Z groups shown) |

-continued
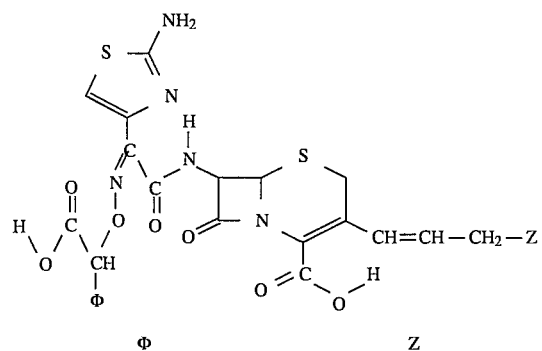
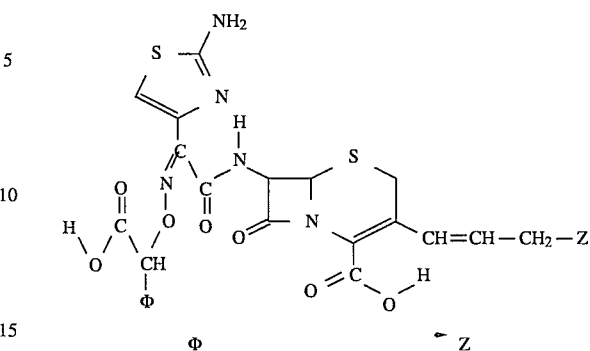
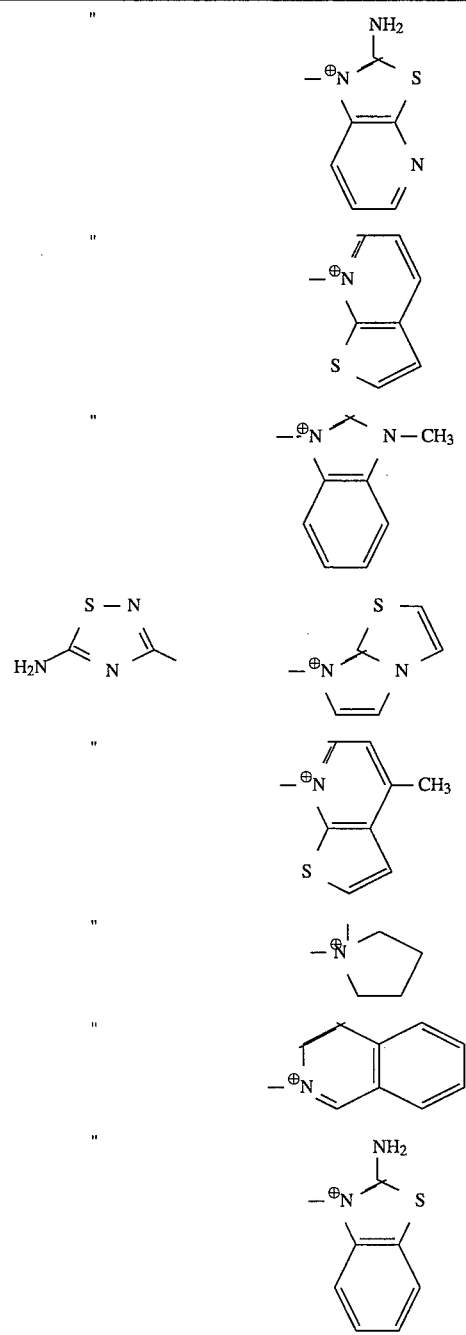

-continued
| 101 | |
|---|---|
| 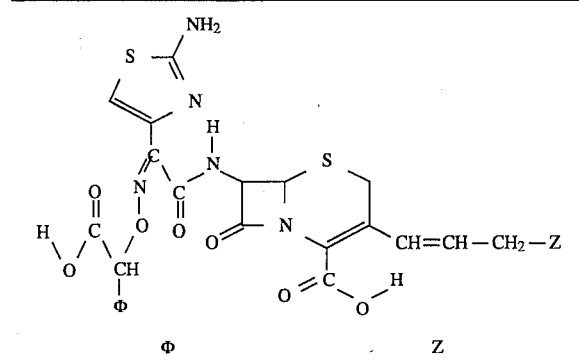 | |
| Φ | Z |
| " | 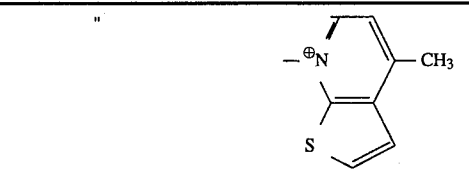 |
| " | 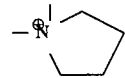 |
| " | 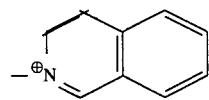 |
| " | 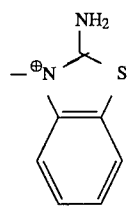 |
| 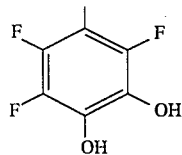 | 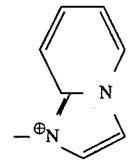 |
| 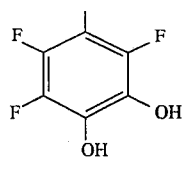 | 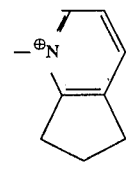 |
| " | 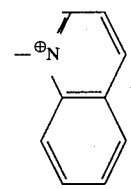 |
-continued
| 102 | |
|---|---|
| 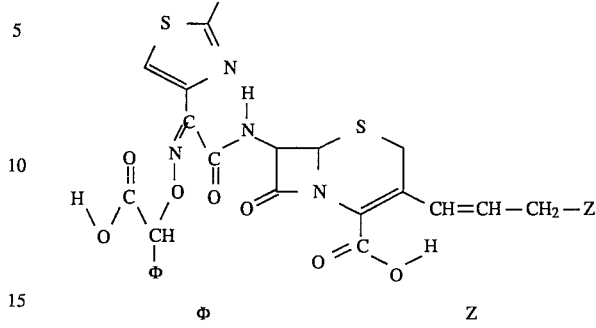 | |
| Φ | Z |
| " | 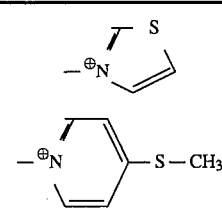 |
| " | 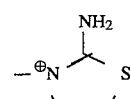 |
| " | 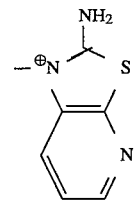 |
| " | 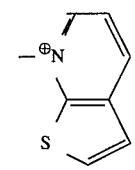 |
| " | 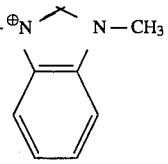 |
| " | 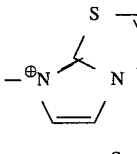 |
| 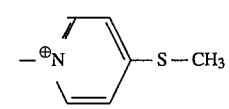 | |

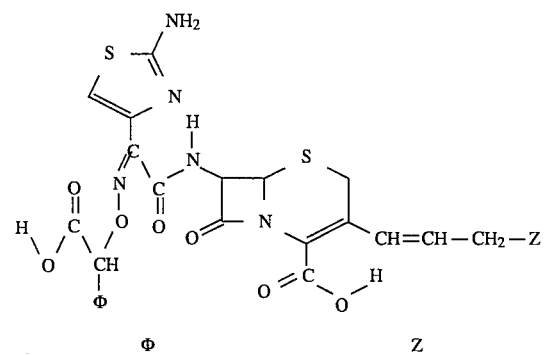
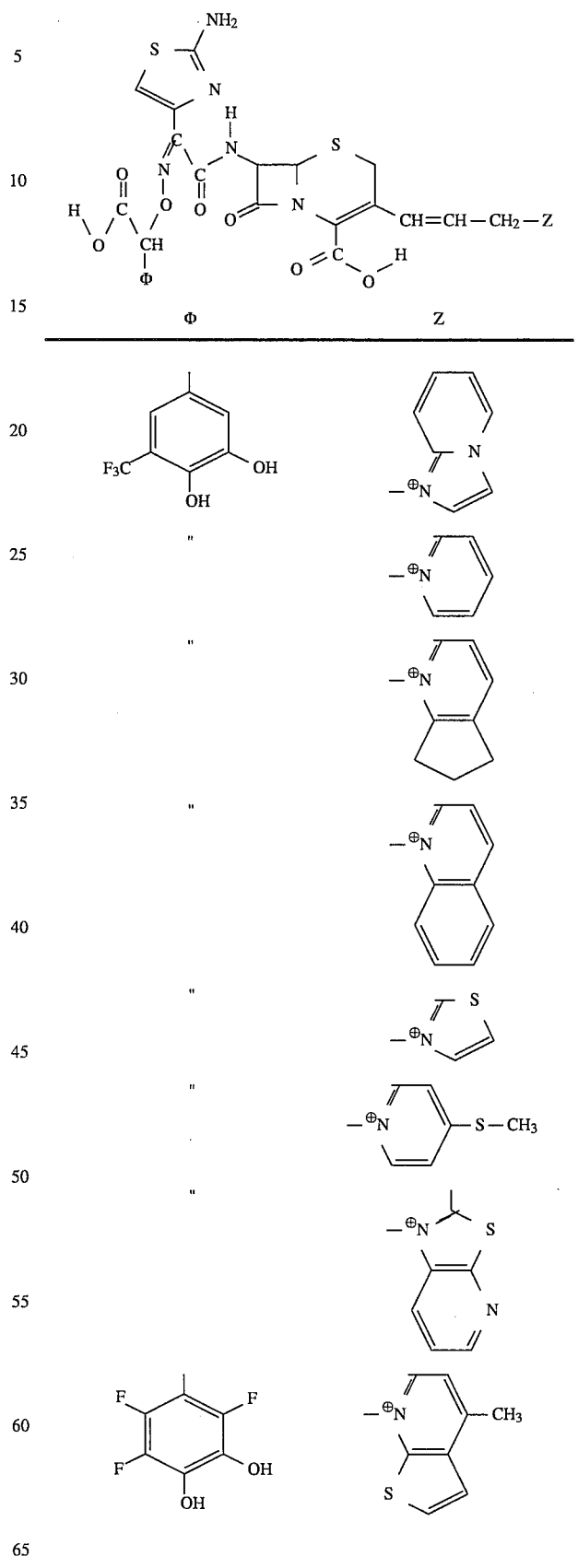

-continued

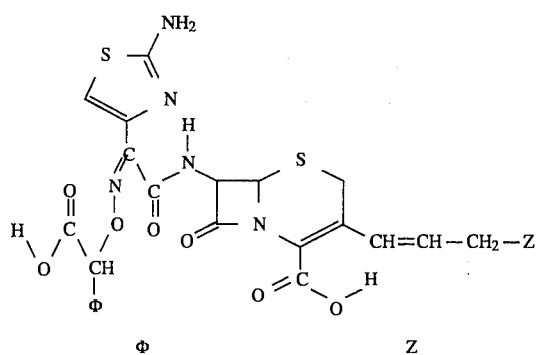

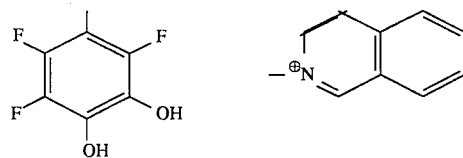

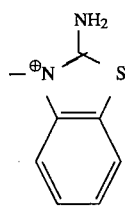

EXAMPLE 66

The following preparations for injections were made:
—containing 500 mg of the product of Example 2
—and sufficient sterile aqueous excipient for 5 ml

PHARMACOLOGICAL STUDY

In vitro activity, method of dilutions in liquid medium.

A series of tubes was prepared in which an equal amount of sterile nutritional medium was distributed and increasing amounts of the test product was distributed into each tube. Then, each tube was seeded with a bacterial strain and after incubation in an oven for twenty four hours at 37° C. The growth inhibition was evaluated by transillumination which allowed the minimal inhibiting concentrations (M.I.C.) to be determined, expressed in ug/ml (TABLE I).

In vitro activity, method of dilutions in solid medium.

A series of dishes was prepared in which an equal amount of sterile nutritional medium was distributed containing increasing amounts of the test product. Then, each dish was seeded with several bacterial strains and after incubation in an oven for 24 hours at 37° C., the growth inhibition was evaluated by the absence of any bacterial development, which allowed the minimal inhibiting concentrations (M.I.C.) to be determined expressed in micrograms/ml.

The results were expressed in M.I.C. 90 which is the minimum concentration of antibiotic allowing the growth of the strains studied to be inhibited by 90° (TABLE II).

TABLE II

| $MIC_{90}$ Product of example | oracillin-sensitive penicillin-resistants *Staphylococci aureus* (20 strains) | Enterobacteria producing cephalosporinases (20 strains) | Enterobacteria producting β lactamase with enlarged spectrum (16 strains) | *Pseudomonas Aeruginosa* (39 strains) |
|---|---|---|---|---|
| 39 | 2, 5 | 0, 3 | 2, 5 | 0, 08 |
| 43 | 0, 3 | 2, 5 | 1, 2 | 1, 2 |
| 27 | 5 | 0, 3 | 10 | 0, 08 |

Various modifications of the products and methods of the invention may be without departing from the spirit or scope thereof. It is to be understood that the invention is intended to be limited only as defined in the appended claims.

What we claim is:

1. A syn isomer in (R) or (S) form or a mixture thereof of the formula

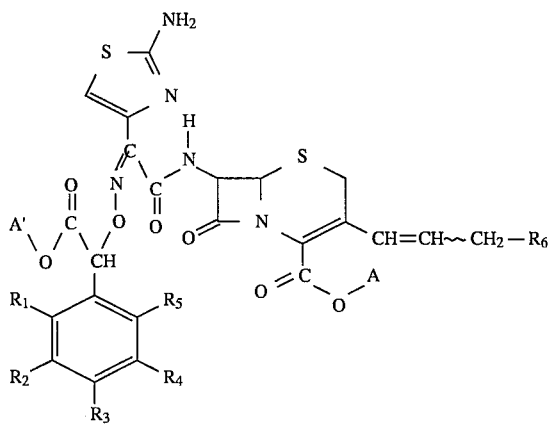

in the form of an internal salt or a non-toxic, pharmaceutically acceptable acid addition salt wherein $R_1$, $R_2$, $R_3$ and $R_5$ are individually selected from the group consisting of hydrogen, halogen, hydroxy, alkyl of 1 to 4 carbon atoms optionally substituted with at least one halogen, alkoxy and alkylthio of 1 to 4 carbon atoms, —$NO_2$, —CN, —$NH_2$, mono- and dialkylamino of 1 to 4 alkyl carbon atoms, carbamoyl, (alkylamino) carbonyl of 2 to 5 carbon atoms, (dialkylamino) carbonyl of 3 to 9 carbon atoms, carboxy, alkoxycarbonyl of 2 to 5 carbon atoms, acyloxy of 1 to 8 carbon atoms and

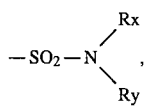

Rx and Ry are individually hydrogen or alkyl of 1 to 4 carbon atoms, $R_4$ is —OH or alkoxy of 1 to 8 carbon atoms, A and A' are individually selected from the group consisting of hydrogen, an equivalent of an alkali metal or alkaline earth metal, magnesium, ammonium and an organic amine or one or two of —COOA or —COOA' are —$CO_2$, the wavy line means —$CH_2R_6$ can be in the E or Z position, $R_6$ in the quaternary ammonium form is selected from the group consisting of

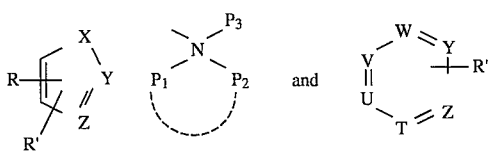

and X is selected from the group consisting of —$CH_2$, —NH—, —O— and —S—, Y, T, U, V, W and Z are individually =N— or —CH=, each of the cyclics containing 1 to 5 heteroatoms of which at least one is =N— and optionally substituted by at least one R or R' are individually selected from the group consisting of halogen, alkyl and alkoxy of 1 to 4 carbon atoms, halogen, —CN, —COOQ$_1$, —CONQ$_1$Q$_2$, —NQ$_1$Q$_2$, —SONQ$_1$Q$_2$, —CSHN$_2$, —NH-COQ$_1$, —CH=NOH, —CH=N-O-Q$_1$, —CH$_2$CN and —CH$_2$—S-Q$_1$, —SO$_1$—, Q$_1$ and Q$_2$ are individually hydrogen or alkyl of 1 to 4 carbon atoms, P$_1$, P$_2$ and P$_3$ are individually alkyl of 1 to 4 carbon atoms optionally substituted with a substituent of R or R' or P$_1$ and P$_2$ taken together with the nitrogen to which they are attached form a 5 or 6 ring heterocycle with the proviso that when $R_3$ is —OH or alkoxy of 1 to 8 carbon atoms, at least one of $R_1$, $R_2$ and $R_5$ is other than hydrogen.

2. A compound of claim 1 wherein $R_6$ is selected from the group consisting of:

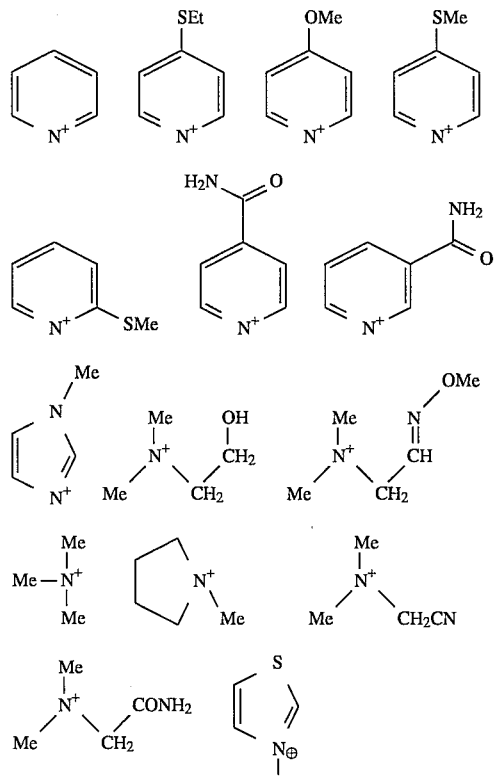

3. A compound of claim 1 wherein $R_3$ and $R_4$ are —OH.
4. A compound of claim 1 wherein $R_2$ and $R_5$ are chlorine.
5. A compound of claim 1 wherein $R_2$ and $R_5$ are fluorine.
6. A compound of claim 1 wherein $R_1$ and $R_2$ are fluorine.
7. A compound of claim 1 wherein $R_2$ is —OCH$_3$ and one of $R_1$ or $R_5$ is chlorine.
8. An antibacterial composition comprising an antibactericidally effective amount of at least one compound of claim 1 and an inert pharmaceutical carrier.
9. A method of treating bacterial infections in warm-blooded animals comprising administering to warm-blooded animals an antibacterially effective amount of at least one compound of claim 1.
10. A method of treating bacterial infections in warm-blooded animals comprising administering to warm-blooded animals an antibacterially effective amount of at least one compound of claim 2.
11. A compound of claim 1 wherein $R_6$ is selected from the group consisting of 4-(methylthio)-pyridinium, pyridinium and 1-methyl-pyrrolidium.
12. A compound of claim 1 selected from the group consisting of the internal salt of (6R-3-(E) 6α, 7δ(Z)))-1-(3 -(7-(((2-amino-4-thiazolyl) (carboxy-(2,5-dichloro-3,4-dihydroxyphenyl) -methoxy)-imino)-acetamido)-2-carboxy-8-oxo-5-thia-1-azabicyclo[ 4,2,0]oct-2-en-3-yl)-2-propenyl)-1-methyl-pyrrolidinium, the internal salt of [6R-[3(E) 6α, 7δB (Z)]]-1-[3-7 (Z)]]-1-[ 3-[7[[(2-amino-4-thiazolyl) [carboxy-(2,5-dichloro-3,4-dihydroxy-phenyl)-methoxy] -imino]-acetamido]-2-carboxy-8-oxo-5-thia-1-azabicyclo [ 4,2,0]oct-2-en-3-yl]-2-propenyl]-4-(methylthio) pyridinium (R) or (S) or an (R+S) mixture and the internal salt of (6R-3(E)-6α, 7δ(Z))-1-3-(7-(((2-amino-4-thiazolyl)(carboxy-2,5 -difluoro-3,4-dihydroxy-phenyl)-methoxy)-imino)-acetamido)-2-carboxy-8 -oxo-5-thia-1-azabicyclo {4,2,0]oct-2-en-3-yl)-2-propenyl)-pyridinium.

13. A method of treating bacterial infections in warm-blooded animals comprising administering to warm-blooded animals an antibacterially effective amount of at least one compound of claim 12.

* * * * *

UNITED STATES PATENT AND TRADEMARK OFFICE
CERTIFICATE OF CORRECTION

PATENT NO. : 5,455,238
DATED : October 3, 1995
INVENTOR(S) : Aszodi, et al

It is certified that error appears in the above-indentified patent and that said Letters Patent is hereby corrected as shown below:

Column 2. line 30, and Column 107, line 55 change

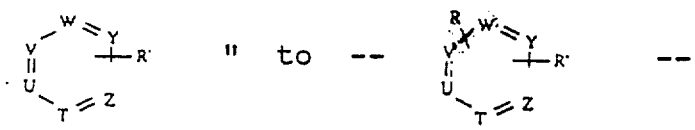 " to --  --

Signed and Sealed this

Thirteenth Day of February, 1996

*Attest:*

BRUCE LEHMAN

*Attesting Officer*  Commissioner of Patents and Trademarks